(12) United States Patent
Pilpel et al.

(10) Patent No.: US 11,879,140 B2
(45) Date of Patent: Jan. 23, 2024

(54) P21 MRNA TARGETING DNAZYMES

(71) Applicant: 1E Therapeutics Ltd., Rehovot (IL)

(72) Inventors: Noam Pilpel, Rehovot (IL); Yossi Ovadya, Rehovot (IL); Dina Raichlin, Rehovot (IL); Etti Katz-Kadosh, Rehovot (IL); Alaa Knany, Rehovot (IL); Ella Gillis, Rehovot (IL); Noam Borovsky, Rehovot (IL); Anastasia Shapiro, Rehovot (IL); Ido Bachelet, Rehovot (IL)

(73) Assignee: 1E THERAPEUTICS LTD., Rehovot (IL)

( * ) Notice: Subject to any disclaimer, the term of this patent is extended or adjusted under 35 U.S.C. 154(b) by 0 days.

(21) Appl. No.: 18/342,853

(22) Filed: Jun. 28, 2023

(65) Prior Publication Data

US 2023/0365952 A1 Nov. 16, 2023

Related U.S. Application Data

(63) Continuation of application No. PCT/IL2021/051546, filed on Dec. 28, 2021.

(60) Provisional application No. 63/130,937, filed on Dec. 28, 2020.

(51) Int. Cl.
*C12N 9/22* (2006.01)
*A61P 13/12* (2006.01)

(52) U.S. Cl.
CPC ............... *C12N 9/22* (2013.01); *A61P 13/12* (2018.01)

(58) Field of Classification Search
CPC .................................. C12N 15/113
See application file for complete search history.

(56) References Cited

U.S. PATENT DOCUMENTS

| 3,687,808 | A | 8/1972 | Merigan et al. |
| 3,850,578 | A | 1/1974 | Mcconnell |
| 3,791,932 | A | 2/1974 | Schuurs et al. |
| 3,839,153 | A | 10/1974 | Schuurs et al. |
| 3,850,752 | A | 11/1974 | Schuurs et al. |
| 3,853,987 | A | 12/1974 | Dreyer |
| 3,867,517 | A | 2/1975 | Ling |
| 3,879,262 | A | 4/1975 | Schuurs et al. |
| 3,901,654 | A | 8/1975 | Gross |
| 3,935,074 | A | 1/1976 | Rubenstein et al. |
| 3,984,533 | A | 10/1976 | Uzgiris |
| 3,996,345 | A | 12/1976 | Ullman et al. |
| 4,034,074 | A | 7/1977 | Miles |
| 4,098,876 | A | 7/1978 | Piasio et al. |
| 4,659,774 | A | 4/1987 | Webb et al. |
| 4,666,828 | A | 5/1987 | Gusella |
| 4,683,202 | A | 7/1987 | Mullis |
| 4,801,531 | A | 1/1989 | Frossard |
| 4,816,571 | A | 3/1989 | Andrus et al. |
| 4,879,219 | A | 11/1989 | Wands et al. |
| 4,959,463 | A | 9/1990 | Foehler et al. |
| 5,011,771 | A | 4/1991 | Bellet et al. |
| 5,141,813 | A | 8/1992 | Nelson |
| 5,192,659 | A | 3/1993 | Simons |
| 5,264,566 | A | 11/1993 | Froehler et al. |
| 5,272,057 | A | 12/1993 | Smulson et al. |
| 5,281,521 | A | 1/1994 | Trojanowski et al. |
| 5,428,148 | A | 6/1995 | Reddy et al. |
| 5,464,764 | A | 11/1995 | Capecchi et al. |
| 5,487,992 | A | 1/1996 | Capecchi et al. |
| 5,554,744 | A | 9/1996 | Bhongle et al. |
| 5,574,146 | A | 11/1996 | Reddy et al. |
| 5,602,244 | A | 2/1997 | Caruthers et al. |
| 5,998,203 | A | 12/1999 | Matulic-adamic et al. |
| 6,326,174 | B1 * | 12/2001 | Joyce ............. C12Q 1/6811 536/23.1 |
| 6,361,941 | B1 | 3/2002 | Todd et al. |
| 8,686,128 | B2 | 4/2014 | Khachigian |
| 10,023,597 | B2 | 7/2018 | Minomi et al. |
| 2003/0125270 | A1 | 7/2003 | Blatt et al. |
| 2004/0266734 | A1 | 12/2004 | Dannenberg et al. |
| 2005/0064407 | A1 | 3/2005 | Sun et al. |
| 2005/0222065 | A1 | 10/2005 | Khachigian |
| 2010/0249216 | A1 | 9/2010 | Sel et al. |
| 2011/0065772 | A1 | 3/2011 | Khachigian |
| 2013/0237696 | A1 | 9/2013 | Khachigian |
| 2020/0121620 | A1 | 4/2020 | Gil et al. |

FOREIGN PATENT DOCUMENTS

| WO | WO 1993/015187 A1 | 8/1993 |
| WO | WO 1999/050452 A1 | 10/1999 |
| WO | WO 2002/081494 A1 | 10/2002 |
| WO | WO 2002/099090 A1 | 12/2002 |
| WO | WO 2005/0003331 A1 | 1/2005 |
| WO | WO 2009/003211 A1 | 1/2009 |
| WO | WO 2010/077366 A2 | 7/2010 |
| WO | WO 2012/087983 A1 | 6/2012 |
| WO | WO 2013/126963 A1 | 9/2013 |
| WO | WO 2014/107763 | 7/2014 |
| WO | WO 2014/174511 A1 | 10/2014 |
| WO | WO 2016/106402 A1 | 6/2016 |

(Continued)

OTHER PUBLICATIONS

Abbas et al. "p21 in cancer: intricate networks and multiple activities" Nature reviews. Cancer. Jun. 2009;9(6):400.

(Continued)

*Primary Examiner* — Suzanne M Noakes

(74) *Attorney, Agent, or Firm* — Mark S. Cohen; PEARL COHEN ZEDEK LATZER BARATZ LLP

(57) ABSTRACT

A composition of matter comprising a DNAzyme molecule capable of mediating cleavage of p21 mRNA corresponding to SEQ ID NO: 1, wherein said DNAzyme molecule comprises a nucleic acid sequence at least 80% identical to the nucleic acid sequence set forth in any one of SEQ ID NOs: 23, 29, 33-38, 40, 42, 45-48, 53-60, 63-65, 69-74 or 78, is disclosed. Methods of eradicating senescent cells or cancer cells, as well as methods of treating senescence-associated diseases or disorders, cancer, and fibrotic diseases and disorders are also disclosed.

24 Claims, 22 Drawing Sheets

Specification includes a Sequence Listing.

(56) References Cited

FOREIGN PATENT DOCUMENTS

| WO | WO 2016/135732 A1 | 9/2016 |
|---|---|---|
| WO | WO 2016/185481 A1 | 11/2016 |

OTHER PUBLICATIONS

Ashcroft et al. "Simple method of estimating severity of pulmonary fibrosis on a numerical scale" Journal of Clinical Pathology. Apr. 1988;41(4):467.

Asseline et al. "Improved nuclear delivery of antisense 2'-Ome RNA by conjugation with the histidine-rich peptide HSWYG" The journal of gene medicine. 2014;16(7-8):157-65.

Asthana et al. (2014) "Mannosylated Chitosan Nanoparticles for Delivery of Antisense Oligonucleotides for Macrophage Targeting" BioMed Research International. 2014:Article #526391.

Bartel DP. "MicroRNAs: genomics, biogenesis, mechanism, and function" Cell. Jan. 23, 2004;116(2):281-97.

Breaker et al. "A DNA enzyme that cleaves RNA" Chemistry & biology. Dec. 1994;1(4):223-9.

Brennecke et al. "Principles of MicroRNA-Target Recognition" PLOS Biology, Mar. 2005;3(3):e85.

Campisi et al. "Cellular senescence: when bad things happen to good cells" Nature reviews. Molecular cell biology. Sep. 2007;8(9):729-40.

Coppé et al. "The Senescence-Associated Secretory Phenotype: The Dark Side of Tumor Suppression" Annual review of pathology. 2010;5:99-118.

Danenberg et al. "Systemic depletion of macrophages by liposomal bisphosphonates reduces neointimal formation following balloon-injury in the rat carotid artery" Journal of cardiovascular pharmacology. Nov. 1, 2003;42(5):671-9.

Danenberg et al. "Macrophage depletion by clodronate-containing liposomes reduces neointimal formation after balloon injury in rats and rabbits" Circulation. Jul. 30, 2002;106(5):599-605.

Danenberg et al. "Liposomal alendronate inhibits systemic innate immunity and reduces in-stent neointimal hyperplasia in rabbits" Circulation. Dec. 2, 2003;108(22):2798-804.

Deleavey et al. "Designing chemically modified oligonucleotides for targeted gene silencing" Chemistry & biology. Aug. 24, 2012;19(8):937-54.

De Mesmaeker et al. "Amides as a New Type of Backbone Modification in Oligonucleotides" Angew. Chem. Int. Ed. Engl. 1994, 33, No. 2., 1994, pp. 226-229.

Falzarano et al. "Nanoparticle Delivery of Antisense Oligonucleotides and Their Application in the Exon Skipping Strategy for Duchenne Muscular Dystrophy" Nucleic Acid Therapeutics. Feb. 2, 2014;24(1):87.

Feldman et al. "A new and efficient DNA enzyme for the sequence-specific cleavage of RNA" Journal of molecular biology. Oct. 19, 2001;313(2):283-94.

Fleury et al. "Exploiting interconnected synthetic lethal interactions between PARP inhibition and cancer cell reversible senescence" Nature Communications. 2019;10;2556.

Gait MJ. "Peptide-mediated cellular delivery of antisense oligonucleotides and their analogues" Cellular and molecular life sciences. May 2003;60(5):844-53.

GeneBank Accession No. NM_001291549.3, version 3, Nov. 30, 2021.

GeneBank Accession No. NM_000389.5, version 5, Dec. 1, 2021.

GeneBank Accession No. NM_001220777.2, version 2, Nov. 30, 2021.

GeneBank Accession No. NM_001220778.2, version 2, Nov. 29, 2021.

GeneBank Accession No. NM_001374509.1, version 1, Nov. 29, 2021.

GeneBank Accession No. NM_001374510.1, version 1, Nov. 29, 2021.

GeneBank Accession No. NM_001374511.1, version 1, Nov. 29, 2021.

GeneBank Accession No. NM_001374512.1, version 1, Nov. 29, 2021.

GeneBank Accession No. NM_001374513.1, version 1, Nov. 29, 2021.

GeneBank Accession No. NM_078467.3, version 3, Nov. 29, 2021.

Gilboa E. "Transfer and expression of cloned genes using retroviral vectors" BioTechniques. 1986;4:504-12.

Grijalvo et al. "Oligonucleotide delivery: a patent review (2010-2013)" Expert opinion on therapeutic patents. Jul. 2014;24(7):801-19.

Hollenstein M. "DNA Catalysis: The Chemical Repertoire of DNAzymes" Molecules (Basel, Switzerland). Nov. 20, 2015;20(11):20777-604.

Huang et al. "Thioredoxin interacting protein (TXNIP) regulates tubular autophagy and milophagy in diabetic nephropathy through the mTOR signaling pathway" Scientific reports. Jul. 6, 2016;6:29196.

Inoue et al. "Sorafenib attenuates p21 in kidney cancer cells and augments cell death in combination with DNA-damaging chemotherapy" Cancer Biology & Therapy. Nov. 11, 2011;12(9):827.

International Search Report for PCT Application No. PCT/IL2021/051546 dated Sep. 2, 2022.

International Search Report for PCT Application No. PCT/IL2021/051545 dated Jul. 25, 2022.

Jääskeläinen et al. "In vitro delivery of antisense oligonucleotides" Cellular & molecular biology letters. 2002;7(2):236-7.

Jiang et al. "Local and transient inhibition of p21 expression ameliorates age-related delayed wound healing" Wound repair and regeneration: official publication of the Wound Healing Society [and] the European Tissue Repair Society. Jan. 2020;28(1):49-60.

Kabanov et al. "A new class of antivirals: antisense oligonucleotides combined with a hydrophobic substituent effectively inhibit influenza virus reproduction and synthesis of virus-specific proteins in MDCK cells" FEBS letters. Jan. 1, 1990;259(2):327-30.

Khachigian LM. "Deoxyribozymes as Catalytic Nanotherapeutic Agents" Cancer research. Mar. 1, 2019;79(5):879-88.

Kirkland et al. "Clinical Strategies and Animal Models for Developing Senolytic Agents" Experimental gerontology. Aug. 2015;68:19.

Krek et al. "Combinatorial microRNA target predictions" Nature genetics. May 1, 2005;37(5):495-500.

Letsinger et al. "Cholesteryl-conjugated oligonucleotides: synthesis, properties, and activity as inhibitors of replication of human immunodeficiency virus in cell culture" Proceedings of the National Academy of Sciences of the United States of America. Sep. 1989;86(17):6553-6.

Lewis et al. "Conserved seed pairing, often flanked by adenosines, indicates that thousands of human genes are microRNA targets" Cell. Jan. 14, 2005;120(1):15-20.

Löfdahl et al. "Pulmonary fibrosis in vivo displays increased p21 expression reduced by 5-HT2B receptor antagonists in vitro-a potential pathway affecting proliferation" Scientific Reports. 2018;8:1927.

Martino et al. "Efficient siRNA Delivery by the Cationic Liposome DOTAP in Human Hematopoietic Stem Cells Differentiating into Dendritic Cells" Journal of Biomedicine and Biotechnology. 2009;2009:Article ID 410260.

Mokany et al. "MNAzymes, a Versatile New Class of Nucleic Acid Enzymes That Can Function as Biosensors and Molecular Switches" Journal of the American Chemical Society. Jan. 1, 2010;132(3):1051.

Oberhauser et al. "Effective incorporation of 2'-O-methyl-oligoribonucleotides into liposomes and enhanced cell association through modification with thiocholesterol" Nucleic acids research. Feb. 11, 1992;20(3):533-8.

Ovadya et al. "Strategies targeting cellular senescence" The Journal of Clinical Investigation. Apr. 4, 2018;128(4):1247.

Paddison et al. "Stable suppression of gene expression by RNAi in mammalian cells" Proceedings of the National Academy of Sciences of the United States of America. Feb. 5, 2002;99(3):1443-8.

Pandya et al. "Nanocomposites and IT'S application-review" International Journal of Pharmaceutical Sciences and Research. 2013;4(1):19-28.

(56) References Cited

OTHER PUBLICATIONS

Park et al. "High throughput screening of a small molecule one-bead-one-compound combinatorial library to identify attenuators of p21 as chemotherapy sensitizers" Cancer biology & therapy. Dec. 2008;7(12):2015-22.

Prakash et al. "Targeted delivery of antisense oligonucleotides to hepatocytes using triantennary N-acetyl galactosamine improves potency 10-fold in mice" Nucleic acids research. Jul. 2014:42(13):8796-807.

Roberts et al. "Advances in oligonucleotide drug delivery" Nature Reviews. Drug Discovery. 2020;19(10):673.

Sagiv et al. "p53 in Bronchial Club Cells Facilitates Chronic Lung Inflammation by Promoting Senescence" Cell reports. Mar. 27, 2018;22(13):3468-79.

Saison-Behmoaras et al. "Short modified antisense oligonucleotides directed against Ha-ras point mutation induce selective cleavage of the mRNA and inhibit T24 cells proliferation" The EMBO Journal. May 1991;10(5):1111.

Santoro in"A general purpose RNA-cleaving DNA enzyme" Proceedings of the National Academy of Sciences of the United States of America, Apr. 4, 1997;94(9):4262.

Sax et al. "The cyclin-dependent kinase inhibitor butyrolactone is a potent inhibitor of p21 (WAF1/CIP1 expression)" Cell cycle (Georgetown, Tex.). Jan. 2002;1(1):90-6.

Seluanov et al. "Establishing Primary Adult Fibroblast Cultures from Rodents" Journal of Visualized Experiments: JoVE Journal of Visualized Experiments. 2010:(44)44. http://www.jove.com/details.php?id=2033.

Shea et al. "Synthesis, hybridization properties and antiviral activity of lipid-oligodeoxynucleotide conjugates" Nucleic acids research. Jul. 11, 1990;18(13):3777-83.

Shinagawa et al. "Generation of Ski-knockdown mice by expressing a long double-strand RNA from an RNA polymerase II promoter" Genes & Development. Jun. 6, 2003;17(11):1340.

Tran et al. "Control of specific gene expression in mammalian cells by co-expression of long complementary RNAs" FEBS letters. Aug. 27, 2004;573(1-3):127-34.

Tuschl T. "Rna interference and small interfering RNAs" Chembiochem: a European journal of chemical biology. Apr. 2, 2001;2(4):239-45.

Wang et al. "DNA enzyme ED5 depletes egr-1 and inhibits neointimal hyperplasia in rats" Cardiology. 2013;125(3):192-200.

Wettersten et al. "A novel p21 attenuator which is structurally related to sorafenib" Cancer Biology & Therapy. Mar. 3, 2013;14(3):278.

Xiang et al. "Downregulated expression of plasminogen activator inhibitor-1 augments myocardial neovascularization and reduces cardiomyocyte apoptosis after acute myocardial infarction" Journal of the American College of Cardiology. Aug. 2, 2005:46(3):536-41.

Xu et al. "Senolytics Improve Physical Function and Increase Lifespan in Old Age" Nature medicine. Aug. 2018;24(8):1246.

Yao et al. "Suppression of Transcription Factor Early Growth Response 1 Reduces Herpes Simplex Virus 1-Induced Corneal Disease in Mice" Journal of Virology. Aug. 2012;86(16):8559.

Yosef et al. "p21 maintains senescent cell viability under persistent DNA damage response by restraining JNK and caspase signaling" The EMBO Journal. Aug. 8, 2017;36(15):2280.

Zhou et al. "Theranostic dnazymes" Theranostics. 2017;7(4):1010.

\* cited by examiner

FIG. 3

>NM_001291549.3 Homo sapiens cyclin dependent kinase inhibitor 1A (CDKN1A), transcript variant 3, mRNA

```
ATGTTTGAGCTCTGGCATAGAAGAGGCTGGTGGCTATTTTGTCCTTGGGCTGCCCTGTTTTCAGGTGAGGAAGGGATGGTAGGAGACAGGAGA
CCTCTAAAGACCCCAGAGAAATAAGGCAGATGACAAGCAGAGAGCCCGGGCAGGAGGCAAAAGTCCTGTGTTCCAACTATAGTCATTTCTTTGCT
GCATGATCTGAGTTAGGTCACCAGACTTCTCTGGCCCCAGTTTCCCAGCAGTGTATACGGCTATGTGTTGGGGAGTATTCAGGAGACAGACA
ACTCACTCGTCAAATCCTCCCCCTTCCTGGCCAACAAAGCCCTGCCGCCAGTTTCTCTGTTCAGGCGCCATGTCAGAACCGGCTGG
GGATGTCCGTCAGAACCCATGCCAGGAGCCCGTGAGCGATGGAACTTTGTCCGAGACACCACTGGAGGGTGACTTCGCCTGGGAGCGT
TAATGGCGGGCGGCCCTTGCCTGCCCAAGCTCTACCTTCCCACAGGCCCCGTGAGCGATGTACCCTTGTGCCTCGCTCAGGGACCAGGCTGAAG
GTGCGGGGGCCCTTGCCTGCTCAGGGACACAGCAGAGACCATGTGAAGAAGACACCACTGGAGGGTGACTTCGCTCAGGCTGATCTTC
ACCTGCTCTGCTCCCAGGTGGACCTGGAGACTCTCAGGTCGAAAACGGGGCAGCATGACAGATTTCTACCACTCCAAACGCCGGCTGATCTTC
GGTCCCCAGGGAAGCCCTAATCGCCACAGGAAGCCTGCAGTCCTGGAAGCGCGATTTTATTTATTGAAATGAAAATACTATTTAAAAGCCT
TCCAAGAGGAAGCCCTAATCCGCCACAGGAAGCCTCAGTCCTGGAAGCCCATTTTATTTATTGAAATGAAATACTATTTAAAGCCT
TCAGTTTGTGTGTCTTAATAATTATTTGTGTTTTTTAATTGAATGAAGTTCCTAAGAGTGCTGGGCATTCATCACCCCTCCTAAGACCT
ATTAGAATATTAAACAAAAACTAGGCGGTTGAATGAAGTTCCTAAGAGTGCTGGGCATTCATCACCCCTCCTAAGAACCT
CCCTCATCCCGTGTCTCTGTTTCCCTTTTCCCCCGGAGGTTGGGTGGGACCTGAGCTGGGCCTTGTTGGCCCCTGCCCTGAGTGGGAGACCTGAATTCT
GGTACCCCTCTGGAGGGTGTGCCTTCCCATGGACAGATGAAGTGAAGACATGAAGCCCTAGGGGGCTCACCGAGTGCCCCTGAGCGCACC
TTTTCATTTGAGAAGAAGTAAACAGATGAAGTGACGTGCCCCTTGGCTCACTTTGAAGGTCACTTTGAAGGGCCTAGGGCACCCCTTAACCCTCCTA
AGGTTGGGCAGGTGACCCTGAAGTGGGCTCACTTTGAAGGCACACAACTTGAAGCCTAGTCCCAGGCTCCTGACCTGCACCTGAATTCACCCCCCTGTCTTG
TGAAGGCAGGGCCCCCAAATCGTCGGAGGCACTGGAGGGCAGAGCCTGGCTCCAGGCTCCTGAGGTGCCTGTCCAGGTGGCTCAGTGTT
GAGCCTTTCCTCCCCCTTGTCCTTTCCCTTGTCCCCTTTTTGAGGTGCCTGTCCAGGTGGCTCAGTGCCCACCCCCTCCAGCTCAATGGACT
GTCCCCCATGTGGCAAGGGAGACACAAGAAGAGCCCCCAGCTCAGCAGTTCTACCTAGTTGGGGTATCTCTGTTAGGGTGATCTTTCTAGGAGAGA
GGAAGGGACAAGGCAGGACACAACAAGGCACCCCTTGAGTGGGTTATCTCTGTTAGGGTGATCTTTCTAGGAGAGA
AGGGTCCCATGTGGTGGCACAAATCGTCGTGGCAGTAGAGCCATGCCACGTGGGCTCAGTTCAGCGGAACAAGGAGTCA
CACTGGCCCCAAATGTGGTGGCAGTAGAGCCATGCCACGTGGGCTCAGTTCAGCGGAACAAGGAGTCA
GACATTTAAGATGTGGCAGGCACTGAAGTGCTTAGTGTACTTGGAGTATTGGGGTCTGTGTTTCCTGCACATACTGGCC
CGTTGAGCCCCCTGGAGGCACTGAAGTGCTTAGTGTACTTGGAGTATTGGGGTCTGACCCCAAACACCTTCCTGTAACATACTGGCC
TGGACTGTTCTCTCGGCTGCCTTTCACACAGCCTCCTGGTCCCCGTTTCCCTAGACTGTAAACCTCTGAGGGCAGGACCACACCCTGTAC
TGTTCTGTGTGTCTGTTTCACAGCTCCACAGCTGCTCACAATGCTGAATATACAGAGGTGCTCAATAAATGATTCTTAGTGACTTTA
```

SEQ ID NO: 1

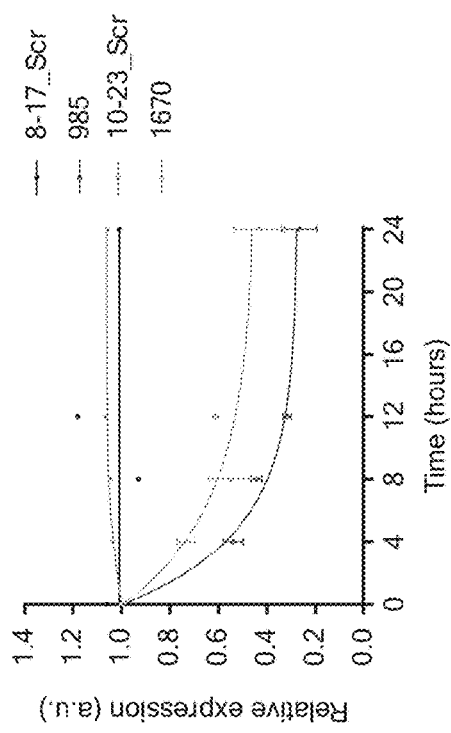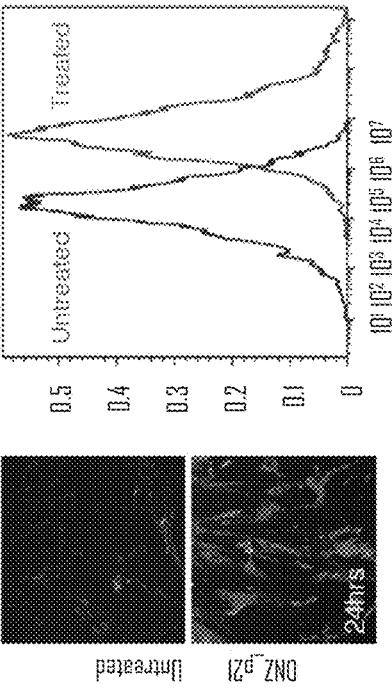

FIG. 8

>NM_007669.5 Mus musculus cyclin-dependent kinase inhibitor 1A (P21) (Cdkn1a), transcript variant 1, mRNA TGCAGCAGCCGAGAGGTGTGAGCCCGCGCGGTGTCAGAGTCTTAGGGAATTGGAGTCAGGCGCAGATCCA
CAGCGATATCCAGACATTCAGAGCCACAGGCCACACAGGCCACCATGTCCAATCCTGGTGATGTCCGACCTGTTCCGCAC
AGGAGCAAAGTGTGCCGTTGTCTCTTCGGTCTGTTGGACCAGTTGCGCCGTGATTGCGATGCGC
TCATGGCGGGCTGTCTCCAAGAGGCCCGAGAACGGTGGAACTTTGACTTCGTCACGGAGACGCCGGA
GGGCAACTTCGTCTGGGAGCGCGTTCGGAGCCCTAGGGCTGCCAGTACTTCCTCTGCCCTGCTTGGGTCCGC
AGCCGTGACGACCTGGGAGGGGACAAGAGGGCCAGTACTTCCTCTGCTCTGAGCCTCGAGGGGCCAGTCCGG
AGGACCACGTGGCCCTTGTCGTCCGGCCTGTCTTGCACTCTGGTGTCTGACACTGCGAAGATTCCCGCGGGTGGCC
CGGAACATCTCAAGGCCGAAAACGGAGGCAGACCAGCTCAGAGGATTTCTATCACTCCTGTGGTCAGGAGCC
GTCTTCTGCAAGAGAAACCCTGAAGTGCCACTCCTCAGCGTGTGTCTCCAGTCTCCAAACTTAAAGTTAAAACGT
TCTTCCCATCTTCGGCCTTAGCCCTCACTCTGTGTGTGTCTTAATTATTATTTGTGTTTTAATTTAAACGT
CTCCTGTATATACGCTGCCTGCCTGCCAGTCTCCAGTGCCCAAGAACAAAAACCAAAACAAAAACCAAAACAAAACA
AAACAAAAAACCAAAACCAAAACAAAACCAAACCTAAATTAGTAGGACGGTAGGGCCCTTAGTGTGGGGATTTC
TATTATGTAGATTATTATTATTAAGCCCCTCCCAACCCAAGCTCTGTGTTTCCTATACCGGAGGAACAG
TCCTACTGATATCAACCCATCTGCATCCGTTTCACCCAACCCCCCCGTTTGGAAAATGAGTAGGACTTTGGG
TGCCACTTCTTACCTGGGGTGATCCTCAGACCTAGGATGACAGTGAAGCAGTCACAGCCTAGAACAGGGATGGCAGT
TCTCCTTGTCACCTCTAAGGCCAGCTAGCCCAGCTCTTGACATTGCTGACATTGCTGAAGACAGGAATGGTCCCACTC
TAGGACTCAACCGTAATATCCGACTCTTGACATTGCTGACATTGCTGAAGACAGGAATGGTCCCCACTC
TGGATCCCCTTTGCCACTCCTGGGAGCCCACCTGCTCTTTTCCCCACCCCATACTTCCCCTTTCTGCAGTCGGCAGGAG
GAGGGTTAATCTGGTGTGAATCGGTCACTTGCCCCACAGCTCAGCTCTGCTCTTTTCCCCACCCCATACTTCCCCTTTCTGCAGTCGGCAGGAG
GCATATCTAGGCACTTGCCCCACAGCTCAGCTCAGCTCTGCTCTTTTCCCCACCCCATACTTCCCCTTTCTGCAGTCGGCAGGAG
GATTCCCCTGGTCTTTACCTTAGGCAGCTCCCAGTGGACTGGCAACCCCCTGCATTGTGGGTCTAGGGTGGGTCCTTG
GTGGTGAGACAGGCCTCCCAGAGCATTCTATGGTGGTGGGGTTATCTGGGGATGGGGA
CCCAGTTGGGGTTCCCAGTGACTTTCTCCCATTTCTTAGTAGCAGTTGTACAGGAGCCAAGCCAAGATG
GTGTCTTGGGGCCTAAGGGAGCTCAAGGGAGCTCACCCCCGCTAAGTGGTCTGACTGTGATCCTTTCCTGTTTCTGTAACATCCTGGTCTG
TGGGTGTCAAAGCCACTTAGTGGGTCTGACTGCCCCAAGACATGTATTGTGGCTCCCCTGTCCCACTCAGATTGT
AAGCGTCTCACGAGAAGCACCCTGCATTGTCCCGAGTCCTCACACCCGACCCCAAAGCTGGTGC
TCAATAAATACTTCTCGATGATT

SEQ ID NO: 3

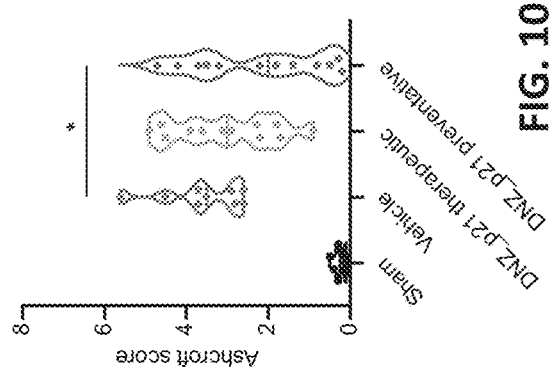
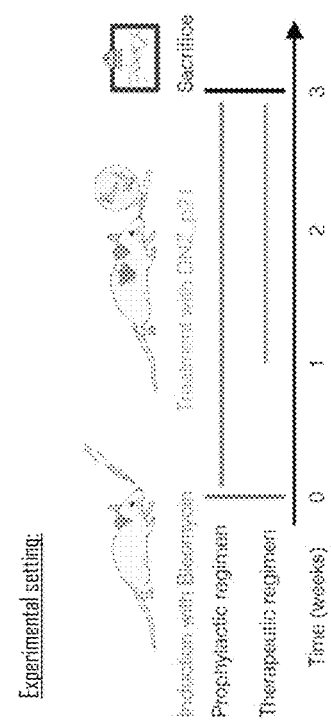
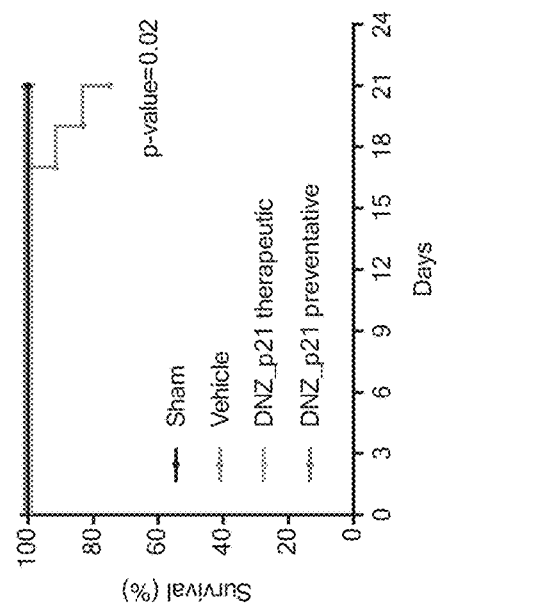
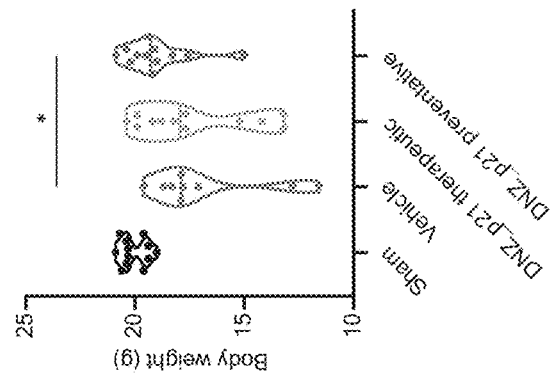

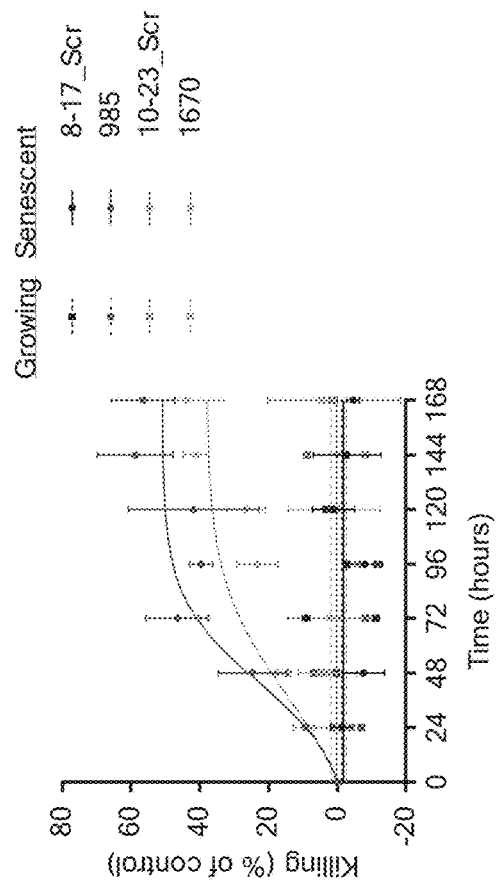
FIG. 12A
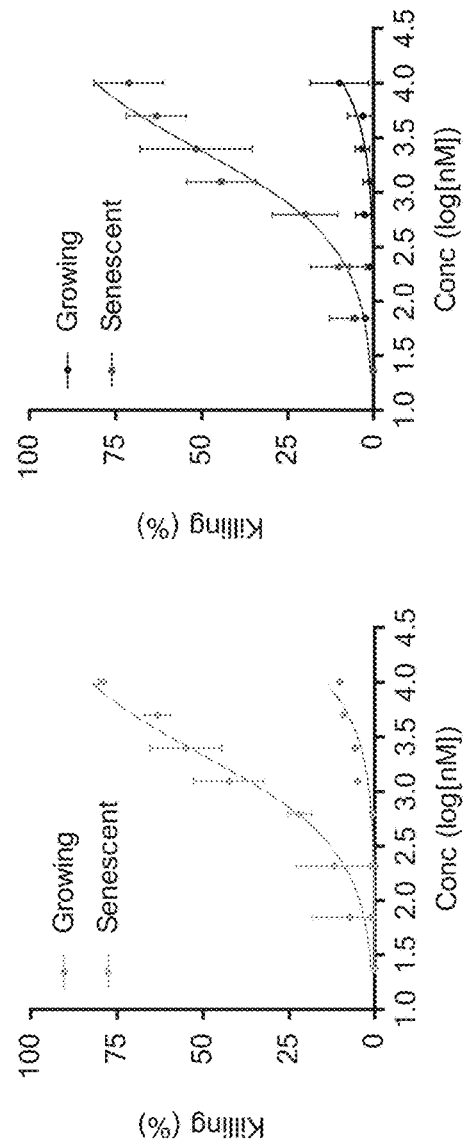
FIG. 12B
FIG. 12C

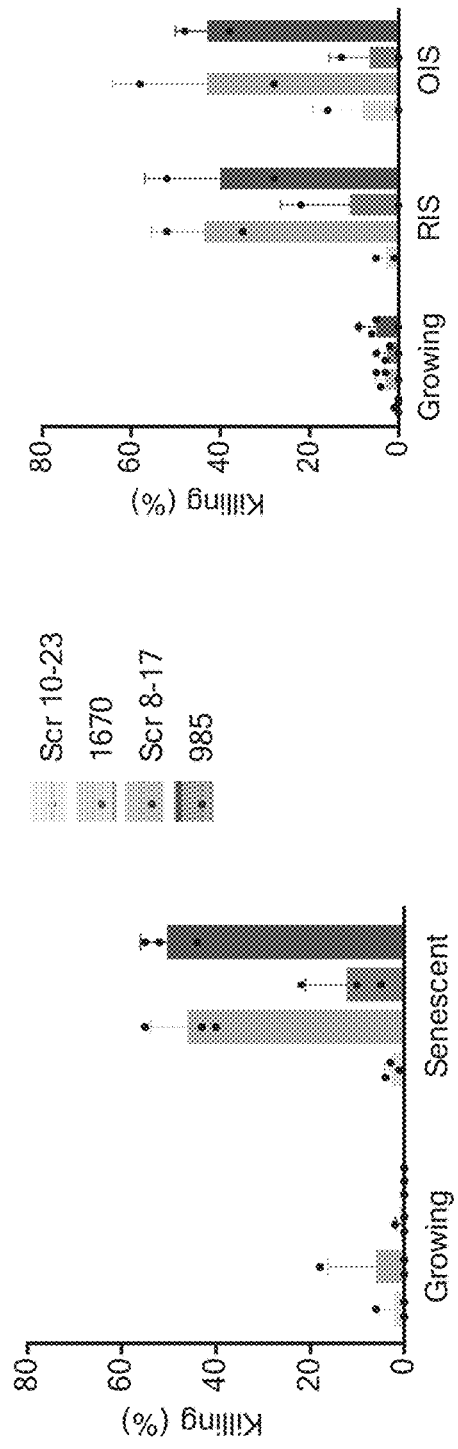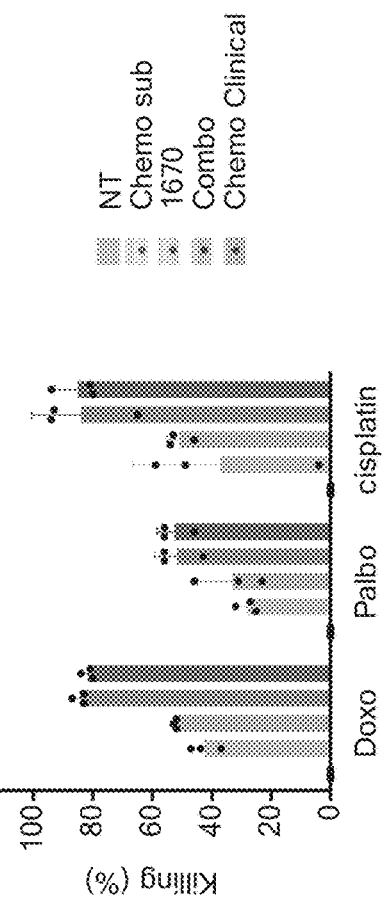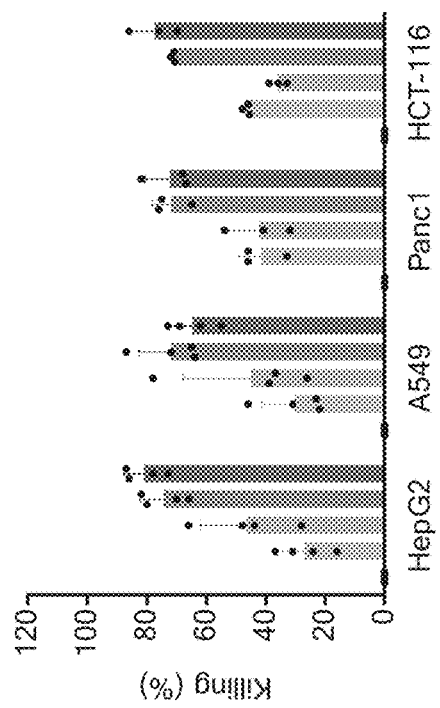

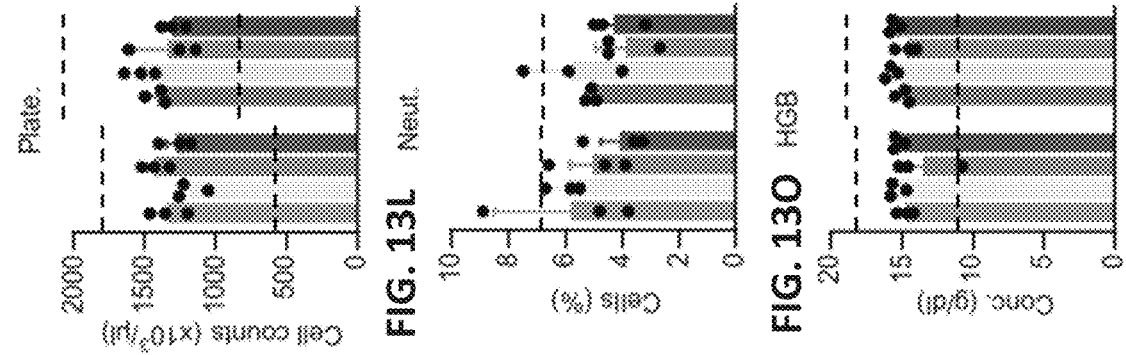
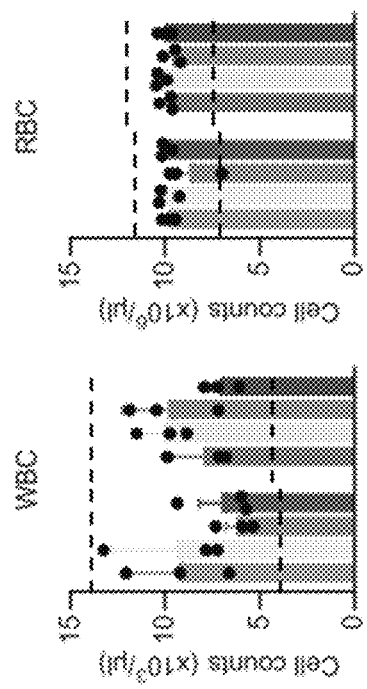
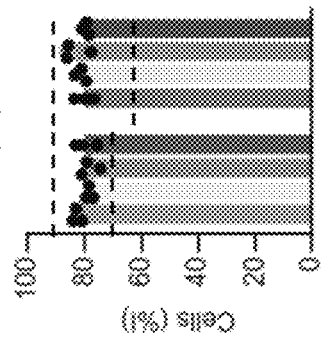
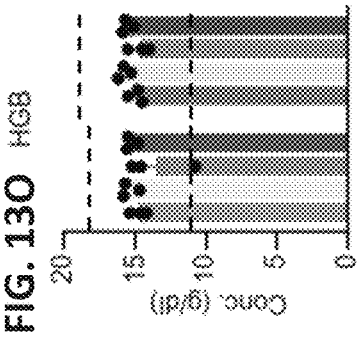
FIG. 13G  FIG. 13H  FIG. 13I
FIG. 13J  FIG. 13K  FIG. 13L
FIG. 13M  FIG. 13N  FIG. 13O

P21 MRNA TARGETING DNAZYMES

CROSS-REFERENCE TO RELATED APPLICATIONS

This application is a continuation application of PCT International Application No. PCT/IL2021/051546, International Filing Date Dec. 28, 2021, claiming the benefit of U.S. Patent Application No. 63/130,937, filed Dec. 28, 2020, which are hereby incorporated by reference in their entirety.

SEQUENCE LISTING STATEMENT

The instant application contains a Sequence Listing which has been submitted electronically to in XML format and is hereby incorporated by reference in its entirety. Said XML copy, created on Jul. 26, 2023, is named P-616662-US_SL.xml and is 164,808 bytes in size.

FIELD AND BACKGROUND OF THE INVENTION

The present invention, in some embodiments thereof, relates to p21 mRNA targeting DNAzymes and, more particularly, but not exclusively, to the use of same for therapeutics.

Cellular Senescence

Cellular senescence is a stable form of cell cycle arrest that limits the proliferative potential of cells. The senescence program is triggered in many cell types in response to various stresses and is associated with age-related diseases. Senescent cells typically accumulate in tissues and contribute to the establishment of a chronic inflammation that arises due to continuous secretion of pro-inflammatory cytokines via the senescence associated secretory phenotype (SASP).

Several approaches that focus on either clearance of senescent cells or prevention of their pro-inflammatory impact are in development for therapeutics. Efforts are largely invested in the discovery of pharmacological agents that can induce cell death in senescent cells. These compounds are generally termed "senolytic drugs" or "senolytics." Senolytics have emerged as promising agents for treatment of pulmonary fibrosis, atherosclerosis, osteoarthritis, type 1 and 2 diabetes mellitus, and neurocognitive decline [Ovadya, and Krizhanovsky, *The Journal of clinical investigation* (2018) 128(4): 1247-1254], for rejuvenation of aged hematopoietic and muscle stem cells and for extending the lifespan of naturally aged mice [Xu et al., *Nature medicine* (2018) 24(8): 1246-1256].

Cellular senescence has also been implicated as a major cause of morbidity in cancer. It is well established that chemotherapy may not completely eliminate cancer cells and that recurrent cancer is typically more aggressive and refractory to therapy. Therapy-induced-senescence (TIS) is thought to be an underlying cause of this phenomenon wherein certain populations of the cancer cells being exposed to sub-lethal chemotherapeutic DNA damaging agents, utilize senescence as a cellular escape mechanism thereby exacerbating the patient's condition e.g. via SASP. Senolytics may therefore improve the prognosis and treatment of cancer patients. An alternative treatment regime which has been suggested, referred to as the "one-two punch" [Fleury et al., *Nature communications* (2019) 10(1): 1-15] contemplates first applying chemotherapy at doses which do not eliminate the cancer cells (but rather induce them to senesce) followed by the second "punch" which consists of a senolytic agent to eliminate these cancer senescent cells.

p21

As illustrated in FIG. 1, cellular senescence is controlled by the p53 and p16-retinoblastoma protein (pRB) tumor suppressor pathways. Senescence-inducing signals, including those that trigger a DNA-damage response (DDR), as well as many other stresses, usually engage one of these two pathways. Some signals, such as oncogenic RAS, engage both pathways. p53 is negatively regulated by the E3 ubiquitin-protein ligase HDM2 (MDM2 in mice), which facilitates its degradation, and HDM2 is negatively regulated by the alternate-reading-frame protein (ARF). Active p53 establishes the senescence growth arrest in part by inducing the expression of p21, a cyclin-dependent kinase (CDK) inhibitor that, among other activities, suppresses the phosphorylation and, hence, the inactivation of pRB. Senescence signals that engage the p16-pRB pathway generally do so by inducing the expression of p16, another CDK inhibitor that prevents pRB phosphorylation and inactivation. pRB halts cell proliferation by suppressing the activity of E2F, a transcription factor that stimulates the expression of genes that are required for cell-cycle progression. E2F can also curtail proliferation by inducing ARF expression, which engages the p53 pathway. Accordingly, there is reciprocal regulation between the p53 and p16-pRB pathways and the senescence program is driven by a complex interplay of signaling pathways. To promote and support cell cycle arrest, p16INK4A (CDKN2A), accompanied by the p53 target p21 (CDKN1A, WAF1, CIP1), inhibits cyclin-dependent kinases (CDKs), thereby preventing phosphorylation of the retinoblastoma protein (pRb) and thus in turn suppressing the expression of proliferation-associated genes.

In normal cells, p21 maintains its genuine signature function as a cell-cycle inhibitor and anti-proliferative effector. Upregulation of p21 enables senescent cells to maintain their viability after damage induction, and allows their retention within tissues [Yosef, R. et al., *The EMBO journal* (2017) 36(15), 2280-2295]. Increased expression of p21 was evident in various age-related conditions associated with cellular senescence [Coppé et al., *Annual Review of Pathological Mechanical Disease* (2010) 5: 99-118] and in a bleomycin induced pulmonary fibrosis model [Lofdahl et al., *Scientific reports* (2018) 8(1): 1-9]. Increased levels of p21 were evident in a Chronic Obstructive Pulmonary Disease (COPD) mouse model and senolytic treatment by ABT-737 reduced p21 levels [Sagiv et al., *Cell reports* (2018) 22(13): 3468-3479]. p21 levels were also augmented in non-healing chronic wounds and local and transient inhibition of p21 by siRNA ameliorated the delayed wound healing in aged mice [Jiang et al., *Wound Repair and Regeneration* (2020) 28(1): 49-60].

Small molecule inhibitors of p21 have been developed for cancer therapy including butyrolactone I (BL) [Sax et al., *Cell cycle (Georgetown, Tex.)* (2002) 1(1): 90-96], LLW10 [Park et al., *Cancer biology & therapy* (2008) 7(12): 2015-2022], sorafenib [Inoue et al., *Cancer biology & therapy* (2011) 12(9): 827-836], and UC2288 [Wettersten et al., *Cancer biology & therapy* (2013) 14(3): 278-285].

DNAzymes

DNAzymes are synthetic, catalytically-active DNA molecules that are able to specifically cleave target mRNA without requiring the involvement of cellular mechanisms such as the RNA-Induced Silencing Complex (RISC). DNAzymes have not been reported in nature and are typically generated by in-vitro selection. Moreover, DNAzymes are diverse structurally and mechanistically, and exhibit diverse secondary structures, metal ion dependencies, and catalysis kinetics.

Of the various classes of DNAzymes, the most studied in the therapeutic context has been the 10-23 class. The 10-23 DNAzymes cleave target RNA molecules, and are functionally classified as antisense, or silencing, DNAzymes. The 10-23 DNAzymes are driven by a central 15-nucleotide long catalytic core, flanked by two regions that are complementary to the target RNA (FIG. 2A). Hybridization of the DNAzyme to its target via the flanking regions enables the catalytic core to attack its target phosphodiester bond (FIG. 2B). Importantly, the mechanism of action of 10-23 DNAzymes makes them suitable for cleaving RNA targets inside living cells as illustrated in FIG. 2C.

The therapeutic potential of DNAzymes has been demonstrated in diverse settings including pre-clinically in a variety of cancer models [Khachigian Cancer Res (2019) 79(5): 879-888], in cardiovascular in-vivo models [Wang et al., Cardiology (2013) 125(3): 192-200], in viral infections [Yao et al. J Virol (2012) 86(16): 8559-8567], in kidney treatment [Huang et al., Sci Rep (2016) 6: 29196] and following myocardial infarction [Xiang et al., J Am Coll Cardiol (2005) 46(3): 536-541].

Additional background art includes:

PCT publication no. WO/2014/174511 provides methods of treating an inflammatory or fibrotic disease in a subject by administering a therapeutically effective amount of an agent (e.g. RNA silencing agent, such as a Ribozyme, DNAzyme or antisense) which down-regulates an activity and/or an amount of Bcl-xL and/or Bcl-w and/or p21, wherein the inflammatory disease is not cancer.

PCT publication no. WO12016/185481 provides methods of targeting a pharmaceutical agent (e.g. cytotoxic agent such a DNAzyme) to a senescent cell for therapeutics or diagnostics.

PCT publication no. WO/2016/135732 provides methods of promoting hair growth by the down-regulation of genes encoding Bcl-2-family proteins and/or p21 (e.g. by utilizing RNA silencing agents, such as a Ribozyme, DNAzyme or antisense).

SUMMARY OF THE INVENTION

According to an aspect of some embodiments of the present invention there is provided a composition of matter comprising a DNAzyme molecule capable of mediating cleavage of p21 mRNA corresponding to SEQ ID NO: 1, wherein the DNAzyme molecule comprises a nucleic acid sequence at least 80% identical to the nucleic acid sequence set forth in any one of SEQ ID NOs: 23, 29, 33-38, 40, 42, 45-48, 53-60, 63-65, 69-74 or 78.

According to an aspect of some embodiments of the present invention there is provided a composition of matter comprising a DNAzyme molecule comprising a nucleic acid sequence as set forth in any one of SEQ ID NOs: 36, 40, 54 or 73.

According to an aspect of some embodiments of the present invention there is provided a pharmaceutical composition comprising the composition of matter of some embodiments of the invention, and a pharmaceutically acceptable carrier.

According to an aspect of some embodiments of the present invention there is provided an article of manufacture comprising the composition of matter of some embodiments of the invention, being packaged in a packaging material and identified in print, in or on the packaging material for use in the treatment of senescence-associated disease or disorder, a cancer or a fibrotic disease or disorder.

According to an aspect of some embodiments of the present invention there is provided a method of eradicating a senescent cell or a cancer cell, the method comprising contacting the senescent cell with the composition of matter of some embodiments of the invention, thereby eradicating the senescent cell or the cancer cell.

According to an aspect of some embodiments of the present invention there is provided a method of treating a senescence-associated disease or disorder in a subject in need thereof, the method comprising administering to the subject a therapeutically effective amount of the composition of matter of some embodiments of the invention, or the pharmaceutical composition of some embodiments of the invention, thereby treating the senescence-associated disease or disorder.

According to an aspect of some embodiments of the present invention there is provided a therapeutically effective amount of the composition of matter of some embodiments of the invention for use in treating a senescence-associated disease or disorder in a subject in need thereof.

According to an aspect of some embodiments of the present invention there is provided a method of treating a cancer in a subject in need thereof, the method comprising administering to the subject a therapeutically effective amount of the composition of matter of some embodiments of the invention, or the pharmaceutical composition of some embodiments of the invention, thereby treating the cancer.

According to an aspect of some embodiments of the present invention there is provided a therapeutically effective amount of the composition of matter of some embodiments of the invention for use in treating cancer in a subject in need thereof.

According to an aspect of some embodiments of the present invention there is provided a method of treating a fibrotic disease or disorder in a subject in need thereof, the method comprising administering to the subject a therapeutically effective amount of the composition of matter of some embodiments of the invention, or the pharmaceutical composition of some embodiments of the invention, thereby treating the fibrotic disease or disorder.

According to an aspect of some embodiments of the present invention there is provided a therapeutically effective amount of the composition of matter of some embodiments of the invention for use in treating a fibrotic disease or disorder in a subject in need thereof.

According to an aspect of some embodiments of the present invention there is provided a method of determining the senolytic effect of a DNAzyme molecule, the method comprising contacting senescent cells with the composition of matter of some embodiments of the invention, wherein a reduction in the number of senescent cells as compared to a number of senescent cells prior to contacting is indicative of the DNAzyme molecule having the senolytic effect.

According to an aspect of some embodiments of the present invention there is provided a method of determining the anti-cancer effect of a DNAzyme molecule, the method comprising contacting cancer cells with the composition of matter of some embodiments of the invention, wherein a reduction in the number of cancer cells as compared to a number of cancer cells prior to contacting is indicative of the DNAzyme molecule having the anti-cancer effect.

According to some embodiments of the invention, the DNAzyme molecule comprises a nucleic acid sequence at least 85% identical to the nucleic acid sequence set forth in any one of SEQ ID NOs: 23, 29, 33-38, 40, 42, 4548, 53-60, 63-65, 69-74 or 78.

According to some embodiments of the invention, the DNAzyme molecule comprises a nucleic acid sequence at least 90% identical to the nucleic acid sequence set forth in any one of SEQ ID NOs: 23, 29, 33-38, 40, 42, 45-48, 53-60, 63-65, 69-74 or 78.

According to some embodiments of the invention, the DNAzyme molecule comprises a nucleic acid sequence at least 95% identical to the nucleic acid sequence set forth in any one of SEQ ID NOs: 23, 29, 33-38, 40, 42, 4548, 53-60, 63-65, 69-74 or 78.

According to some embodiments of the invention, the DNAzyme molecule comprises a nucleic acid sequence at least 98% identical to the nucleic acid sequence set forth in any one of SEQ ID NOs: 23, 29, 33-38, 40, 42, 45-48, 53-60, 63-65, 69-74 or 78.

According to some embodiments of the invention, the DNAzyme molecule comprises a nucleic acid sequence as set forth in any one of SEQ ID NOs: 23, 29, 33-38, 40, 42, 4548, 53-60, 63-65, 69-74 or 78.

According to some embodiments of the invention, the DNAzyme molecule is DNAzyme 1114 comprising a nucleic acid sequence set forth in SEQ ID NO: 40.

According to some embodiments of the invention, the DNAzyme molecule is DNAzyme 1670 comprising a nucleic acid sequence set forth in SEQ ID NO: 54.

According to some embodiments of the invention, the DNAzyme molecule is DNAzyme 985 comprising a nucleic acid sequence set forth in SEQ ID NO: 36.

According to some embodiments of the invention, the DNAzyme molecule is DNAzyme 1987 comprising a nucleic acid sequence set forth in SEQ ID NO: 73.

According to some embodiments of the invention, the DNAzyme molecule comprises no more than 70 nucleotides.

According to some embodiments of the invention, the DNAzyme molecule comprises a catalytic core of no more than 50 nucleotides.

According to some embodiments of the invention, the nucleic acid sequence of the DNAzyme molecule comprises at least one modification.

According to some embodiments of the invention, the modification is in a catalytic core of the DNAzyme molecule.

S According to some embodiments of the invention, the modification is in a binding arm of the DNAzyme molecule.

According to some embodiments of the invention, the modification comprises an insertion, a deletion, a substitution or a point mutation of at least one nucleic acid.

According to some embodiments of the invention, the modification comprises a modification that increases the stability or prevents degradation of the DNA molecule.

According to some embodiments of the invention, the modification comprises an edge-blocker oligonucleotide.

According to some embodiments of the invention, the modification comprises an inverted deoxythymidine (dT) positioned in at least one terminal end of the DNAzyme molecule.

According to some embodiments of the invention, the modification comprises at least one protective group positioned in at least one terminal end of the DNAzyme molecule.

According to some embodiments of the invention, the modification comprises a base modification, a sugar modification and/or an internucleotide linkage modification.

According to some embodiments of the invention, the sugar modification is selected from the group consisting of a 2'-O-methyl (2'-O-Me), a 2'-O-methoxyethyl (2'-O-MOE), a 2'-fluoro (2'-F), a locked nucleic acid (LNA), and a 2'-Fluoroarabinooligonucleotides (FANA).

According to some embodiments of the invention, the internucleotide linkage modification is selected from the group consisting of a phosphorothioate, a chiral phosphorothioate, a phosphorodithioate, a phosphotriester, an aminoalkyl phosphotriester, a methyl phosphonate, an alkyl phosphonate, a chiral phosphonate, a phosphinate, a phosphoramidate, an aminoalkylphosphoramidate, a thionophosphoramidate, a thionoalkylphosphonate, a thionoalkylphosphotriester, a boranophosphate, a phosphodiester, a phosphonoacetate (PACE) and a peptide nucleic acid (PNA).

According to some embodiments of the invention, the DNAzyme molecule comprises a modification that increases the stability or prevents degradation of the DNA molecule.

According to some embodiments of the invention, the modification comprises an edge-blocker oligonucleotide.

According to some embodiments of the invention, the modification comprises an inverted deoxythymidine (dT) positioned at the 3' end of the DNAzyme molecule.

According to some embodiments of the invention, the DNAzyme molecule is attached to a heterologous moiety.

S According to some embodiments of the invention, the heterologous moiety comprises a cell-targeting moiety or a cell-penetrating moiety.

According to some embodiments of the invention, the cell-targeting moiety is an affinity moiety.

According to some embodiments of the invention, the cell-targeting moiety binds to a senescent cell specific cell surface polypeptide.

According to some embodiments of the invention, the cell-targeting moiety binds to a cancer cell specific cell surface polypeptide.

According to some embodiments of the invention, the method is affected in vitro.

According to some embodiments of the invention, the method is affected in vivo.

According to some embodiments of the invention, the senescence-associated disease or disorder is selected from the group of an age-related disease or disorder, a neurological disease or disorder, a neurodegenerative disease or disorder, a cardiovascular disease or disorder, a pulmonary disease or disorder, an inflammatory disease or disorder, an autoimmune disease or disorder, a metabolic disease or disorder, a hepatic disease or disorder, a dermatological disease or disorder, an eye disease or disorder, a fibrotic disease or disorder, a cardiac disease or disorder, a vascular disease or disorder, a renal disease or disorder, and a cancer.

According to some embodiments of the invention, the cancer is a therapy-resistant cancer.

According to some embodiments of the invention, the composition is for systemic, intranasal, inhalation, intracerebroventricular, intrathecal, oral, local injection, intratumoral, or intravenous administration.

According to some embodiments of the invention, the subject is a human subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions,

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 2A: DNAzyme structure—composed of two recognition arms that bind the mRNA sequence and a catalytic core which cleaves the target mRNA. FIG. 2B: Mechanism of action—the DNAzyme binds to the target mRNA via base paring with the recognition arms and the catalytic core (also referred to as catalytic site) is then able to cleave the phosphodiester bond thereby preventing subsequent protein translation. DNAzyme molecules are able to release themselves from the target mRNA following cleavage and recycle to cleave additional mRNA molecules of the same target.

FIG. 2C: Senolytic activity is achieved by degradation and silencing of key senescence survival regulator targets thereby causing senescent cell death.

FIG. 3 illustrates the mRNA sequence for human p21 (i.e. Homo sapiens cyclin dependent kinase inhibitor 1A (CDKN1A), transcript variant 3, mRNA, NM_001291549.3, as set forth in SEQ ID NO: 1).

FIG. 4A: agarose gel electrophoresis of p21 mRNA incubated with several targeting DNAzymes. FIG. 4B: Quantification of FIG. 4A. Scrambled DNAzymes controls were mutated in either the sequence recognition arms or catalytic core (Scr A and B, respectively). FIG. 4C: time and concentration dependent cleavage of the p21 mRNA using the DNAzyme 1670. FIG. 4D: Quantitative analysis of time and concentration dependent cleavage of the p21 mRNA using the DNAzyme 1670.

FIGS. 5A-J illustrate fluorescent microscopy tracking of p21-targeting DNAzyme internalization, p21 mRNA and protein level reduction, and subsequent induction of apoptosis leading to senescent cell elimination. FIGS. 5A-C: Internalization of Cy5-labeled DNAzyme (red) as demonstrated by the appearance of staining in DNAzyme-treated senescent cells (FIG. 5A: untreated. FIG. 5B: treated, FIG. 5C: quantified). FIG. 5D: p21 mRNA downregulation during the first 24 hours following DNAzyme treatment. Specifically, p21 mRNA levels were monitored over 24 hours following treatment with DNAzyme 1670, DNAzyme 985 and their scrambled controls (2000 nM each). FIGS. 5E-G: p21 protein downregulation 48 hours following senescent cell treatment with DNAzyme 1670 (1000 nM) (FIG. 5E: before treatment with DNAzyme, FIG. 5F: after 48 hours incubation with DNAzyme, FIG. 5G: quantified). FIGS. 5H-J: Senescent cell death was quantified by staining for Cleaved Caspase 3/7 (CC3/7) (FIG. 5H: before treatment, FIG. 5I: 72 hours after treatment. FIG. 5J: quantification of CC3/7 over time). Specifically, time course analysis of CC3 activation following DNAzyme 1670 and DNAzyme 985 and their respective scrambled controls (1000 nM each).

FIG. 6A: Bright-field images of senescent human IMR-90 fibroblast cells treated with DNAzyme I 114 or untreated control. FIG. 6B: Viability assay. Of note, killing of senescent cells by p21 mRNA-targeting DNAzymes was effective (of note: scrambled; scr shows no killing), the effect was specific to senescent cells as growing (non-senescent) IMR-90 cells treated with DNAzymes did not undergo cell death. FIG. 6C: Selectivity of DNAzyme 1114 was maintained over a large range of concentrations. FIG. 6D: Effect of DNAzyme 1114 was not cell-lineage dependent as senescent, but not growing cells, from the lung fibroblast and epithelial kidney lineages (WI-38 and REC, respectively) were effectively eliminated.

FIG. 7A: Extension of the DNA binding arm length from 9 to 11 bases increased target mRNA degradation in vitro as seen by quantification of agarose gel electrophoresis. FIG. 7B: Addition of an inverted dT sequence at the 3' end of the DNAzyme increased stability in BALF (bronchalveolar lavage fluid) (compared respective black traces to corresponding red traces).

FIG. 8 illustrates the mRNA sequence for mouse p21 (i.e. NM_007669.5 Mus musculus cyclin-dependent kinase inhibitor 1A (P21) (Cdkn1a), transcript variant 1, mRNA, as set forth in SEQ ID NO: 3).

FIG. 9A: Mouse p21 mRNA in vitro cleavage shown by agarose gel electrophoresis. FIG. 9B: Mouse senescent lung fibroblast (mLF) killing by several DNAzyme sequences (Scr; scrambled sequence control).

FIGS. 10A-D illustrate that p21 DNAzyme reduces fibrosis in vivo. FIG. 10A: Schematic illustration of experimental settings. FIG. 10B: Ashcroft score by histological assessment of lung sections from mice sacrificed at day 21 after bleomycin treatment. FIG. 10C: Average body weight at day 21 following lung fibrosis-inducing bleomycin treatment. FIG. 10D: Survival curves following DNAzyme treatment.

FIG. 11A: Staining of γH2A.X and p53BP1 (DAPI in blue) in DNAzyme 1670 versus scrambled control treated senescent cells (DNAzyme concentration: 1000 nM). Scale bar is 350 μm. FIGS. 11B-C: Time course of γH2A.X and p53BP1 accumulation, respectively, following DNAzyme 1670 and DNAzyme 985 treatment or their respective scrambled controls (1000 nM each). Error bars are SEM.

FIGS. 12A-G illustrate efficacy and selectivity of DNAzymes. FIG. 12A: Growing and senescent cell survival over time following treatment with DNAzyme 1670 and DNAzyme 985 and their respective controls (1000 nM each). Statistical analysis for each DNAzyme comparing senescent with growing cells. FIG. 12B: Dose dependent analysis of DNAzyme 1670. FIG. 12C: Dose dependent analysis of DNAzyme 985. FIG. 12D: DNAzyme-mediated senolytic activity of DNAzyme 1670 and DNAzyme 985 on BJ foreskin fibroblasts. DNAzyme concentration: 625 nM.

FIG. 12E: DNAzyme-mediated senolytic activity of DNAzyme 1670 and DNAzyme 985 on IMR-90 induced to senesce by Replicative Induced Senescence (RIS) (i.e. by replicative exhaustion) and Oncogene Induced Senescence (OIS) (i.e. by H-Ras activation). DNAzyme concentration: 1000 nM. FIGS. 12F-G: DNAzyme-mediated senolytic activity of DNAzyme 1670 on Therapy Induced Senescence (TIS) cancer cells. Combination of DNAzyme 1670 with sub-clinical Etoposide treatment using several cell lines (FIG. 12F). Sub-clinical and clinical chemotherapy doses were determined for the various cell lines used (see chemotherapy and DNAzyme concentrations in the "general materials and experimental procedures" section below). Combination of DNAzyme 1670 with additional chemotherapies in HepG2 cancer cell line (FIG. 12G). Doxo: Doxorubicin, Palbo: Palbociclib. *$P<0.05$; $P<0.01$; *$P<0.001$; ****$P<0.0001$.

FIGS. 13A-O illustrate stability, biodistribution, and safety of a p21-targeting DNAzyme. FIG. 13A: Time dependent stability of unmodified DNAzyme 1670 in PBS, serum and BALF analyzed by agarose gel electrophoresis. FIGS. 13G-O: Blood counts of selected cell types after two-week treatment with DNAzyme 1670.

FIG. 14A: Oxygen saturation in blood. FIG. 14B: Quantification of p21 staining using immunohistochemistry (IHC) by image analysis of lung sections at day 21 (data not shown). FIG. 14C: RNA expression analysis of senescence and senescence associated secretory phenotype (SASP) genes in the post caval lobe of the lung at day 21 (normalized to Rplp0). FIG. 14D: Quantification of collagen content in Masson's Trichrome stained histological sections (of FIG. 14B). FIG. 14E: Quantification of hydroxyproline content from left lung samples at day 21. FIG. 14F: Density quantification of Masson's Trichrome stained sections.

FIG. 15A: Staining and quantification of p21 protein in HepG2 cells following Etoposide alone or together with DNAzyme 1670. Of note, data shows that p21 upregulation is blocked when DNAzyme 1670 is introduced into the cells. FIGS. 15B-C: Evaluation of p21 protein in cell lysate by immunofluorescence (IF) and enzyme-linked immunosorbent assay (ELISA), respectively, following treatment of Etoposide alone or together with scramble or DNAzyme 1670. Of note, data indicates that DNAzyme 1670 can counteract the upregulation in p21 levels.

FIG. 16A: Evaluation of killing efficacy of p21-targeting DNAzymes on HepG2 cells, when introduced together with Etoposide. FIG. 16B: Dose response analysis comparing the effects of scramble versus DNAzyme 1670 on cancer cells (A549), demonstrating that p21 DNAzyme is effective at much lower concentration.

FIG. 17A: Kidney-Body weight ratio in unilateral ureteral obstruction (UUO)-treated mouse as a model of CKD. Of note, treatment with p21-targeting DNAzyme reduced the kidney weight which correlates with disease severity. FIG. 17B: Quantification of fibrotic area in kidney from UUO-treated mice, following treatment with p21-targeting DNAzyme. Of note, treatment with p21-targeting DNAzyme showed significant reduction in the fibrosis.

DESCRIPTION OF SPECIFIC EMBODIMENTS OF THE INVENTION

The present invention, in some embodiments thereof, relates to p21 mRNA targeting DNAzymes and, more particularly, but not exclusively, to the use of same for therapeutics.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Cellular senescence is a stable form of cell-cycle arrest that is associated with chronic inflammation and with various pathologies, including fibrosis, atherosclerosis, osteoarthritis, diabetes and cancer. Cellular senescence is typically controlled by the p53 and p16-retinoblastoma protein (pRB) tumor suppressor pathways. Active p53 establishes the senescence growth arrest in part by inducing the expression of p21, a cyclin-dependent kinase (CDK) inhibitor that, among other activities, suppresses the phosphorylation and, hence, the inactivation of pRB. In normal cells, p21 maintains its genuine signature function as a cell cycle inhibitor and anti-proliferative effector. However, upregulation of p21 enables senescent cells to maintain their viability after damage induction, and allows their retention within tissues. Increased expression of p21 is evident in various age-related conditions associated with cellular senescence. The p21 protein (and its mRNA) is therefore an attractive target for diseases such as cancer therapy and other cellular senescence related diseases.

While reducing the present invention to practice, the present inventors have generated p21 mRNA-targeting DNAzyme molecules which mediate efficient and specific p21 RNA interference. Accordingly, these DNAzyme molecules can be used in therapeutics of senescent-associated diseases and cancer.

Figure 1:
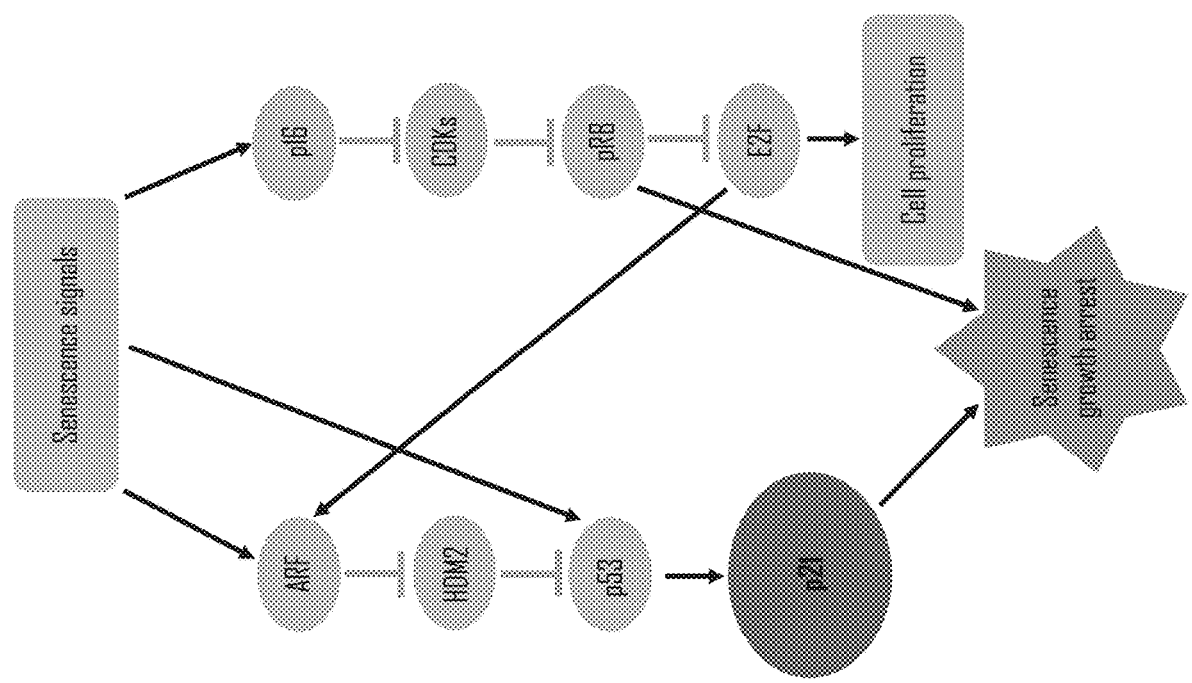
FIG. 1 is a schematic illustration of the p53- and p16-pRB pathways controlling cellular senescence [modified from Campisi, J. and Di Fagagna, FDA, Nature reviews Molecular cell biology (2007) 8(9), 729-740]. Abbreviations are as follows: alternate-reading-frame protein (ARF), HDM2 (an E3 ubiquitin ligase), cyclin-dependent kinases (CDKs), p16-retinoblastoma protein (pRB).
Figure 2A:
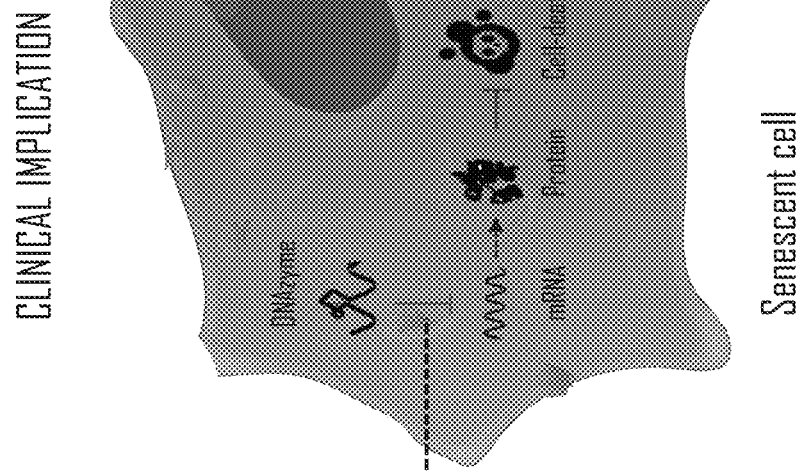
FIGS. 2A-C is a schematic illustration of DNAzyme-mediated senolytic activity.
Figure 2B:
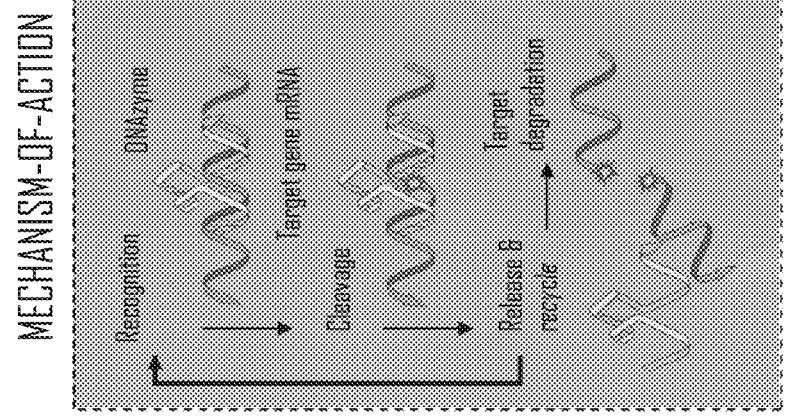
Figure 2C:
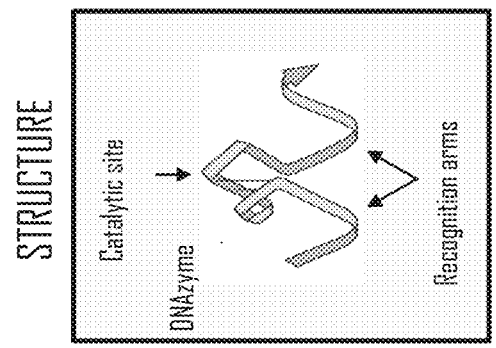
Figure 4A:
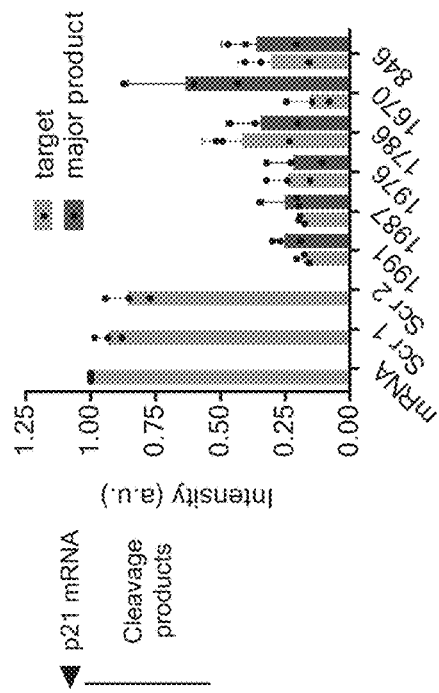
FIGS. 4A-D illustrate in vitro cleavage of human p21 mRNA by DNAzymes (also designated as Dz or Dnz).
Figure 4B:
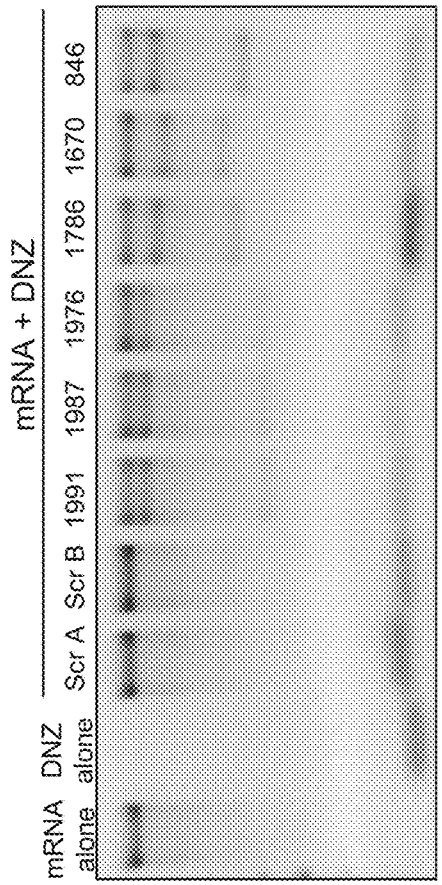
Figure 4C:
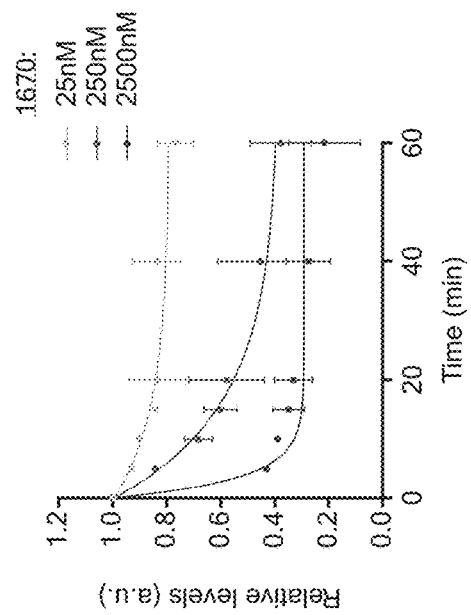
Figure 4D:
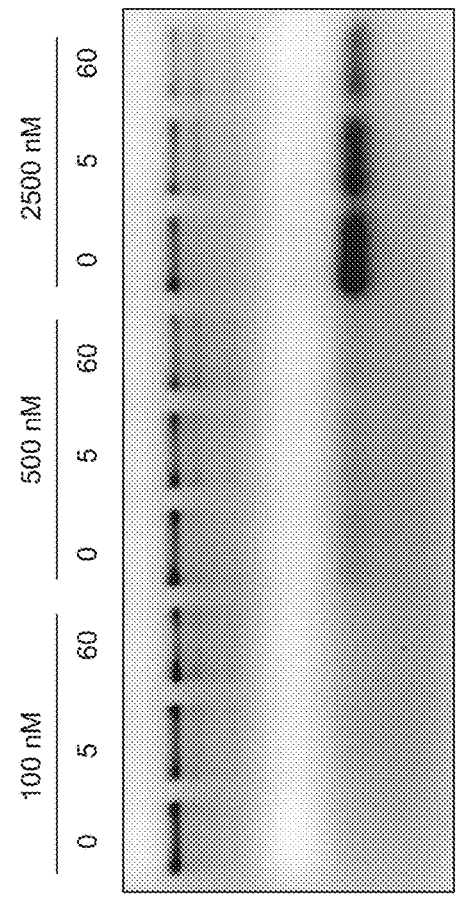
Figure 11A:
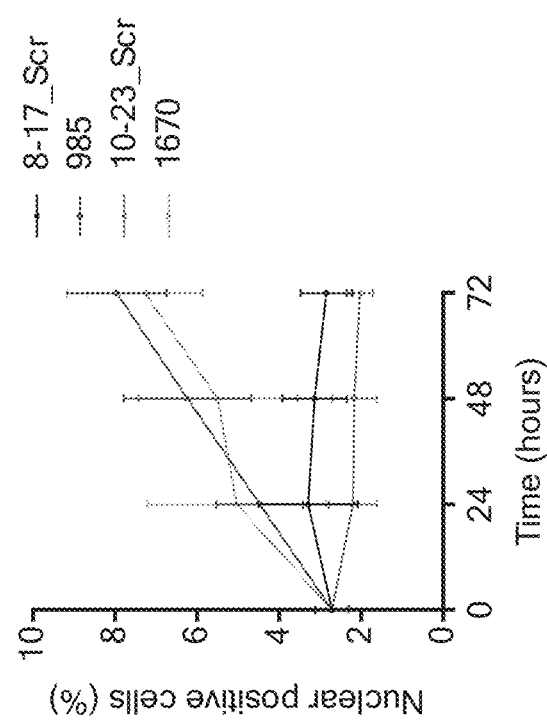
FIGS. 11A-C illustrate the mechanism of action of p21-targeting DNAzymes.
Figure 11B:
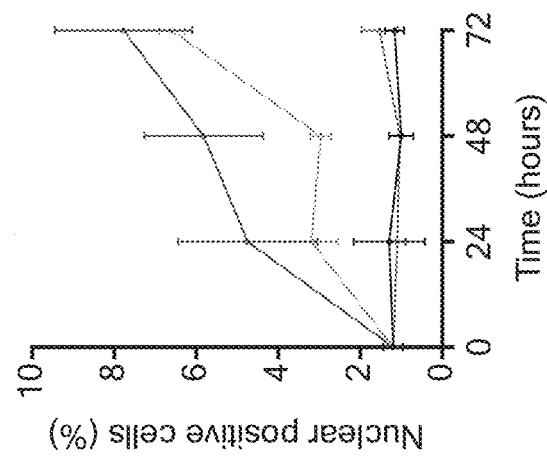
Figure 11C:
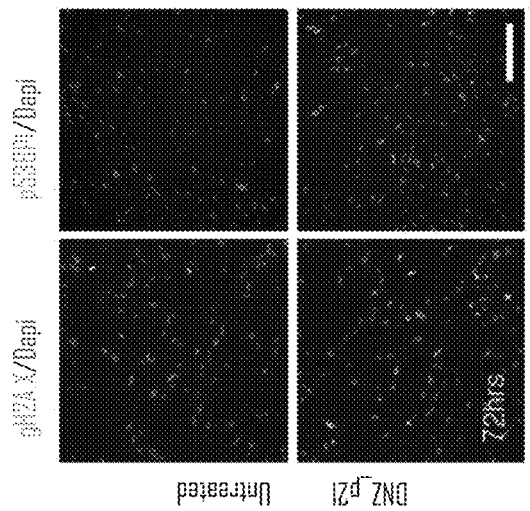
Figure 13C:
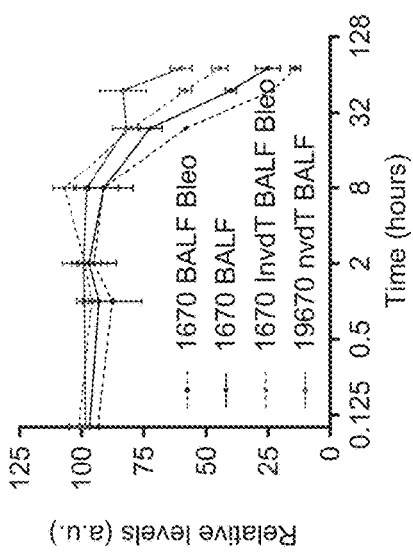
FIG. 13C: Stability of DNAzyme 1670 in PBS and BALF from naive and bleomycin treated (at day 7 post treatment) mice with or without a 3' inverted-dT modification.
Figure 13B:
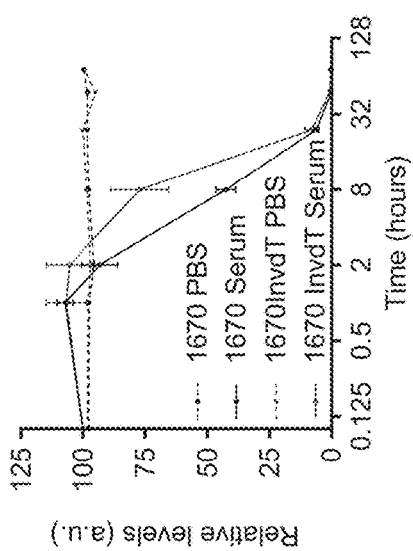
FIG. 13B: Stability of DNAzyme 1670 in PBS and serum, with or without a 3' inverted-dT modification. Error bars are SEM.
Figure 13A:
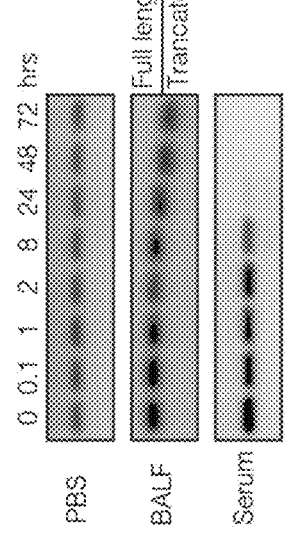

Specifically, the present inventors have designed and generated 72 DNAzymes, of these 34 were capable of specifically targeting and mediating cleavage of p21 mRNA (see Table 2 and FIGS. 4A-B). The cleavage by DNAzymes could be controlled by the dosage and incubation time as shown in FIGS. 4C-D. The present inventors illustrated that the DNAzymes were internalized by senescence cells, reduced p21 mRNA and protein levels therein and lead to senescence cell death (see Table 2, and FIGS. 5A-J). Treatment of senescence cells with p21-targeting DNAzymes lead to cell death by apoptosis following accumulation of DNA damage (FIGS. 11A-C). It was further illustrated that cell death was not dependent on cell type and was specific to senescence cells i.e. non-senescence cells did not undergo cell death (see FIGS. 6A-D and 12A-D). Treatment efficacy was illustrated in replicative induced senescence (RIS), in oncogene induced senescence (OIS) as well as in therapy induced senescence (TIS), in the latter case in combination with sub-clinical chemotherapy doses (FIGS. 12E-G). In order to increase stability (e.g. in the bronchoalveolar lavage fluid (BALF) and in the serum) and improve efficiency, the DNAzyme binding arms were extended by 1-2 nucleotides or an inverted dT sequence was added to the 3' end of the DNAzyme (FIGS. 7A-B and 13B-C). These p21-targeting DNAzyme were illustrated to be stable and safe in an in vivo mice model (FIGS. 13A-O).

Figure 17B:
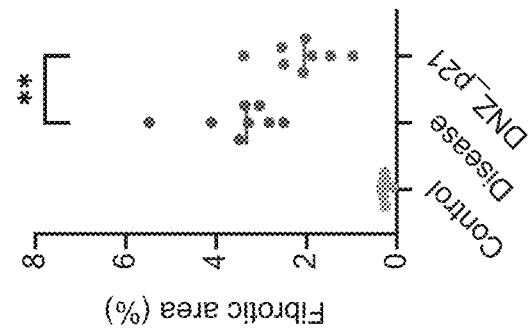
FIGS. 17A-B illustrate p21-targeting DNAzyme in chronic kidney disease model (CKD).
Figure 17A:
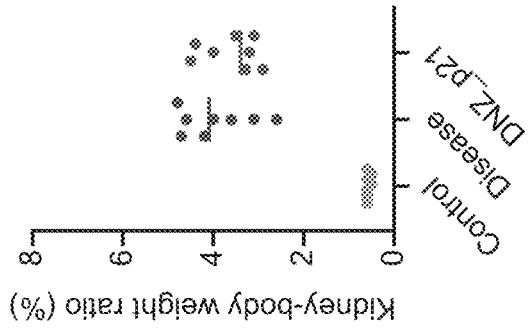

In order to test the in-vivo efficacy of DNAzymes in a mouse model, the present inventors further devised DNAzymes which specifically target mouse p21 mRNA (see Table 3). These DNAzymes were shown to specifically target mouse p21 mRNA (see FIG. 9A), were senolytic i.e. lead to senescence cell death (see FIG. 9B) and reduced fibrosis in-vivo as evident in an idiopathic pulmonary fibrosis (IPF) model illustrating lower fibrotic score, higher body weight, increased survival, improved oxygen saturation in the blood, as well as lower collagen and hydroxyproline levels (see FIGS. 10B-D, 14A and 14D-E, respectively). Similar results were demonstrated in a chronic kidney disease model (CKD) illustrating that p21-targeting DNAzymes (DNZ_p21) significantly reduced the weight of the obstructed kidney and reduced the fibrotic extent (FIGS. 17A-B, respectively). Taken together, these results emphasize the therapeutic potential of p21-mRNA targeting DNAzymes for therapy, such as senolytics.

Thus, according to one aspect of the present invention there is provided a composition of matter comprising a DNAzyme molecule capable of mediating cleavage of p21 mRNA corresponding to SEQ ID NO: 1, wherein the DNAzyme molecule comprises a nucleic acid sequence at least 80% identical to the nucleic acid sequence set forth in any one of SEQ ID NOs: 23, 29, 33-38, 40, 42, 45-48, 53-60, 63-65, 69-74 or 78.

The term "p21" also known as "cyclin-dependent kinase inhibitor 1" refers to the mRNA product of the p21 gene (CDKN1A) having a sequence as set forth in SEQ ID NO: 1 (GeneBank Accession No. NM_001291549.3) and homologs, orthologs and variants thereof. Additional exemplary p21 mRNAs include, but are not limited to, those provided in GeneBank Accession Nos. NM_000389.5, NM_001220777.2, NM_001220778.2, NM_001374509.1, NM_001374510.1, NM_001374511.1, NM_001374512.1, NM_001374513.1 and NM_078467.3, or variants thereof.

The term "DNAzyme" (also referred to as a "DNA enzyme" or "deoxynbozyme") as used herein refers to a DNA molecule that has complementarity in a substrate binding domain or region to a ribonucleic acid (RNA) substrate and is capable of catalyzing a modification (such as a cleavage) of the nucleic acid substrate. Typically, the complementarity functions to allow sufficient hybridization of the DNAzyme molecule to the substrate at a target region to allow the intermolecular cleavage of the substrate to occur thereby functionally inactivating it. The cleavage can occur via two optional mechanisms: (i) intrinsic catalytic activity of the DNAzyme (ii) recruitment of RNAse H to the hybridization site, leading to cleavage of the target RNA.

Thus, the term "mediating cleavage" refers to direct catalytic activity (i.e. by the DNAzyme molecule) or indirect catalytic activity (i.e. by an enzyme recruited by the DNAzyme molecule) which leads to cleavage and RNA interference of the p21 mRNA.

The term "target RNA" or "target region of an RNA" refers to an RNA molecule (e.g. an mRNA molecule encoding a p21 gene product) that is a target for downregulation. Similarly, the phrase "target site" refers to a sequence within a target RNA (e.g. within the p21 mRNA sequence) that is "targeted" for cleavage mediated by the DNAzyme molecule that contains sequences within its substrate binding domains that are complementary to the target site (as discussed below).

According to one embodiment, silencing of the p21 mRNA (e.g. cleavage of the p21 mRNA) results in downregulation of mRNA and/or protein expression levels.

According to one embodiment, down regulating p21 expression level refers to the absence of p21 mRNA and/or protein, as detected by RT-PCR or Western blot/Immunofluorescent staining, respectively.

According to other embodiment, down regulating p21 expression level refers to a decrease in the level of p21 mRNA and/or protein, as detected by RT-PCR or Western blot/Immunofluorescent staining, respectively. The reduction may be by at least a 10%, at least 20%, at least 30%, at least 40%, at least 50%, at least 60%, at least 70%, at least 80%, at least 90%, at least 95% or at least 99% reduction, as compared to the expression level of p21 prior to the treatment.

Down regulation of expression may be either transient or permanent.

The term "nucleic acid" as used herein generally refers to a molecule (single-stranded or double-stranded oligomer or polymer) of DNA or RNA or a derivative, mimic or analog thereof, comprising a nucleobase. A nucleobase includes, for example, a naturally occurring purine or pyrimidine base found in DNA (e.g., an adenine "A", a guanine "G", a thymine "T", or a cytosine "C") or a naturally occurring purine or pyrimidine base found in RNA (e.g., an adenine "A", a guanine "G", an uracil "U" or a cytosine "C"). The term "nucleic acid" encompasses the terms "oligonucleotide" and "polynucleotide" and "nucleotides", each as a subgenus of the term "nucleic acid". The term "nucleic acid" further includes nucleic acids derived from synthetic polynucleotide and/or oligonucleotide molecules composed of naturally occurring bases, sugars, and covalent internucleoside linkages (e.g., backbone), as well as synthetic polynucleotides and/or oligonucleotides having non-naturally occurring portions, which function similarly to respective naturally occurring portions, as further discussed herein below.

According to one embodiment, the DNAzyme molecule is synthetic. As used herein "synthetic" refers to a non-natural molecule.

The DNAzyme typically comprises a pair of binding arms which are complementary to binding regions on the nucleic acid substrate (e.g. p21 mRNA). Each binding arm of the DNAzyme comprises a number of nucleotides to permit sufficient bonding between the DNAzyme and its substrate to facilitate DNAzyme activity (i.e. cleavage of the p21 substrate at the target cleavage site). The binding arms may be the same or different lengths. Furthermore, the binding arms may comprise modified nucleotides, including modified bases, backbone, sugars and/or linkages to the extent that such modifications do not have an adverse effect on binding activity of the DNAzyme to the substrate (e.g. p21 mRNA). Such modifications are discussed below.

For example, each binding arm may comprise 5-25 nucleotides, 5-10 nucleotides, 10-15 nucleotides, 15-20 nucleotides or 20-25 nucleotides (e.g. deoxyribonucleotides or ribonucleotides). According to one embodiment, each binding arm comprises at least about 5, 6. 7, 8, 9, 10, 11, 12, 13, 14, 15, 16, 17, 18, 19, 20, 21, 22, 23, 24 or 25 nucleotides (e.g. deoxyribonucleotides or ribonucleotides). According to a specific embodiment, each binding arm comprises at least about 8-10 nucleotides, e.g. 9 nucleotides (e.g. deoxyribonucleotides or ribonucleotides).

According to a specific embodiment, each of the binding arms of the DNAzyme molecule comprises no more than 6, 7, 8, 9, 10, 11, 12, 13, 14 or 15 nucleotides (e.g. deoxyribonucleotides or ribonucleotides).

As mentioned, the DNAzyme targets a nucleic acid-based substrate comprising binding regions which are essentially complementary to the binding arms of the DNAzyme, and which hybridize with the binding arms of the DNAzyme. The binding regions need not be fully complementary with the binding arms of the DNAzyme, provided that they hybridize sufficiently with the DNAzyme such that the catalytic activity of the DNAzyme is not adversely affected (e.g. exhibit at least about 70%, 80%, 85%, 9) %, 95% 97% or 99% complementarity). Typically, the cleavage site is within a target region of the substrate situated between the binding regions. The terminal 5'- and 3' ends of the target region are each linked to a binding region at the appropriate corresponding terminus (e.g. 5' to 3') of the binding arm.

As used herein, the terms "complementarity" and "complementary" refer to a nucleic acid that can form one or more hydrogen bonds with another nucleic acid sequence by either traditional Watson-Crick or other non-traditional types of interactions. In reference to the nucleic molecules of the presently disclosed subject matter, the binding free energy for a nucleic acid molecule with its complementary sequence is sufficient to allow the relevant function of the nucleic acid to proceed, in some embodiments, binding with specificity by substrate binding domains of a DNAzyme of some embodiments of the invention such that the catalytic domain of the DNAzyme is brought in to close enough proximity with a target sequence to permit catalytic cleavage of the target sequence. The degree of complementarity between the substrate binding domains of the DNAzyme and the target region of a RNA (e.g. a p21 mRNA) can vary, but no more than by what is required in order to permit the DNAzyme to cleave or mediate cleavage (e.g. by RNase H) of the target region. Determination of binding free energies for nucleic acid molecules to determine percent complementarity is well known in the art. See e.g., Freier et al., 1986; Turner et al., 1987.

As used herein, the phrase "percent complementarity" refers to the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). The terms "100% complementary", "fully complementary", and "perfectly complementary" indicate that all of the contiguous residues of a nucleic acid sequence can hydrogen bond with the same number of contiguous residues in a second nucleic acid sequence.

The DNAzyme additionally comprises a catalytic domain (also referred to as catalytic core) between the binding arms, generally in the form of a loop, which includes single-stranded DNA, and may optionally include double-stranded regions. The terminal 5'- and 3' ends of the catalytic domain are each linked to a binding arm at the appropriate corresponding terminus of the binding arm (e.g. 5' to 3'). The catalytic region may incorporate modified nucleotides, including modified bases, backbone, sugars and/or linkages to the extent that such modifications do not have an adverse effect on catalytic activity (i.e. cleavage activity) of the DNAzyme, such modifications are discussed below.

The size of the catalytic domain in each DNAzyme may include, for example, 5-100 nucleotides, e.g. 5-10 nucleotides, 10-20 nucleotides, 20-30 nucleotides, 30-40 nucleotides, 40-50 nucleotides, 50-75 nucleotides or 75-100 nucleotides (e.g. deoxyribonucleotides or ribonucleotides). According to one embodiment, the catalytic domain comprises at least about 5, 10, 15, 20, 25, 30, 35, 40, 45 or 50 nucleotides (e.g. deoxyribonucleotides or ribonucleotides). According to a specific embodiment, the catalytic domain comprises at least about 10, 11, 12, 13, 14, 15, 16, 17, 18, 19, 20, 21, 22, 23, 24, 25, 30, 35, 40, 45 or 50 nucleotides (e.g. deoxyribonucleotides or ribonucleotides).

According to a specific embodiment, the catalytic domain of the DNAzyme molecule comprises no more than 14, 15, 16, 17, 18, 19, 20, 21, 22, 23, 24, 25, 30, 35, 40, 45 or 50 nucleotides (e.g. deoxyribonucleotides or ribonucleotides).

Exemplary DNAzyme catalytic domains which may be used in accordance with some embodiments of the invention, include, but are not limited to, the catalytic cores of lanthanide-dependent DNAzymes such as Ce13d, Lu12 and Tm7; the catalytic cores of magnesium-dependent DNAzymes such as 17E and 10-23, 8-17: the catalytic cores of uranyl-specific DNAzymes such as 39E and EHg0T; the catalytic cores of lead-dependent DNAzymes such as GR5; and functionally equivalent DNAzyme catalytic cores derived from any of these which exhibit a high degree of sequence identity. e.g. at least about 80%, 85%, 90%, 95% or 99%. The term "functionally equivalent" refers to DNAzyme catalytic cores which retain the ability to cleave the DNAzyme substrate or to recruit RNase H. Additional catalytic cores of DNAzymes which may be used in accordance with some embodiments of the invention include e.g. Bipartite I and Bipartite II (discussed in Feldman and Sen. *Journal of molecular biology* (2001) 313(2): 283-294, incorporated herein by reference), 10MD5 and I-R3 (discussed in Hollenstein, *Molecules* (2015) 20(11): 20777-20804, and in Zhou et al. *Theranostics.* 2017; 7(4): 1010-1025, both incorporated herein by reference).

According to one embodiment, the DNAzyme is a 10-23 type DNAzyme (i.e. comprises the 10-23 catalytic core).

The term "10-23" refers to a general DNAzyme model (discussed in detail in Sontoro and Joyce, *PNAS* (1997) 94 (9):4262-4266, incorporated herein by reference). DNAzymes of the 10-23 model typically have a catalytic domain of 15 nucleotides, which are flanked by two substrate binding domains. The catalytic domain of 10-23 DNAzymes typically comprises the sequence ggctagctacaacga (SEQ ID NO: 88). The DNAzyme 10-23 typically cleaves mRNA strands that contain an unpaired purine-pyrimidine pair. The length of the substrate binding domains of 10-23 DNAzymes is variable and may be of either equal length or variable length. According to one embodiment, the length of the substrate binding domains ranges between 6 and 14 nucleotides, e.g. between 8 and 12 nucleotides (e.g. 7, 8, 9, 10, 11, 12 nucleotides, e.g. 9 nucleotides).

According to one embodiment, the DNAzyme is a 8-17 type DNAzyme (i.e. comprises the 8-17 catalytic core).

The term "8-17" refers to a general DNAzyme model (discussed in detail in Sontoro and Joyce, PNAS (1997) 94

(9):4262-4266, incorporated herein by reference). DNAzymes of the 8-17 model typically have a catalytic domain of 14 nucleotides, which are flanked by two substrate binding domains. The catalytic domain of 8-17 DNAzymes typically comprises the sequence TCCGAGCCGGACGA (SEQ ID NO: 89). The length of the substrate binding domains of 8-17 DNAzymes is variable and may be of either equal length or variable length. According to one embodiment, the length of the substrate binding domains ranges between 6 and 14 nucleotides, e.g. between 8 and 12 nucleotides (e.g. 7, 8, 9, 10, 11, 12 nucleotides, e.g. 8 nucleotides).

According to one embodiment, the DNAzyme catalytic domain comprises the 16.2-11 catalytic core: GTGACCC-CUUG (SEQ ID NO: 90); the 9-86 catalytic core; UCAUGCAGCGCUAGUGUC (SEQ ID NO: 91); the 12-91 catalytic core; UGAUGCAGCGCAUGUGUC (SEQ ID NO: 92); the FR17_6 catalytic core; AAGCAGUUAA-GAC (SEQ ID NO: 93) or the Bipartite I or Bipartite II catalytic core; AAGGAGGTAGGGGTTCCGCTCC (SEQ ID NO: 94).

According to one embodiment, the DNAzyme is an inducible DNAzyme. Exemplary inducible DNAzymes are MNAzymes (discussed in detail in Mokany et al., *Journal of the American Chemical Society* (2010) 132(3): 1051-1059, incorporated herein by reference). Specifically, MNAzymes are multicomponent complexes that produce amplified "output" signals in response to specific "input" signals. Multiple oligonucleotide partzymes assemble into active MNAzymes only in the presence of an input assembly facilitator such as a target nucleic acid. Once formed, MNAzymes catalytically modify a generic substrate, generating an amplified output signal that heralds the presence of the target while leaving the target intact.

According to a specific embodiment, the DNAzyme molecule comprises 20-80 nucleotides, e.g. 20-70 nucleotides, e.g. 20-60 nucleotides, e.g. 20-50 nucleotides, e.g. 20-40 nucleotides, e.g. 20-30 nucleotides, e.g. 30-50 nucleotides, e.g. 30-40 nucleotides (e.g. deoxyribonucleotides or ribonucleotides). According to a specific embodiment, the DNAzyme molecule comprises at least about 20, 25, 30, 31, 32, 33, 34, 35, 36, 37, 38, 39, 40, 45, 50, 55, 60, 65, 70 or 75 nucleotides (e.g. deoxyribonucleotides or ribonucleotides).

According to a specific embodiment, the DNAzyme molecule comprises no more than 20-80 nucleotides, e.g. 20-70 nucleotides, e.g. 20-60 nucleotides, e.g. 20-50 nucleotides, e.g. 20-40 nucleotides, e.g. 20-30 nucleotides, e.g. 30-50 nucleotides, e.g. 30-40 nucleotides (e.g. deoxyribonucleotides or ribonucleotides). According to a specific embodiment, the DNAzyme molecule comprises no more than e.g. 30, 31, 32, 33, 34, 35, 36, 37, 38, 39, 40, 41, 42, 43, 44, 45, 50, 55, 60, 65, 70, 75 or 80 nucleotides (e.g. deoxyribonucleotides or ribonucleotides).

In some embodiments, one or more mutations or modifications within the catalytic domain of the DNAzyme molecule can be carried out to increase the catalytic activity of the DNAzyme molecule (e.g. by insertion, deletion, substitution or point mutation of nucleic acids). It is to be understood that any mutation or modification, e.g., within the substrate binding domain sequences or catalytic domain sequence, must not adversely impact the molecule's ability to induce catalysis (e.g. cleave) the specific substrate, i.e. p21.

According to a specific embodiment, the modification comprises the insertion, deletion, substitution or point mutation of 1-10 nucleotides, e.g. 1-8 nucleotides, e.g. 1-6 nucleotides, e.g. 1-5 nucleotides, e.g. 1-4 nucleotides, e.g. 1-3 nucleotides, or e.g. 1-2 nucleotides in the catalytic domain of the DNAzyme.

According to a specific embodiment, the modification comprises the insertion, deletion, substitution or point mutation of 1, 2, 3, 4, 5, 6, 7, 8, 9, 10 nucleotides. e.g. 1 or 2 nucleotides, in the catalytic domain of the DNAzyme.

Additionally or alternatively, the DNAzyme molecule may be modified to alter the length of the substrate binding domains of the DNAzyme molecule. The substrate binding domains of the DNAzyme molecule have binding specificity for and associate with a complementary sequence of bases within a target region of a substrate nucleic acid sequence (as discussed above). Methods of altering the length of the recognition domains are known in the art and include direct synthesis and PCR, for example.

Alteration of the length of the recognition domains of a DNAzyme molecule can have a desirable effect on the binding specificity of the DNAzyme molecule. For example, an increase in the length of the substrate binding domains can increase binding specificity between the DNAzyme molecule and the complementary base sequences of a target region in a substrate polynucleotide (i.e. p21). In addition, an increase in the length of the substrate binding domains can also increase the affinity with which the DNA molecule binds to the polynucleotide substrate. In various embodiments, these altered substrate binding domains in the DNAzyme molecule confer increased binding specificity and affinity between the DNAzyme molecule and its substrate (i.e. p21), however, it may decrease catalytic efficiency of the DNAzyme. Therefore, one of skill in the art will appreciate that alteration of the length of the recognition domains is a balance of optimal binding and catalytic activity.

According to a specific embodiment, the modification comprises the addition of 1-10 nucleotides, e.g. 1-8 nucleotides, e.g. 1-6 nucleotides, e.g. 1-5 nucleotides, e.g. 1-4 nucleotides, e.g. 1-3 nucleotides, or e.g. 1-2 nucleotides to the substrate binding domain (i.e. binding arm) of the DNAzyme.

According to a specific embodiment, the modification comprises the addition of 1, 2, 3, 4, 5, 6, 7, 8, 9, 10 nucleotides, e.g. l or 2 nucleotides, to the substrate binding domain (i.e. binding arm) of the DNAzyme.

Additionally or alternatively, the substrate binding domains of the DNAzyme molecule may be modified to improve binding to the p21 mRNA target. Accordingly, the modification may comprise the insertion, deletion, substitution or point mutation of 1, 2, 3, 4, 5, 6, 7, 8, 9, 10 nucleotides, e.g. 1 or 2 nucleotides, in the substrate binding domain of the DNAzyme.

According to a specific embodiment, the DNAzyme molecule comprises a nucleic acid sequence at least 80%, 81%, 82%, 83%, 84%, 85%, 86%, 87%, 88%, 89%, 90%, 91%, 92%, 93%, 94%, 95%, 96%, 97%, 98%, 99% or 100% identical to the nucleic acid sequence set forth in any one of SEQ ID NOs: 23, 29, 33-38, 40, 42, 45-48, 53-60, 63-65, 69-74 or 78.

As used herein, "sequence identity" or "identity" in the context of two nucleic acid sequences includes reference to the residues in the two sequences which are the same when aligned.

Identity (e.g., percent homology) can be determined using any homology comparison software, including for example, the BlastN software of the National Center of Biotechnology Information (NCBI) such as by using default parameters.

According to some embodiments of the invention, the identity is a global identity, i.e., an identity over the entire nucleic acid sequences of the invention and not over portions thereof.

The degree of homology or identity between two or more sequences can be determined using various known sequence comparison tools. Following is a non-limiting description of such tools which can be used along with some embodiments of the invention.

When starting with a polynucleotide sequence and comparing to other polynucleotide sequences the EMBOSS-6.0.1 Needleman-Wunsch algorithm (available from emboss (dot)sourceforge(dot)net/apps/cvs/emboss/apps/needle(dot)html) can be used.

According to some embodiment, determination of the degree of homology further requires employing the Smith-Waterman algorithm (for protein-protein comparison or nucleotide-nucleotide comparison).

According to one embodiment, the DNAzyme molecule comprises a nucleic acid sequence at least 80% identical to the nucleic acid sequence set forth in any one of SEQ ID NOs: 23, 29, 33-38, 40, 42, 45-48, 53-60, 63-65, 69-74 or 78.

According to one embodiment, the DNAzyme molecule comprises a nucleic acid sequence at least 85% identical to the nucleic acid sequence set forth in any one of SEQ ID NOs: 23, 29, 33-38, 40, 42, 45-48, 53-60, 63-65, 69-74 or 78.

According to one embodiment, the DNAzyme molecule comprises a nucleic acid sequence at least 90% identical to the nucleic acid sequence set forth in any one of SEQ ID NOs: 23, 29, 33-38, 40, 42, 45-48, 53-60, 63-65, 69-74 or 78.

According to one embodiment, the DNAzyme molecule comprises a nucleic acid sequence at least 95% identical to the nucleic acid sequence set forth in any one of SEQ ID NOs: 23, 29, 33-38, 40, 42, 45-48, 53-60, 63-65, 69-74 or 78.

According to one embodiment, the DNAzyme molecule comprises a nucleic acid sequence at least 98% identical to the nucleic acid sequence set forth in any one of SEQ ID NOs: 23, 29, 33-38, 40, 42, 45-48, 53-60, 63-65, 69-74 or 78.

According to one embodiment, the DNAzyme molecule comprises a nucleic acid sequence at least 99% identical to the nucleic acid sequence set forth in any one of SEQ ID NOs: 23, 29, 33-38, 40, 42, 45-48, 53-60, 63-65, 69-74 or 78.

According to one embodiment, the DNAzyme molecule comprises a nucleic acid sequence set forth in any one of SEQ ID NOs: 23, 29, 33-38, 40, 42, 45-48, 53-60, 63-65, 69-74 or 78.

According to a specific embodiment, the DNAzyme molecule is DNAzyme 1114 comprising a nucleic acid sequence at least 80%, 81%, 82%, 83%, 84%, 85%, 86%, 87%, 88%, 89%, 90%, 91%, 92%, 93%, 94%, 95%, 96%, 97%, 98%, 99% or 100% identical to the nucleic acid sequence set forth set forth in SEQ ID NO: 40.

According to a specific embodiment, the DNAzyme molecule is DNAzyme 1114 comprising a nucleic acid sequence set forth in SEQ ID NO: 40.

According to a specific embodiment, the DNAzyme molecule is DNAzyme 1670 comprising a nucleic acid sequence at least 80%, 81%, 82%, 83%, 84%, 85%, 86%, 87%, 88%, 89%, 90%, 91%, 92%, 93%, 94%, 95%, 96%, 97%, 98%, 99% or 100% identical to the nucleic acid sequence set forth set forth in SEQ ID NO: 54.

According to a specific embodiment, the DNAzyme molecule is DNAzyme 1670 comprising a nucleic acid sequence set forth in SEQ ID NO: 54.

According to a specific embodiment, the DNAzyme molecule is DNAzyme 985 comprising a nucleic acid sequence at least 80%, 81%, 82%, 83%, 84%, 85%, 86%, 87%, 88%, 89%, 90%, 91%, 92%, 93%, 94%, 95%, 96%, 97%, 98%, 99% or 100% identical to the nucleic acid sequence set forth set forth in SEQ ID NO: 36.

According to a specific embodiment, the DNAzyme molecule is DNAzyme 985 comprising a nucleic acid sequence set forth in SEQ ID NO: 36.

According to a specific embodiment, the DNAzyme molecule is DNAzyme 1987 comprising a nucleic acid sequence at least 80%, 81%, 82%, 83%, 84%, 85%, 86%, 87%, 88%, 89%, 90%, 91%, 92%, 93% 94%, 95%, 96%, 97%, 98%, 99% or 100% identical to the nucleic acid sequence set forth set forth in SEQ ID NO: 73.

According to a specific embodiment, the DNAzyme molecule is DNAzyme 1987 comprising a nucleic acid sequence set forth in SEQ ID NO: 73.

Various modifications to DNAzyme molecules can be made to enhance the utility of these molecules. Such modifications can enhance affinity for the nucleic acid target, increase activity, increase specificity, increase stability and decrease degradation (e.g. in the presence of nucleases), increase shelf-life, enhance half-life and/or improve introduction of such DNAzyme molecules to the target site (for example, to enhance penetration of cellular membranes, confer the ability to recognize and bind to targeted cells, and enhance cellular uptake), as discussed in further detail below.

According to one embodiment, the DNAzyme molecule comprises a modification selected from an insertion, deletion, substitution or point mutation of a nucleic acid, as long as the molecule retains at least about 80%, 85%, 90%, 95%, 99% or 100% of its the biological activity (i.e. silencing activity, e.g. mediating catalytic activity on the p21 substrate).

It will be appreciated that insertions, deletions, substitutions or point mutations can be generated using methods that produce random or specific alterations. These mutations or modifications can, for example, change the length of, or alter the nucleotide sequence of, a loop, a spacer region or the substrate binding domain (e.g. binding arm of the DNAzyme as discussed above) or add one or more non-nucleotide moieties to the molecule to, for example, increase stability and/or decrease degradation.

The DNAzyme molecule of the invention is optimally stable within cells until translation of the target RNA has been inhibited long enough to reduce the levels of the undesirable protein. This period of time varies between hours to days depending upon the cell type and state (e.g. senescence). Although DNAzyme molecules as described herein are considered advantageous over RNA based molecules in that DNAzymes are less sensitive to degradation, in some embodiments it is desirable to further increase stability and nuclease resistance of the DNAzymes. Furthermore, when RNA based molecules are utilized, these may be modified to increase their stability and nuclease resistance.

According to one embodiment, the modification is selected from the group consisting of a nucleobase modification, a sugar modification, and an internucleotide linkage modification (e.g. phosphorus-modified internucleotide linkage), as is broadly described herein under.

According to one embodiment, the DNAzyme molecule comprises one or more chemical modifications.

Any chemical modification can be applied to the DNAzyme molecule of the invention as long as the molecule retains at least about 80%, 85%, 90%, 95%, 99% or 100% of its the biological activity (i.e. silencing activity, e.g. mediating catalytic activity on the p21 substrate).

According to one embodiment, the DNAzyme molecule includes at least one base (e.g. nucleobase) modification or substitution.

As used herein, "unmodified" or "natural" bases include the purine bases adenine (A) and guanine (G) and the pyrimidine bases thymine (T), cytosine (C), and uracil (U). "Modified" bases include but are not limited to other synthetic and natural bases, such as: 5-methylcytosine (5-me-C); 5-hydroxymethyl cytosine; xanthine; hypoxanthine; 2-aminoadenine; 6-methyl and other alkyl derivatives of adenine and guanine: 2-propyl and other alkyl derivatives of adenine and guanine: 2-thiouracil, 2-thiothymine, and 2-thiocytosine: 5-halouracil and cytosine; 5-propynyl uracil and cytosine: 6-azo uracil, cytosine, and thymine: 5-uracil (pseudouracil); 4-thiouracil; 8-halo, 8-amino, 8-thiol, 8-thioalkyl, 8-hydroxyl, and other 8-substituted adenines and guanines: 5-halo, particularly 5-bromo, 5-trifluoromethyl, and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Additional modified bases include those disclosed in: U.S. Pat. No. 3,687,808; Kroschwitz, J. I., ed. (1990), "The Concise Encyclopedia Of Polymer Science And Engineering," pages 858-859, John Wiley & Sons: Englisch et al. (1991), "Angewandte Chemie," International Edition, 30, 613; and Sanghvi, Y. S., "Antisense Research and Applications." Chapter 15, pages 289-302, S. T. Crooke and B. Lebleu, eds., CRC Press, 1993. Such modified bases are particularly useful for increasing the binding affinity of the oligomeric compounds of the invention. These include 5-substituted pyrimidines, 6-azapyrimidines, and N-2, N-6, and O-6-substituted purines, including 2-aminopropyladenine, 5-propynyluracil, and 5-propynylcytosine, 5-methylcytosine substitutions have been shown to increase nucleic acid duplex stability by 0.6-1.2° C. (Sanghvi, Y. S. et al. (1993). "Antisense Research and Applications," pages 276-278, CRC Press, Boca Raton), and are presently preferred base substitutions, even more particularly when combined with 2'-O-methoxyethyl sugar modifications. Additional base modifications are described in Deleavey and Damha, *Chemistry and Biology* (2012) 19; 937-954, incorporated herein by reference.

According to one embodiment, the modification is in the backbone (i.e. in the internucleotide linkage and/or the sugar moiety).

Sugar modification of nucleic acid molecules have been extensively described in the art (see PCT International Publication Nos. WO 92/07065, WO 93/15187, WO 98/13526, and WO 97/26270; U.S. Pat. Nos. 5,334,711; 5,716,824; and U.S. Pat. No. 5,627,053; Perrault et al., 1990: Pieken et al., 1991; Usman & Cedergren, 1992: Beigelman et al., 1995; Karpeiskv et al., 1998; Eamshaw & Gait, 1998; Verma & Eckstein, 1998; Burlina et al, 1997; all of which are incorporated herein by reference). Such publications describe general methods and strategies to determine the location of incorporation of sugar, base, and/or phosphate modifications and the like into nucleic acid molecules without modulating catalysis. Exemplary sugar modifications include, but are not limited to, 2'-modified nucleotide, e.g., a 2'-deoxy, 2'-fluoro (2'-F), 2'-deoxy-2'-fluoro, 2'-O-methyl (2'-O-Me), 2'-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), 2'-Fluoroarabinooligonucleotides (2'-F-ANA), 2'-O—N-methylacetamido (2'-O-NMA), 2'-NH2 or a locked nucleic acid (LNA). Additional sugar modifications are described in Deleavey and Damha, *Chemistry and Biology* (2012) 19: 937-954, incorporated herein by reference.

Thus, for example, oligonucleotides can be modified to enhance their stability and/or enhance biological activity by modification with nuclease resistant groups, for example, the DNAzyme molecule of the invention can include 2'-O-methyl, 2'-fluorine, 2'-O-methoxyethyl, 2'-O-aminopropyl, 2'-amino, and/or phosphorothioate linkages. Inclusion of locked nucleic acids (LNA), e.g. inclusion of nucleic acid analogues in which the ribose ring is "locked" by a methylene bridge connecting the 2'-0 atom and the 4'-C atom, ethylene nucleic acids (ENA), e.g., 2'-4'-ethylene-bridged nucleic acids, and certain nucleobase modifications such as 2-amino-A, 2-thio (e.g., 2-thio-U), G-clamp modifications, can also increase binding affinity to the target. The inclusion of pyranose sugars in the oligonucleotide backbone can also decrease endonucleolytic cleavage. The binding arms may further include peptide nucleic acid (PNA) in which the deoxribose (or ribose) phosphate backbone in the DNA is replaced with a polyamide backbone, or may include polymer backbones, cyclic backbones, or acyclic backbones. The binding regions may incorporate sugar mimetics, and may additionally include protective groups, particularly at terminal ends thereof, to prevent undesirable degradation (as discussed below).

Exemplary internucleotide linkage modifications include, but are not limited to, phosphorothioate, chiral phosphorothioate, phosphorodithioate, phosphotriester, aminoalkyl phosphotriester, methyl phosphonate, alkyl phosphonate (including 3'-alkylene phosphonates), chiral phosphonate, phosphinate, phosphoramidate (including 3'-amino phosphoramidate), aminoalkylphosphoramidate, thionophosphoramidate, thionoalkylphosphonate, thionoalkylphosphotriester, boranophosphate (such as that having normal 3'-5' linkages, 2'-5' linked analogues of these, and those having inverted polarity wherein the adjacent pairs of nucleoside units are linked 3'-5' to 5'-3' or 2'-5' to 5'-2'), boron phosphonate, phosphodiester, phosphonoacetate (PACE), morpholino, amidate carbamate, carboxymethyl, acetamidate, polyamide, sulfonate, sulfonamide, sulfamate, formacetal, thioformacetal, alkylsilyl, substitutions, peptide nucleic acid (PNA) and/or threose nucleic acid (TNA). Various salts, mixed salts, and free acid forms of the above modifications can also be used. Additional internucleotide linkage modifications are described in Deleavey and Damha, *Chemistry and Biology* (2012) 19: 937-954; and Hunziker & Leumann, 1995 and De Mesmaeker et al., 1994, both incorporated herein by reference.

According to a specific embodiment, the modification comprises modified nucleoside triphosphates (dN*TPs).

According to one embodiment, the modification comprises an edge-blocker oligonucleotide.

According to a specific embodiment, the edge-blocker oligonucleotide comprises a phosphate, an inverted deoxythymidine (dT) and an amino-C7.

According to a specific embodiment, the modification comprises an inverted deoxythymidine (dT) positioned in at least one terminal end of the DNAzyme molecule. For example, an inverted dT can be incorporated at the 3'-end of an oligo, leading to a 3'-3' linkage which inhibits both degradation by 3' exonucleases and extension by DNA polymerases.

According to a specific embodiment, the DNAzyme molecule comprises DNAzyme 985 (set forth in SEQ ID NO: 36), DNAzyme 1114 (set forth in SEQ ID NO: 40), DNAzyme 1670 (set forth in SEQ ID NO: 54), or DNAzyme 1987 (set forth in SEQ ID NO: 73), wherein the DNAzyme comprises an inverted deoxythymidine (dT) positioned at the 3' end of the DNAzyme molecule.

According to one embodiment, the DNAzyme molecule is modified to comprise one or more protective group, e.g. 5' and/or 3'-cap structures.

As used herein, the phrase "cap structure" is meant to refer to chemical modifications that have been incorporated at either terminus of the oligonucleotide (see e.g., U.S. Pat. No. 5,998,203, incorporated by reference herein). These terminal modifications protect the nucleic acid molecule from exonuclease degradation, and can help in delivery and/or localization within a cell. The cap modification can be present at the 5'-terminus (5'-cap) or at the 3'-terminal (3'-cap), or can be present on both termini. In non-limiting examples: the 5'-cap is selected from the group comprising inverted abasic residue (moiety); 4'5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage: threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety: 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

In some embodiments, the 3'-cap is selected from a group comprising inverted deoxynucleotide, such as for example inverted deoxythymidine, 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate: 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety: 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non-bridging methylphosphonate and 5'-mercapto moieties (see generally Beaucage & Iyer, 1993; incorporated by reference herein).

A DNAzyme molecule can be further modified by including a 3' cationic group, or by inverting the nucleoside at the terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3' end of the oligonucleotide. Even small alkyl chains, aryl groups, or heterocyclic conjugates or modified sugars (D-ribose, deoxyribose, glucose etc.) can block 3'-5'-exonucleases.

According to one embodiment, the 5'-terminus can be blocked with an aminoalkyl group, e.g., a 5'-O-alkylamino substituent. Other 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5' end of the oligonucleotide. Even small alkyl chains, aryl groups, or heterocyclic conjugates or modified sugars (D-ribose, deoxyribose, glucose etc.) can block 3'-5'-exonucleases.

In one embodiment, the DNAzyme molecule includes a modification that improves targeting. Examples of modifications that target DNAzymes to particular cell types include carbohydrate sugars such as galactose, N-acetylgalactosamine, mannose; vitamins such as folates; other ligands such as RGDs and RGD mimics; and small molecules including naproxen, ibuprofen or other known protein-binding molecules (further discussed hereinbelow).

According to one embodiment, the DNAzyme molecule of the invention can be constructed using chemical synthesis and/or enzymatic ligation reactions using procedures known in the art (as discussed in detail below). For example, the polynucleotide can be chemically synthesized using naturally occurring nucleotides or variously modified nucleotides designed to increase the biological stability of the molecules or to increase the physical stability of the duplex formed between the polynucleotide and target nucleic acids, e.g., phosphorothioate derivatives and acridine substituted nucleotides can be used (as discussed in detail hereinabove).

The DNAzyme molecule designed according to the teachings of the present invention can be generated according to any oligonucleotide synthesis method known in the art, including both enzymatic syntheses and solid-phase syntheses. Various different mechanisms of oligonucleotide synthesis have been disclosed in for example, U.S. Pat. Nos. 4,659,774, 4,816,571, 5,141,813, 5,264.566, 4,959,463, 5,428,148, 5,554,744, 5,574,146, 5,602,244, each of which is incorporated herein by reference.

According to one embodiment, chemical synthesis can be achieved by the diester method, triester method, polynucleotides phosphorylase method and by solid-phase chemistry. These methods are discussed in further detail below.

Diester Method:

The diester method was the first to be developed to a usable state. The basic step is the joining of two suitably protected deoxynucleotides to form a dideoxynucleotide containing a phosphodiester bond.

Triester Method:

The main difference between the diester and triester methods is the presence in the latter of an extra protecting group on the phosphate atoms of the reactants and products. The phosphate protecting group is usually a chlorophenyl group, which renders the nucleotides and polynucleotide intermediates soluble in organic solvents. Therefore purification's are done in chloroform solutions. Other improvements in the method include (i) the block coupling of trimers and larger oligomers, (ii) the extensive use of high-performance liquid chromatography for the purification of both intermediate and final products, and (iii) solid-phase synthesis.

Polynucleotide Phosphorylase Method:

This is an enzymatic method of DNA synthesis that can be used to synthesize many useful oligonucleotides. Under controlled conditions, polynucleotide phosphorylase adds predominantly a single nucleotide to a short oligonucleotide. Chromatographic purification allows the desired single adduct to be obtained. At least a trimer is required to start the procedure, and this primer must be obtained by some other method. The polynucleotide phosphorylase method works and has the advantage that the procedures involved are familiar to most biochemists.

Solid-Phase Methods:

Drawing on the technology developed for the solid-phase synthesis of polypeptides, it has been possible to attach the initial nucleotide to solid support material and proceed with the stepwise addition of nucleotides. All mixing and washing steps are simplified, and the procedure becomes amenable to automation. These syntheses are now routinely carried out using automatic nucleic acid synthesizers. Equipment and reagents for executing solid-phase synthesis are commercially available from, for example, Applied Biosystems.

Phosphoramidite chemistry has become by far the most widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

Recombinant Methods:

Recombinant methods for producing nucleic acids in a cell are well known to those of skill in the art and can be implemented in cases where the DNAzyme molecule does not comprise chemical modifications. These include the use of vectors, plasmids, cosmids, and other vehicles for delivery a nucleic acid to a cell, which may be the target cell or simply a host cell (to produce large quantities of the desired RNA molecule). Alternatively, such vehicles can be used in the context of a cell free system so long as the reagents for generating the RNA molecule are present. Such methods include those described in Sambrook, 2003, Sambrook, 2001 and Sambrook, 1989, which are hereby incorporated by reference.

Any other means for such synthesis may also be employed; the actual synthesis of the oligonucleotides is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Maryland; Perbal, B. (1988), "A Practical Guide to Molecular Cloning," John Wiley & Sons, New York: and Gait, M. J., ed. (1984), "Oligonucleotide Synthesis"; utilizing solid-phase chemistry, e.g. cyanoethyl phosphoramidite followed by deprotection, desalting, and purification by, for example, an automated trityl-on method or HPLC.

According to one embodiment, the DNAzyme molecule is attached to a heterologous moiety that is selected to improve stability, increase half-life (e.g. in the serum, BALF), distribution, cellular uptake, crossing of the blood brain barrier (BBB) or to target the DNAzyme molecule to a cell of interest. Thus, the DNAzyme molecule may be modified to include a non-nucleotide moiety, as discussed in detail below.

As used herein the phrase "heterologous moiety" refers to a sequence which does not form an intrinsic part of the DNAzyme molecule. Preferably, the heterologous moiety does not affect the biological activity of the DNAzyme, i.e. silencing activity, e.g. mediating catalytic activity on the p21 substrate.

According to one embodiment, the heterologous moiety is a proteinaceous moiety.

According to one embodiment, the heterologous moiety is a non-proteinaceous moiety.

According to one embodiment, the heterologous moiety is a cell-targeting moiety.

As used herein, the expression "cell-targeting moiety" refers to any substance that binds to a molecule expressed or presented on the target cell of interest, preferably in a specific manner, e.g. not expressed/presented on other cell types or expressed/presented at higher levels than in other cell types. According to a specific embodiment, the molecule expressed or presented on the target cell of interest is a polypeptide, e.g. receptor. This binding specificity allows the delivery of the DNAzyme molecule, which is attached to the cell-targeting moiety, to the cell, tissue or organ that expresses or presents the molecule (e.g. polypeptide, glycoprotein, receptor, ligand). In this way, a DNAzyme attached to a cell-targeting moiety will be directed specifically to the target cells when administered to a subject (e.g. human) or contacted in vitro with a population of cells of different types.

The phrase "target cell" or "target cell of interest" refers to a cell that expresses a target RNA (e.g. p21 mRNA) and into which a DNAzyme molecule is intended to be introduced. A target cell is, in some embodiments, a cell in a subject. According to a specific embodiment, the cell is a senescent cell. According to a specific embodiment, the cell is a cancerous cell.

The term "senescent cell" as used herein refers to a cell that exhibits cell cycle arrest, generally during the G1 transition of the cell cycle or in few cases in G2, elicited by replicative exhaustion due to telomere attrition or in response to stresses such as DNA damage, chemotherapeutic drugs, or aberrant expression of oncogenes. The term senescent cell includes a cell which has entered senescence or is at the onset of senescence, i.e. a pre-senescent cell.

The term "cancerous cell" or "cancer cell" as used herein refers to cells associated with phenotypes such uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor, such cells may exist locally within a subject (e.g. solid tumor), alternatively, cancer cells may circulate in the blood stream or in the lymphatic system as independent cells, for example, leukemic cells or lymphoma cells, respectively (e.g. non-solid tumor such as a hematologic malignancy), or may be dispersed throughout the body (e.g. metastasis).

A cell-targeting moiety according to the present invention may show a Kd for the target (the molecule expressed or presented on the target cell of interest, e.g. polypeptide, e.g. receptor, expressed on the senescent cell) of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M or greater.

According to one embodiment, the cell-targeting moiety is a synthetic component.

According to one embodiment, the cell-targeting moiety is a nanoparticle capable of binding an antigen, a receptor or other protein, or non-proteinaceous membrane compounds of a target cell. A wide range of nanocarriers for nucleic acid drug delivery may be used in accordance with the present invention, including but not limited to, cationic polymers (for example, polyethylenimine), dendrimers, CPPs (for example, MPG-8, PepFect6, RVG-9R, and Xentry-KALA), calcium phosphate nanoparticles, exosomes, and lipid nanoparticles (LNPs), as discussed in Roberts et al. *Nature Reviews Drug Discovery* (2020), incorporated herein by reference.

According to one embodiment, the cell-targeting moiety is a sugar (for example, N-acetylgalactosamine (GalNAc)).

According to one embodiment, the cell-targeting moiety is an affinity binding moiety, i.e. any naturally occurring or artificially produced molecule or composition which binds to a specific molecule (e.g. antigen) with a higher affinity than to a non-specific molecule (e.g. antigen).

It should be noted that the affinity can be quantified using known methods such as, Surface Plasmon Resonance (SPR) (described in Scarano S, Mascini M, Turner A P, Minunni M. Surface plasmon resonance imaging for affinity-based biosensors. Biosens Bioelectron. 2010, 25: 957-66) using e.g. a captured or immobilized monoclonal antibody (MAb) format to minimize contribution of avidity, and can be calculated using, e.g., a dissociation constant, Kd, such that a lower Kd reflects a higher affinity.

An affinity binding moiety typically has a binding affinity (KD) of at least about 2 to about 200 M (i.e. as long as the binding is specific i.e., no background binding).

According to a specific embodiment, the affinity binding moiety is an aptamer or a lectin.

According to a specific embodiment, the affinity binding moiety is an antibody or an antibody fragment.

The term "antibody" as used in this invention includes intact molecules as well as functional fragments thereof, such as Fab, Fab', F(ab')2, Fv, linear antibodies, scFv antibodies, and multispecific antibodies formed from antibody fragments that are capable of binding to the antigen. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains: (5) Single chain antibody ("SCA"), a genetically engineered molecule containing the variable region of the light chain and the variable region of the heavy chain, linked by a suitable polypeptide linker as a genetically fused single chain molecule; (6) CDR peptide is a peptide coding for a single complementarity-determining region (CDR); and (7) Single domain antibodies (also called nanobodies), a genetically engineered single monomeric variable antibody domain which selectively binds to a specific antigen. Nanobodies have a molecular weight of only 12-15 kDa, which is much smaller than a common antibody (150-160 kDa).

According to one embodiment, the cell-targeting moiety binds to a senescent cell-specific cell surface polypeptide (e.g. marker of senescence with extracellular epitope/s). Exemplary senescent cell specific cell surface polypeptides include, but are not limited to, HSP90B1, DNAJB4, PI4K2A, DBN1, PRKCSH, SPTBN1, NPM1, ITGA3, CD58/ICAM1, ARMCX-3, B2MG, DCR2, DEP1, LANCL1, NOTCH3, PLD3, VPS26A, NTAL, EBP50, STX4, VAMP3, CD9, NOTCH1, OXIDIZED FORM OF MEMBRANE-BOUND VIMENTIN, TNFRSF10B, PLAUR, TSPAN2, ACTN1, ARL4C, OSBPL3, PHLDA3, THBS1, DPP4, REEP5, SQRDL, STOM, CAV1, SVIL, MGST1, WFS1, PTGS1, MBOAT7, PCYOX1, CNN1, F3, STIM1, SYNGR1, SLC6A15, THBD, TFPI2, NRG1, FLRT3, VAPB, SLC20A1, NTSR1, GPR68, ECSCR, NIM1, MCCC1, OSMR, TMEM132A, TNC, PCCA, L1CAM, PCDH9, TGM2, ANPEP, CCT7, HK2.

According to one embodiment, the cell-targeting moiety binds to a cancer cell-specific cell surface polypeptide (e.g. tumor antigen). Exemplary tumor antigens include, but are not limited to, A33, BAGE, Bcl-2, B cell maturation antigen (BCMA), BCR-ABL, β-catenin, cancer testis antigens (CTA e.g. MAGE-1, MAGE-A2/A3 and NY-ESO-1), CA 125, CA 19-9, CA 50, CA 27.29 (BR 27.29), CA 15-3, CD5, CD19, CD20, CD21, CD22, CD33, CD37, CD45, CD123, CEA, c-Met, CS-1, cyclin B1, DAGE, EBNA, EGFR, ELA2, ephrinB2, estrogen receptor, FAP, ferritin, folate-binding protein, GAGE, G250/CA IX, GD-2, GM2, gp75, gp100 (Pmel 17), HA-1, HA-2, HER-2/neu, HM1.24, HPV E6, HPV E7, hTERT, Ki-67, LRP, mesothelin, mucin-like cancer-associated antigen (MCA), MUC1, p53, PR1, PRAME, PRTN3, RHAMM (CD168), WT-1.

According to one embodiment, the DNAzyme molecule of some embodiments of the invention comprises at least one cell-penetrating moiety.

As used herein the term "cell-penetrating moiety" refers to a compound which mediates transfer of a substance (e.g. DNAzyme) from an extracellular space to an intracellular compartment of a cell (e.g. senescent cell). Cell-penetrating moieties shuttle a linked substance (e.g., a DNAzyme molecule) into the cytoplasm or to the cytoplasmic space of the cell membrane.

Cell-penetrating moieties include, without being limited to, lipidic moieties (i.e. naturally occurring or synthetically produced lipids) such as a cholesterol moiety (Letsinger et al, Proc. Natl. Acid. Sci. USA, 199, 86, 6553-6556), cholic acid (Manoharan et al, Biorg. Med. Chem. Let., 1994 4 1053-1060), a thioether, e.g., beryl-S-tritylthiol (Manoharan et al, Ann. N.Y. Acad. Sci., 1992, 660, 306-309; Manoharan et al, Biorg. Med. Chem. Let., 1993, 3, 2765-2770), a thiocholesterol (Oberhauser et al, Nucl. Acids Res., 1992, 20, 533-538), an aliphatic chain, e.g., dodecandiol or undecyl residues (Saison-Behmoaras et al. EMBO J, 1991, 10, 11 11-1118; Kabanov et al, FEBS Lett., 1990, 259, 327-330: Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-Hphosphonate (Manoharan et al, Tetrahedron Lett., 1995, 36, 3651-3654; Shea et al, Nucl. Acids Res., 1990, 18, 3777-3783), a polyamine or a polyethylene glycol chain (Manoharan et al., Nucleosides and Nucleotides, 1995, 14, 969-973), or adamantane acetic acid (Manoharan et al., Tetrahedron Lett., 1995, 36, 3651-3654), a palmityl moiety (Mishra et ai, Biochim. Biophys. Acta, 1995, 1264, 229-237), an octadecylamine or hexylamino-carbonyloxycholesterol moiety (Crooke et al., J. Pharmacol. Exp. Ther., 1996, 277, 923-937), a steroid, a sphingosine, a ceramide, or a fatty acid moiety. The fatty acid moiety can be, e.g., any fatty acid which contains at least eight carbons. For example, the fatty acid can be, e.g., a nonanoyl ($C_9$); capryl ($C_{10}$): undecanoyl ($C_{11}$); lauroyl ($C_{12}$); tridecanoyl (C.sub.13); myristoyl (C.sub.14); pentadecanoyl (C.sub.15): palmitoyl (C.sub.16): phytanoyl (methyl substituted C.sub.16); heptadecanoyl (C.sub.17); stearoyl (C.sub.18); nonadecanoyl (C.sub.19); arachidoyl (C.sub.20): henieco-sanoyl (C.sub.21); behenoyl (C.sub.22); trucisanoyl (C.sub.23); or a lignoceroyl (C.sub.24) moiety. The cell-penetrating moiety can also include multimers (e.g., a composition containing more than one unit) of octyl-glycine, 2-cyclohexylalanine, or benzolylphenylalanine. The cell-penetrating moiety contains an unsubstituted or a halogen-substituted (e.g., chloro) biphenyl moiety. Substituted biphenyls are associated with reduced accumulation in body tissues, as compared to compounds with a non-substituted biphenyl. Reduced accumulation in bodily tissues following administration to a subject is associated with decreased adverse side effects in the subject.

According to one embodiment, the cell-penetrating moiety is a peptide (CPP). Suitable peptides typically include short (typically less than 30 amino acids) amphipathic or cationic peptide fragments that are typically derived from naturally occurring protein translocation motifs, as in the case of HIV-TAT (transactivator of transcription protein), Penetratin 1 (homeodomain of the Drosophila Antennapedia protein) and Transportan (a chimeric peptide consisting of part of to the galanin neuropeptide fused to the wasp venom, mastoparan), or are based on polymers of basic amino acids (e.g. arginine and lysine). Additional examples are provided in Roberts et al. Nature Reviews Drug Discovery (2020), incorporated herein by reference.

It will be appreciated that the cell-targeting moiety may be used for cell penetration and likewise the cell-penetrating moiety may be used for cell targeting. Thus, it is to be understood that the moieties discussed herein above may be used interchangeably.

The DNAzyme molecule and the heterologous moiety (e.g. cell-targeting moiety or the cell-penetrating moiety) may be coupled directly or indirectly via an intervening moiety or moieties, such as a linker, a bridge, or a spacer moiety or moieties.

According to one embodiment, the DNAzyme molecule and the heterologous moiety (e.g. cell-targeting moiety or the cell-penetrating moiety) may be directly coupled. Alternatively, according to another embodiment, the moiety may be linked by a connecting group. The terms "connecting group", "linker", "linking group" and grammatical equivalents thereof are used herein to refer to an organic moiety that connects two parts of a compound.

The heterologous moiety (e.g. cell-targeting moiety or the cell-penetrating moiety) can be attached to any nucleotide in the DNAzyme molecule, but it can be preferably coupled through the 3' terminal nucleotide and/or 5' terminal nucleotide. An internal conjugate may be attached directly or indirectly through a linker to a nucleotide at a 2' position of the ribose group, or to another suitable position.

Thus, the heterologous moiety (e.g. cell-targeting moiety or the cell-penetrating moiety) can be attached to any nucleotide within the DNAzyme molecule as long as the silencing activity (e.g. mediating catalytic activity) of the DNAzyme is not compromised.

Any of the above described moieties (e.g. cell-targeting moiety or the cell-penetrating moiety) may be selected by the skilled person taking into consideration the target tissue, the target cell, the administration route, the pathway that the DNAzyme is expected to follow, etc.

According to one embodiment, when the moiety (e.g. cell-targeting moiety or the cell-penetrating moiety) is a peptide or peptide product, it may be subjected to in-vitro modification (e.g., PEGylation, lipid modification, etc.) so as to confer the peptide's amino acid sequence with stability (e.g., against protease activities) and/or solubility (e.g., within a biological fluid such as blood, digestive fluid) while preserving its biological activity and prolonging its half-life.

When the DNAzyme molecule is coupled to a heterologous moiety, synthesis can be carried out using standard procedures in organic synthesis. The skilled person will appreciate that the exact steps of the synthesis will depend on the exact structure of the molecule which has to be synthesized. For instance, if the molecule is attached to the heterologous moiety through its 5' end, then the synthesis is usually carried out by contacting an amino-activated oligonucleotide and a reactive activated heterologous moiety.

According to one embodiment, the DNAzyme is coupled to a heterologous moiety and to a protecting group (e.g. the heterologous moiety is coupled to the 5' end of the DNAzyme and the protecting group to the 3' end, or vice versa).

According to one embodiment, there is provided a method of eradicating a senescent cell or a cancer cell with the composition of matter of some embodiments of the invention.

The DNAzyme molecules of the invention are to be provided to the cells i.e., target cells (e.g. senescent cells, cancer cells) of the present invention in vivo (i.e., inside the organism or the subject), in vitro or ex vivo (e.g., in a tissue culture). It will be appreciated that the DNAzyme molecule may be provided directly to the target cells, or alternatively may be administered to a tissue or organ comprising the target cells, or to a subject in need of eradication of senescent cells or cancer cells.

The prior art teaches of a number of delivery strategies which can be used to efficiently deliver oligonucleotides into a wide variety of cell types [see, for example, Jääskeläinen et al. Cell Mol Biol Lett. (2002) 7(2):236-7; Gait, Cell Mol Life Sci. (2003) 60(5):844-53; Martino et al. J Biomed Biotechnol. (2009) 2009:410260: Grijalvo et al. Expert Opin Ther Pat. (2014) 24(7):801-19: Falzarano et al, Nucleic Acid Ther. (2014) 24(1):87-100: Shilakari et al. Biomed Res Int. (2014) 2014; 526391; Prakash et al. Nucleic Acids Res. (2014) 42(13):8796-807 and Asseline et al. J Gene Med. (2014) 16(7-8):157-65].

According to one embodiment, the present techniques relate to introducing the DNAzyme molecules using transient DNA or DNA-free methods (such as RNA transfection).

According to one embodiment, the DNAzyme molecule is delivered as a "naked" oligonucleotide, i.e. without the additional delivery vehicle. According to one embodiment, the "naked" oligonucleotide comprises a chemical modification to facilitate its tissue delivery (e.g. utilizing inverted nucleotides, phosphorothioate linkages, or integration of locked nucleic acids, as discussed above).

Any method known in the art for RNA or DNA transfection can be used in accordance with the present teachings, such as, but not limited to microinjection, electroporation, lipid-mediated transfection e.g. using liposomes, or using cationic molecules or nanomaterials (discussed below, and further discussed in Roberts et al. Nature Reviews Drug Discovery (2020) 19: 673-694, incorporated herein by reference).

According to one embodiment, and as mentioned above, in cases where the DNAzyme molecule does not comprise a chemical modification it may be administered to the target cell (e.g. senescent cell) as part of an expression construct. In this case, the DNAzyme molecule is ligated in a nucleic acid construct (also referred to herein as an "expression vector") under the control of a cis-acting regulatory element (e.g. promoter) capable of directing an expression of the DNAzyme in the target cells (e.g. senescent cell) in a constitutive or inducible manner.

The expression constructs of the present invention may also include additional sequences which render it suitable for replication and integration in eukaryotes (e.g., shuttle vectors). Typical cloning vectors contain transcription and translation initiation sequences (e.g., promoters, enhances) and transcription and translation terminators (e.g., polyadenylation signals). The expression constructs of the present invention can further include an enhancer, which can be adjacent or distant to the promoter sequence and can function in up regulating the transcription therefrom. Polyadenylation sequences can also be added to the expression constructs of the present invention in order to increase the efficiency of expression.

In addition to the embodiments already described, the expression constructs of the present invention may typically contain other specialized elements intended to increase the level of expression of cloned nucleic acids or to facilitate the identification of cells that carry the DNAzyme. The expression constructs of the present invention may or may not include a eukaryotic replicon.

The nucleic acid construct may be introduced into the target cells (e.g. senescent cells or cancer cells) of the present invention using an appropriate gene delivery vehicle/method (transfection, transduction, etc.) and an appropriate expression system. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Additionally or alternatively, lipid-based systems may be used for the delivery of constructs or DNAzyme molecules into the target cells (e.g. senescent cells or cancer cells) of the present invention. Lipid bases systems include, for example, liposomes, lipoplexes and lipid nanoparticles (LNPs).

Liposomes include any synthetic (i.e., not naturally occurring) structure composed of lipid bilayers, which enclose a volume. Liposomes include emulsions, foams, micelles, insoluble monolayers, liquid crystals, phospholipid dispersions, lamellar layers and the like. The liposomes may be prepared by any of the known methods in the art [Monkkonen, J. et al., 1994, J. Drug Target, 2:299-308: Monkkonen, J. et al., 1993, Calcif. Tissue Int., 53:139-145: Lasic D D., Liposomes Technology Inc., Elsevier, 1993, 63-105. (chapter 3); Winterhalter M, Lasic D D. Chem Phys Lipids, 1993 September; 64(1-3):35-43]. Any method known in the art can be used to incorporate a polynucleotide agent (e.g. DNAzyme molecule) into a liposome. For example, the polynucleotide agent (e.g. DNAzyme molecule) may be encapsulated within the liposome. Alternatively, it may be adsorbed on the liposome's surface. Other methods that may be used to incorporate a pharmaceutical agent into a liposome of the present invention are those described by Alfonso et al., [The science and practice of pharmacy, Mack Publishing, Easton Pa $19^{th}$ ed., (1995)] and those described by Kulkami et al., [J. Microencapsul. 1995, 12 (3) 22946].

Furthermore, lipid nanoparticles (LNPs), also known as stable nucleic acid lipid particles, may be used in accordance with the present teachings. These are typically liposomes that contain ionizable lipid, phosphatidylcholine, cholesterol and PEG-lipid conjugates, as discussed in Roberts et al. Nature Reviews Drug Discovery (2020), incorporated herein by reference.

The lipid bases systems (e.g. liposomes) used in the methods of the present invention may cross the blood barriers. Thus, according to an embodiment the lipid bases systems (e.g. liposomes) of the present invention do not comprise a blood barrier targeting polysaccharide (e.g. mannose) in their membrane portion. In order to determine lipid bases systems (e.g. liposomes) that are especially suitable in accordance with the present invention a screening assay can be performed such as the assays described in U.S. Pat. Appl. No. 20040266734 and U.S. Pat. Appl. No. 20040266734: and in Danenberg el al., Journal of cardiovascular pharmacology 2003, 42:671-9; Circulation 2002, 106:599-605; Circulation 2003, 108:2798-804.

For in vivo therapy, the composition of matter of some embodiments of the invention comprising a DNAzyme molecule is administered to the subject per se or as part of a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the DNAzyme molecule accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include systemic, oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, intratumoral or intraocular injections.

According to a specific embodiment, the composition is for pulmonary route of administration.

According to a specific embodiment, the composition is for inhalation mode of administration. Exemplary inhalers which can be used in accordance with some embodiments of the invention include pressurized metered-dose inhalers (pMDIs), breath-actuated metered dose inhalers (bMDIs), dry powder inhalers (DPIs, single or multidose), and soft mist inhalers.

According to a specific embodiment, the composition is for intranasal administration.

According to a specific embodiment, the composition is for intracerebroventncular administration.

According to a specific embodiment, the composition is for intrathecal administration.

According to a specific embodiment, the composition is for intratumoral administration.

According to a specific embodiment, the composition is for oral administration.

According to a specific embodiment, the composition is for local injection.

According to a specific embodiment, the composition is for systemic administration.

According to a specific embodiment, the composition is for intravenous administration.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers): and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution. Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the present invention include compositions wherein the active ingredients are contained in an amount effective to achieve the intended purpose. More specifically, a therapeutically effective amount means an amount of active ingredients (e.g. DNAzyme molecule) effective to prevent, alleviate or ameliorate symptoms of a disorder (e.g., senescent cell-related condition or cancer) or prolong the survival of the subject being treated.

According to an embodiment of the present invention, administration of the DNAzyme molecule has a senolytic effect (i.e. induces death of a senescent cell).

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide sufficient levels of the active ingredient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

It will be appreciated that animal models exist by which the DNAzyme molecules of the present invention may be tested prior to human treatment. For example, animal models for testing senolytic agents include mice with pulmonary fibrosis induced by solubilized bleomycin, and guinea pigs developing a condition similar to human osteoarthritis, as discussed in Kirkland and Tchkonia. *Exp Gerontol.* (2015) 68: 19-25, incorporated herein by reference. Furthermore, animal models for testing anti-cancer drugs are well known in the art and are discussed in Chavan, *International Journal of Pharmaceutical Sciences and Research* (2013) 4(1):19-28, incorporated herein by reference.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

According to one embodiment, there is provided an article of manufacture comprising the composition of matter of some embodiments of the invention, being packaged in a packaging material and identified in print, in or on the packaging material for use in the treatment of senescence-associated disease or disorder, a cancer or a fibrotic disease or disorder.

It will be appreciated that the therapeutic compositions of the invention may comprise, in addition to the DNAzyme molecule, other known medications for the treatment of senescence, e.g. senolytic agents (e.g., senolytic drugs). Exemplary senolytic agents which can be used in accordance with some embodiments of the invention include, but are not limited to. Dasatinib. Quercetin, Piperlongumine, Tocotrienols, Navitoclax, Bcl2-family inhibitors such as ABT-263 and ABT-737, PF-573228, JFD00244, Ouabain, Bufalin, Digoxin, K-Strophanthin, Strophanthidin, Cyclosporine, Tyrphostin AG879, Cantharidin, Diphenyleneiodonium chloride, Rottlerin, 2,3-Dimethoxy-1,4-naphthoquinone, LY-367,265, Rotenone, Idarubicin, Dequalinium chloride, Vincristine, Atorvastatin calcium. Fluvastatin sodium, Lovastatin, Pitavastatin calcium, Simvastatin, Nitazoxanide, Nitrofurazone, Temsirolimus, Eltrombopag, Adapalene, Azacyclonol, Enoxacin, Raltegravir, NSC 677249, Defactinib and HSP90 inhibitors (e.g. 17-DMAG and 17-AAG) (as discussed in U.S. Patent Application No. 2020/0121620, incorporated herein by reference).

It will be appreciated that the therapeutic compositions of the invention may comprise, in addition to the DNAzyme molecule, chemotherapeutic agents which may be affected concomitantly or separately to eliminate cancer cells such as those which have been pushed to senescence, and/or to eliminate or reduce certain side effects produced by senescent cells such as inflammation, promotion of cancer growth, promotion of metastasis and other side effects of chemotherapy, and/or to reduce or eliminate precancerous lesions. Non-limiting examples of chemotherapeutic agents include, but are not limited to, platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, 6-mercaptopurine, methotrexate, leucovorin, capecitabine, cytarabine, floxuridine, fludarabine, gemcitabine (Gemzar®), pemetrexed (ALIMTA®), raltitrexed, etc.), plant alkaloids (e.g., vincristine, vinblastine, vinorelbine, vindesine, podophyllotoxin, paclitaxel (Taxol®), docetaxel (Taxotere®), etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, idarubicin, actinomycin, bleomycin, mitomycin, mitoxantrone, plicamycin, etc.), anti-angiogenic agents (e.g. thalidomide or pomalidomide, e.g. Pomalyst and Imnovid), and other agents such as Palbociclib (e.g. Ibrance®), Lenalidomide (e.g. Revlimid®) or Lurbinectedin (e.g. Zepzelca®), and combinations thereof.

Additionally or alternatively, the therapeutic compositions of the invention may comprise, in addition to the DNAzyme molecule, biological therapy e.g., immunotherapy (e.g. antibody immunotherapy), cytokines/chemokines, hormonal therapy, which may be affected concomitantly or separately to eliminate senescence cells, cancer cells and/or to eliminate or reduce certain side effects produced by senescent cells such as inflammation, promotion of cancer growth, promotion of metastasis and other side effects of chemotherapy, and/or to reduce or eliminate precancerous lesions.

Any of the above described compositions may be packed together or separately (e.g. in a single container or in separate containers): e.g., DNAzyme packed separately from the chemotherapeutic agent or senolytic agent; or DNAzyme and the chemotherapeutic agent or senolytic agent in a single container.

According to another aspect of the present invention, there is provided a method of treating a senescence-associated disease or disorder in a subject in need thereof, the method comprising administering to the subject a therapeutically effective amount of the composition of matter of some embodiments of the invention, thereby treating the senescence-associated disease or disorder.

According to another aspect of the present invention, there is provided a therapeutically effective amount of the composition of matter of some embodiments of the invention for use in treating a senescence-associated disease or disorder in a subject in need thereof.

According to another aspect of the present invention, there is provided a method of treating a cancer in a subject in need thereof, the method comprising administering to the subject a therapeutically effective amount of the composition of matter of some embodiments of the invention, thereby treating the cancer.

According to another aspect of the present invention, there is provided a therapeutically effective amount of the composition of matter of some embodiments of the invention for use in treating cancer in a subject in need thereof.

According to another aspect of the present invention, there is provided a method of treating a fibrotic disease or disorder in a subject in need thereof, the method comprising administering to the subject a therapeutically effective amount of the composition of matter of some embodiments of the invention, thereby treating the fibrotic disease or disorder.

According to another aspect of the present invention, there is provided a therapeutically effective amount of the composition of matter of some embodiments of the invention for use in treating a fibrotic disease or disorder in a subject in need thereof.

The term "treating" refers to inhibiting, preventing or arresting the development of a pathology (disease, disorder or condition) and/or causing the reduction, remission, or regression of the pathology. Those of skill in the art will understand that various methodologies and assays can be used to assess the development of a pathology, and similarly, various methodologies and assays may be used to assess the reduction, remission or regression of a pathology.

As used herein, the term "subject" or "subject in need thereof" includes mammals, such as human beings, male or female, at any age which suffers from the pathology or is at risk to develop the pathology.

The term "senescence-associated disease or disorder" refers to any disease or condition in which senescent cells are involved in the pathogenesis of the disease, resistance to treatment, or side effects associated with a disease.

Exemplary senescence-associated disease or disorder include, but are not limited to, inflammatory or autoimmune diseases or disorders (e.g. osteoarthritis (OA), osteoporosis, oral mucositis, inflammatory bowel disease, kyphosis and herniated intervertebral disc), neurological diseases or disorders (e.g. Alzheimer's disease, Parkinson's disease. Huntington's disease, dementia, ataxia, mild cognitive impairment, macular degeneration and motor neuron dysfunction. e.g. amyotrophic lateral sclerosis (ALS)), metabolic diseases or disorder (e.g. diabetes, diabetic ulcer, metabolic syndrome, non-alcoholic fatty liver disease (NAFLD) and obesity), pulmonary diseases or disorder (e.g. chronic obstructive pulmonary disease (COPD), idiopathic pulmonary fibrosis (IPF), pulmonary fibrosis, chronic obstructive pulmonary disease, asthma, cystic fibrosis, emphysema, bronchiectasis, hyperoxic lung damage, and age-related loss of pulmonary function), eye diseases or disorders (e.g. macular degeneration, glaucoma, cataracts, presbyopia and vision loss), age-related diseases or disorders (e.g. renal disease, renal failure, frailty, hearing loss, muscle fatigue, age-related muscle loss, skin conditions, skin wound healing, liver fibrosis, pancreatic fibrosis, oral submucosa fibrosis, sarcopenia, age-related intervertebral disc disease, and age-related cognitive dysfunction), renal diseases or disorders (e.g. renal dysfunction, urinary incontinence), hepatic diseases or disorders (e.g. hepatic steatosis, cirrhosis, primary biliary cirrhosis, idiopathic non-alcoholic steatohepatitis (NASH)), dermatological diseases or disorders (e.g. eczema, psoriasis, hyperpigmentation, nevi, rashes, atopic dermatitis, urticaria, diseases and disorders related to photosensitivity or photoaging, rhytides, pruritis, dysesthesia, eczematous eruptions, eosinophilic dermatosis, reactive neutrophilic dermatosis, pemphigus, pemphigoid, immunobullous dermatosis, fibrohistocytic proliferations of skin, cutaneous lymphomas and cutaneous lupus), cardiac disease or disorder (e.g. cardiac dysfunction), vascular disease or disorder (e.g. vascular hyporeactivity/calcification, arteriovenous (AV) fistula), cardiovascular diseases or disorders (e.g. atherosclerosis) or other diseases or disorders such as preeclampsia, progeria, obesity-related neuropsychiatric dysfunction or prostatic hypertrophy.

According to a specific embodiment, the cell senescence is associated with drug-induced senescence (e.g. chemotherapy, e.g. chemotherapy complications).

According to a specific embodiment, the cell senescence is associated with irradiation-induced senescence (e.g. irradiation therapy. e.g. radiation complications).

According to a specific embodiment, the cell senescence is associated with transplantation of a cell, tissue or organ (e.g. bone marrow transplant or solid-organ transplant, e.g. transplant related complications such as graft rejection or graft versus host disease).

According to a specific embodiment, the cell senescence is associated with chronic wounds, such as non-healing chronic wounds.

According to a specific embodiment, the cell senescence is associated with environmental factors (e.g. smoking e.g. tobacco, radiation, pollution).

According to a specific embodiment, the cell senescence is associated with healthspan and/or lifespan.

Those of skill in the art will understand that various methodologies and assays can be used to assess the efficiency of treatment, for example, by detecting the levels of senescent cells in biological samples (e.g. blood, serum, cerebrospinal fluid (CSF), tissue sample) by using senescence associated markers such as, senescence-associated P-galactosidase, p161NK4a, p21, PA-1, or one or more senescence associated secretory phenotype (SASP) factors (IL-8, IL-1alpha, IL-1beta, IL-6, MMP10, MCP1, CXCL1, MMP1, STC1, GDF15, MMP9, CCL5, TNF, TGF-beta, SERPINE1), or by assessing the levels of senescent cell biomarkers including, e.g. DEP1, NTAL, EBP50, STX4, VAMP3, ARMCX-3, LANCL1, B2MG, PLD3 and VPS26A, using well known methodologies (e.g. RT-PCR, FACS, ELISA, or immunostaining).

According to one embodiment, an efficient senolytic treatment is determined when there is a decrease of at least about 10%, 20%, 30%, 40%, 50%, 60%, 70%, 80%, 90% or 100% or more in the number of senescent cells, as compared to the number of senescent cells in the subject being treated but prior to the treatment.

According to a specific embodiment, the disease is a fibrotic disease or disorder.

The term "fibrotic disease or disorder", also referred to as "fibrosis" or "fibro proliferative disease", as used herein refers to the formation of excess fibrous connective tissue in a reparative process upon injury or damage. Scarring is a result of continuous fibrosis that obliterates the affected organs or tissues architecture. As a result of abnormal reparative processes, which do not clear the formed scar tissue, fibrosis progresses further. Fibrosis can be found in various tissues, including the heart, the lungs, the liver, the skin, blood vessels and the kidneys.

An individual may be identified as having fibrosis by determining if a subject has organ dysfunction, scarring, alteration of normal extracellular matrix balance, increase in collagen deposition, increased collagen volume fraction, differentiation of fibroblasts to myofibroblasts, reduction in the level of matrix metalloproteinases and increase in the level of tissue Inhibitors of matrix metalloproteinases, increased levels of either N-terminal or C-terminal propeptide of type I procollagen (PINP or PICP) and decreased levels of C-terminal telopeptide of Type I Collagen (CTP or CITP), increased collagen deposition and impaired cardiac function measured by various noninvasive imaging techniques, impaired renal function measured by increased proteinurea and albuminuria, decreased glomerular filtration rate, doubling of plasma creatinine levels.

Exemplary fibrotic diseases include, but are not limited to, pulmonary fibrosis, (e.g. idiopathic pulmonary fibrosis (IPF), sarcoidosis, cystic fibrosis, familial pulmonary fibrosis, silicosis, asbestosis, coal worker's pneumoconiosis, carbon pneumoconiosis, hypersensitivity pneumonitides, pulmonary fibrosis caused by inhalation of inorganic dust, pulmonary fibrosis caused by an infectious agent, pulmonary fibrosis caused by inhalation of noxious gases, aerosols, chemical dusts, fumes or vapours, radiation-induced lung fibrosis, drug-induced lung fibrosis, e.g. drug-induced interstitial lung disease, autoimmune lung fibrosis (also referred to as connective tissue disease-related) or pulmonary hypertension), liver fibrosis (e.g., liver fibrosis resulting from a chronic liver disease, hepatitis B virus infection, hepatitis C virus infection, hepatitis D virus infection, schistosomiasis, alcoholic liver disease or non-alcoholic steatohepatitis, non-alcoholic fatty liver disease, obesity, diabetes, protein malnutrition, coronary artery disease, auto-immune hepatitis, cystic fibrosis, alpha-1-antitrypsin deficiency, liver cirrhosis, primary biliary cirrhosis, drug reaction and exposure to toxins, or bridging fibrosis), kidney fibrosis (e.g. progressive kidney disease, chronic kidney disease), pancreatic fibrosis, cardiac fibrosis (e.g. associated with various cardiovascular diseases, myocardial fibrosis, endomyocardial fibrosis), scleroderma or systemic sclerosis, oral submucosa fibrosis, intestinal fibrosis (e.g. Crohn's disease), eosinophilic esophagitis, hypereosinophilic syndromes (HES), Loeffler's endomyocarditis or skin fibrosis (e.g. scarring, hypertrophic scarring, keloid scarring, dermal fibrotic disorder, psoriasis or scleroderma. Scarring may be derived from a burn, a trauma, a surgical injury, a radiation or an ulcer. The ulcer can be a diabetic foot ulcer, a venous leg ulcer or a pressure ulcer).

According to a specific embodiment, the fibrosis is pulmonary fibrosis. Pulmonary fibrosis can result from different factors including, for example, drugs (e.g. amiodarone, nitrofurantoin, chemotherapy, methotrexate, or other drugs known to affect the lungs), radiation (e.g. prior or current radiation treatment to the chest), environmental factors (e.g. exposure to mold, animals), and occupational factors (e.g. exposure to dusts, fibers, fumes, or vapors such as asbestos, coal and silica). Lung fibrosis can also be autoimmune related (e.g. associated with joint inflammation) or idiopathic.

According to one embodiment, the fibrosis is organ fibrosis related to tissue injury including, but not limited to, fibrosis associated with cardiovascular disease, fibrosis associated with pulmonary disease, fibrosis associated with kidney disease, and fibrosis that has occurred following an organ transplant, such as a kidney, lung, heart or liver transplant.

According to a specific embodiment, the fibrosis is associated with a pulmonary disease, such as an idiopathic pulmonary fibrosis (IPF).

According to a specific embodiment, the fibrosis is associated with a kidney disease, such as a chronic kidney disease.

According to one embodiment, the fibrosis is associated with a chronic damage or injury.

According to one embodiment, an efficient anti-fibrotic treatment is determined when there is a decrease of at least about 10%, 20%, 30%, 40%, 50%, 60%, 70%, 80%, 90% or 100% or more in the number of fibrotic cells, or in the fibrotic tissue mass, as compared to the number of fibrotic cells, or fibrotic tissue mass, in the subject being treated but prior to the treatment.

Those of skill in the art will understand that various methodologies and assays can be used to assess the efficiency of anti-fibrotic treatment, e.g. imaging and blood tests (as discussed above).

According to one embodiment, the senescence-associated disease or disorder is associated with a cancerous disease.

According to one embodiment, the senescence-associated disease or disorder comprises an inflammation, precancerous lesions, promotion of cancer growth and/or of metastasis.

According to one embodiment, the cancer is therapy-resistant cancer (e.g. resistant to chemotherapy, radiation therapy, phototherapy/photodynamic therapy, or a combination thereof).

According to a specific embodiment, the cell senescence is associated with oncogene-induced senescence.

According to one embodiment, the cancer is not associated with cell senescence.

Types of cancerous diseases amenable to treatment by the methods of some embodiments of the invention include benign tumors, warts, polyps, pre-cancers, malignant tumors/cancers and cancer metastasis.

Examples of cancer include but are not limited to, carcinoma, blastoma, sarcoma and lymphoma. More particular examples of such cancers include, but are not limited to, tumors of the gastrointestinal tract (colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6: colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma, Biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer, sporadic; breast cancer, susceptibility to breast cancer, type 4 breast cancer, breast cancer-1, breast cancer-3; breast-ovarian cancer), squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B cell, Burkitt, cutaneous T cell, histiocytic, lymphoblastic, T cell, thymic), gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependimoblastoma, epithelioma, erythroleukemia (e.g., Friend, lymphoblast), fibrosarcoma, giant cell tumor, glial tumor, glioblastoma (e.g., multiforme, astrocytoma), glioma hepatoma, heterohybridoma, heteromyeloma, histiocytoma, hybridoma (e.g., B cell), hypemephroma, insulinoma, islet tumor, keratoma, leiomyoblastoma, leiomyosarcoma, leukemia (e.g., acute lymphatic, acute lymphoblastic, acute lymphoblastic pre-B cell, acute lymphoblastic T cell leukemia, acute—megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia), lymphosarcoma, melanoma, mammary tumor, mastocytoma, medulloblastoma, mesothelioma, metastatic tumor, monocyte tumor, multiple myeloma, myelodysplastic syndrome, myeloma, monoclonal gammopathy of undetermined significance (MGUS), nephroblastoma, nervous tissue glial tumor, nervous tissue neuronal tumor, neurinoma, neuroblastoma, oligodendroglioma, osteochondroma, osteormeloma, osteosarcoma (e.g., Ewing's), papilloma, transitional cell, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblastoma multiforme; multiple glomus tumors, Li-Fraumeni syndrome, liposarcoma, lynch cancer family syndrome II, male germ cell tumor, mast cell leukemia, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

According to a specific embodiment, the cancer is lung cancer.

According to one embodiment, treating a cancerous disease may be further effected by administering to the subject an additional medicament (or any combination of medicaments) for the treatment of the cancerous disease. Such medicaments may include, without being limited to, radiation therapy, chemotherapy, biological therapy, e.g., immunotherapy (e.g. antibody immunotherapy), phototherapy/photodynamic therapy, surgery, nutritional therapy, or combinations thereof. Such medicaments may be affected prior to, concomitantly with, or following the DNAzyme molecules of some embodiments of the invention.

It will be appreciated that the use of the DNAzymes of some embodiments of the invention can reduce the amount of chemotherapy administered to a subject needed to achieve a therapeutic effect (i.e. elimination of cancer cells). Such a therapy is specifically beneficial in order to reduce harm to healthy cells.

According to one embodiment, an efficient anti-cancer treatment is determined when there is a decrease of at least about 10%, 20%, 30%, 40%, 50%, 60%, 70%, 80%, 90% or 100% or more in tumor mass or there is a halt in tumor growth, as compared to a subject not treated by the composition of the invention, or compared to the same subject being treated but prior to the treatment.

Those of skill in the art will understand that various methodologies and assays can be used to assess the efficiency of cancer treatment, e.g. CT scan, MRI, X-ray, ultrasound, blood tests etc.

According to one embodiment the DNAzyme molecules of some embodiments of the invention may be administered to the subject as a single DNAzyme molecule treatment. Alternatively, the DNAzyme molecules of some embodiments of the invention may be administered to the subject in combination (e.g. 2, 3, 4, 5 or more DNAzymes) in order to mediate cleavage of two or more target sites in p21 mRNA thereby increasing efficiency of RNA silencing. Such a determination is well within the capability of one of skill in the art.

According to another aspect, there is provided a method of determining the senolytic effect of a DNAzyme molecule, the method comprising contacting senescent cells with the composition of matter of some embodiments of the invention, wherein a reduction in the number of senescent cells as compared to a number of senescent cells prior to the contacting is indicative of the DNAzyme molecule having the senolytic effect.

According to one embodiment, an efficient senolytic effect is determined when there is a reduction of at least about 10%, 20%, 30%, 40%, 50%, 60%, 70%, 80%, 90% or 100% or more in the number of senescent cells, as compared to the number of senescent cells prior to contacting.

According to another aspect, there is provided a method of determining the anti-cancer effect of a DNAzyme molecule, the method comprising contacting cancer cells with the composition of matter of some embodiments of the invention, wherein a reduction in the number of cancer cells as compared to a number of cancer cells prior to the contacting is indicative of the DNAzyme molecule having the anti-cancer effect.

According to one embodiment, an efficient anti-cancer effect is determined when there is a reduction of at least about 10%, 20%, 30%, 40%, 50%, 60%, 70%, 80%, 90% or 100% or more in the number of cancer cells, as compared to the number of cancer cells prior to contacting.

According to one embodiment, the method is affected n vitro or ex-vivo (e.g. in a cell culture).

According to one embodiment, the method is affected in vivo.

According to one embodiment, the in vivo method is affected in an animal model for a senescence-associated disease or for a cancer-associated disease. Suitable animals include, but are not limited to, porcines (e.g. pig), bovines (e.g., cow), equines (e.g., horse), ovines (e.g., goat, sheep), felines (e.g., *Felis domestica*), canines (e.g., *Canis domestica*), rodents (e.g., mouse, rat, rabbit, guinea pig, gerbil, hamster), and primates (e.g., chimpanzee, rhesus monkey, macaque monkey, marmoset).

According to a specific embodiment, the in vivo method is affected in a mouse model for a senescence-associated disease.

As mentioned above, various animal models exist by which the DNAzyme molecules of the present invention may be tested prior to human treatment. These include, for example, mice with pulmonary fibrosis induced by solubilized bleomycin and mice exhibiting chronic obstructive pulmonary disease (COPD) induced by chronic LPS exposure or by cigarette smoke.

In order to assess the efficiency of treatment with DNAzymes, the present inventors generated a DNAzyme molecule capable of mediating cleavage of p21 mRNA corresponding to mouse p21 mRNA (as set forth in SEQ ID NO: 3).

According to one embodiment, the DNAzymes targeting p21 mRNA corresponding to SEQ ID NO: 3 comprise a nucleic acid sequence at least 80%, 81%, 82%, 83%, 84%, 85%, 86%, 87%, 88%, 89%, 90%, 91%, 92%, 93%, 94%, 95%, 96%, 97%, 98%, 99% or 100% identical to the nucleic acid sequence set forth in any one of SEQ ID NOs: 83-85.

According to one embodiment, the DNAzyme molecule comprises a nucleic acid sequence at least 85% identical to the nucleic acid sequence set forth in any one of SEQ ID NOs: 83-85.

According to one embodiment, the DNAzyme molecule comprises a nucleic acid sequence at least 90% identical to the nucleic acid sequence set forth in any one of SEQ ID NOs: 83-85.

According to one embodiment, the DNAzyme molecule comprises a nucleic acid sequence at least 95% identical to the nucleic acid sequence set forth in any one of SEQ ID NOs: 83-85.

According to one embodiment, the DNAzyme molecule comprises a nucleic acid sequence at least 98% identical to the nucleic acid sequence set forth in any one of SEQ ID NOs: 83-85.

According to one embodiment, the DNAzyme molecule comprises a nucleic acid sequence as set forth in any one of SEQ ID NOs: 83-85.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from I to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, SEQ ID NO: 1 is expressed in a DNA sequence format (e.g., reciting T for thymine), but it can refer to either a DNA sequence that corresponds to an p21 nucleic acid sequence, or the RNA sequence of an RNA molecule nucleic acid sequence. Similarly, though some sequences are expressed in a RNA sequence format (e.g., reciting U for uracil), depending on the actual type of molecule being described, it can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes 1-III Ausubel, R. M., ed. (1994); Ausubel et al., "Current Protocols in Molecular Biology", John Wiley and Sons, Baltimore. Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057: "Cell Biology: A Laboratory Handbook", Volumes I-III Cellis, J. E., ed. (1994); "Current Protocols in Immunology" Volumes I-III Coligan J. E., ed. (1994): Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839, 153; 3,850,752; 3,850,578; 3,853,987; 3,867,517; 3,879, 262; 3,901,654; 3,935,074; 3,984,533; 3,996,345; 4,034, 074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984): "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press: "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

Cell Culture

Human IMR-90, BJ, WI-38 fibroblasts and REC epithelial cells were obtained from ATCC and grown at 5% oxygen. IMR-90 and REC cells were maintained in DMEM medium comprising 100 units per ml of penicillin, 100 mg/ml of streptomycin and 10% fetal bovine serum. BJ and WI-38 cells were maintained in EMEM medium comprising 100 units per ml of penicillin, 100 mg/ml of streptomycin, 10% fetal bovine serum, 1% Pyruvate, 1% L-Glutamine, mLFs were isolated according to standard procedures [Seluanov, A., et al. *J Vis Exp* (2010) (44):2033] and grown at 5% oxygen. Cells were maintained in EMEM medium comprising 100 units per ml of penicillin, 100 mg/ml of streptomycin and 15% fetal bovine serum.

DNA damage induced senescence (DIS) was induced by etoposide treatment (E1383, Sigma) at a concentration of 1000 µM for IMR-90, BJ, and WI-38, 16 µM for mLF and 12.5 µM for REC for a duration of 48 hours. Cells acquired the senescence phenotype 7 days post treatment (determined by SA-beta-gal staining).

PANC-1 cells were maintained in DMEM medium supplemented with 10% fetal bovine serum, 1% penicillin-streptomycin and 1% sodium pyruvate. HCT116 cells were maintained in McCoy's 5A medium supplemented with 10% fetal bovine serum and 1% penicillin-streptomycin. A549 cells were maintained in F-12K Medium supplemented with 10% fetal bovine serum and 1% penicillin-streptomycin. HepG2 cell were maintained Eagle's Minimum Essential Medium, supplemented in 10% fetal bovine serum, 1% penicillin-streptomycin and 1% sodium pyruvate. All cancer cell lines were incubated in 5% C02 at 37° C.

Oncogene Induced Senescence (OIS) was induced by means of retroviral infection with H-RasG12 (pLNCX2) at 5% oxygen. Retroviruses were packaged, and infections were performed as described below.

Phoenix-AMPHO cells were plated in a 6 well dish, incubated for 24 hours, and then transfected using Lipofectamine™ 200 (Invitrogen) with 1 mg of a retroviral plasmid. After 48 hours, the virus-containing medium was filtered (0.45 mm filter, Millipore) and supplemented with 4 mg/ml polybrene (Sigma) (first supernatant). Viruses were collected for an additional 24 hours as before (second supernatant). IMR-90 cells were plated at $1.2 \times 10^6$ cells per 10 cm dish and incubated for 48 hours. For infections, the culture medium was replaced with the first supernatant for 24 hours. The infection process was repeated using the second supernatant. Two days following infection, selection was carried out using 400 µg/ml G418 for a duration of 3-4 days. By 7 days post-infection, the cells were used for viability assay.

Replicative Induced Senescence (RIS) was induced by long-term passaging of the cells in tissue culture. Cells acquired the senescence phenotype after 40 population doublings.

Viability Assay

Primary target cells (IMR-90, BJ, WI- and 38 and REC) were plated in 24-well plates at 100,000 cells per well. Cells were transfected with different concentrations of DNAzymes (as depicted in Table 2, below) using Lipofectamine™ 2000 (Invitrogen) according to manufacturer instructions. The percentage of survival was determined based on quantification of remaining adherent cells using PrestoBlue® reagent (A13262, Life Technologies Ltd.) relative to Lipofectamine™ only control and compared to Scramble DNAzyme (Dz_Scramble) [Scramble Arm (Scr A) sequence: ATCTTCCTFggctagctacaacgaCGCCTCTCC, SEQ ID NO: 5, or Scramble catalytic core (Scr B) sequence: AGGAGAACAacagtaactggcgacGGGATGAGG, SEQ ID NO: 86] treated cells, 3-6 days following transfection.

In some of the experiments, the following control Scramble DNAzymes were utilized: sequence: ATCTTCCTTggctagctacaacgaCGCCTCTCC. SEQ ID NO: 5, and GTGTGGCGcccgagccggacgaGAGTGGAGG, SEQ ID NO: 125, for 10-23 and 8-17 DNAzymes respectively.

Chemotherapy and DNAzyme Treatments

Cancer cell lines were seeded in 96 well plates 24 hours before treatment. Chemotherapies were applied at indicated concentrations either alone or as combination with DNAzyme-lipofectamine complex. 72 hours following treatment, cell viability was measured using Prestoblue® reagent. Chemotherapies were diluted in cell medium to the indicated concentrations. 24 hours following seeding, culture medium was replaced with chemotherapy containing medium, immediately followed by transfection of DNAzyme as described above. 72 hours following treatment, cell viability was measured using Prestoblue® reagent.

The following chemotherapies were used: Etoposide (Sigma), Palbociclib (Sigma), Doxorubicin (Sigma), Cisplatin (Sigma), ABT-263 (Selleckchem). All compounds were dissolved and stored according to manufacturer instructions.

TABLE 4

Concentrations of chemotherapy and DNAzyme

| Cell line | Chemotherapy | Clinical dose (mM) | Sub-clinical dose (mM) | DNAzyme (mM) |
|---|---|---|---|---|
| HepG2 | Etoposide | 150 | 10 | 40 |
|  | Doxorubicin | 40 | 20 | 40 |
|  | Palbociclib | 31.2 | 7.8 | 40 |
|  | Cisplatin | 16 | 2 | 40 |
| A549 | Etoposide | 50 | 5 | 12.5 |
| Panc1 | Etoposide | 50 | 1 | 25 |
| HCT-116 | Etoposide | 150 | 5 | 25 |

DNAzymes

DNAzymes containing either the 10-23 or 8-17 catalytic domains were designed for the selected mRNA targets and the oligonucleotides were ordered from Axolabs or Integrated DNA Technologies Syntezza (including all modified oligonucleotides). Control DNAzymes with scrambled arms were designed using an online software tool (GenScript®).

mRNA Target Preparation

Total RNA was isolates from senescent IMR-90 cells using Nucleospin® RNA kit (Macherey-Nagel™). cDNA was synthesized with gene-specific reverse primers using M-MLV Reverse Transcriptase (Promega), according to the manufacturer's protocol. To generate template for in vitro transcription (IVT) reaction, the cDNA was PCR amplified using KAPA Taq EXtra HotStart® ReadyMix™ PCR Kit (R&D). PCR product was run on 1.5% agarose TAE gel, the correct band size was cut and DNA was cleaned using Wizard® SV Gel and PCR Clean-Up System kit (Promega). IVT was performed using HiScribe™ T7 High Yield RNA Synthesis Kit (NEB). Samples were then treated with DNase I (New England Biolabs) and incubated for 15 minutes at 37° C. IVT product was run on 1.5% agarose TBE gel, the correct band size was cut and RNA was cleaned using QIAquick® Gel Extraction Kit (Qiagen). See primer sequences in Table 1, below.

TABLE 1

Primer list

| | | | |
|---|---|---|---|
| Human | T7 CDKN1A FORWARD | TAATACGACTCACTATAGATGTTGAGCTCTGGCA TAGAAGAGGCTGGTGGCTATTTTGTCCTTGGGCT GCCTGTTTTCAG (SEQ ID NO: 79) | cDNA + PCR |
| Human | CDKN1A REVERSE | TAAAGTCACTAAGAATCATTTATTGAGCACCTGC TGTATATTCAGCATTGTGGGAGGAGCTGTGAAAG ACACAGAACAGT (SEQ ID NO: 80) | PCR |
| Mouse | Mouse cdkn1a_REVERSE | AATCATCGAGAAGTATTTATTGAGCACCAGCTTT GGGGTCGGGTGTGAGGACTCGGGACAATGCAGG (SEQ ID NO: 81) | cDNA + PCR |
| Mouse | Mouse T7_cdkn1a_FORWARD | TAATACGACTCACTATAGTGCAGCAGCCGAGAG GTGTGAGCCGCC (SEQ ID NO: 82) | PCR |
| Human | GAPDH Forward | TGGTATCGTGGAAGGACTCA (SEQ ID NO: 95) | RT-PCT |
| Human | GAPDH Reverse | CCAGTAGAGGCAGGGATGAT (SEQ ID NO: 96) | RT-PCT |

TABLE 1-continued

Primer list

| | | | |
|---|---|---|---|
| Human p21 Dz 387 Forward | TCAAAGGCCCGCTCTACATC (SEQ ID NO: 97) | RT-PCT |
| Human p21 Dz 387 Reverse | TGCCCAGCACTCTTAGGAAC (SEQ ID NO: 98) | RT-PCT |
| Mouse GAPDH Forward | TCAAGCTCATTTCCTGGTATGACA (SEQ ID NO: 99) | RT-PCT |
| Mouse GAPDH Reverse | TAGGGCCTCTCTTGCTCAGT (SEQ ID NO: 100) | RT-PCT |
| Mouse p21 Forward | GTGTGCCGTTGTCTCTTCGG (SEQ ID NO: 101) | RT-PCT |
| Mouse p21 Reverse | CTCAGGTAGACCTTGGGCAG (SEQ ID NO: 102) | RT-PCT |
| Mouse p16 Forward | CATCTGGAGCAGCATGGAGTC (SEQ ID NO: 103) | RT-PCT |
| Mouse p16 Reverse | GTTGCCCATCATCATCACCTGAAT (SEQ ID NO: 104) | RT-PCT |
| Mouse IL-6 Forward | TCCTTAGCCACTCCTTCTGT (SEQ ID NO: 105) | RT-PCT |
| Mouse IL-6 Reverse | AGCCAGAGTCCTTCAGAGA (SEQ ID NO: 106) | RT-PCT |
| Mouse MCP1 Forward | TCCCAAAGAAGCTGTAGTTTTTGTC (SEQ ID NO: 107) | RT-PCT |
| Mouse MCP1 Reverse | CCCATTCCTTCTTGGGGTCA (SEQ ID NO: 108) | RT-PCT |
| Mouse COL1A Forward | CCAACAAGCATGTCTGGTTAGGAG (SEQ ID NO: 109) | RT-PCT |
| Mouse COL1A Reverse | GCAATGCTGTTCTTGCAGTGGTA (SEQ ID NO: 110) | RT-PCT |
| Mouse HPRT Forward | AGCAGGTCAGCAAAGAACT (SEQ ID NO: 111) | RT-PCT |
| Mouse HPRT Reverse | CCTCATGGACTGATTATGGACA (SEQ ID NO: 112) | RT-PCT |
| Mouse RPLP0 Forward | TTCCAGGCTTTGGGCATCA (SEQ ID NO: 113) | RT-PCT |
| Mouse RPLP0 Reverse | ATGTTCAGCATGTTCAGCAGTGTG (SEQ ID NO: 114) | RT-PCT |
| Mouse MMP12 Forward | GCTCCTGCCTCACATCATAC (SEQ ID NO: 115) | RT-PCT |
| Mouse MMP12 Reverse | GGCTTCTCTGCATCTGTGAA (SEQ ID NO: 116) | RT-PCT |
| Mouse TIMP1 Forward | GAGACACACCAGAGCAGATACC (SEQ ID NO: 117) | RT-PCT |
| Mouse TIMP1 Reverse | GGGGAACCCATGAATTTAGCC (SEQ ID NO: 118) | RT-PCT |
| Human p21 off-site 3' Forward | TATGGGGCTGGGAGTAGTTGT (SEQ ID NO: 119) | RT-PCT |
| Human p21 off-site 3' Reverse | GGGAGCCGAGAGAAAACAGTC (SEQ ID NO: 120) | RT-PCT |
| Human p21_offsite 5'_Forward | GACAGCAGAGGAAGACCATGTGGAC (SEQ ID NO: 121) | RT-PCT |
| Human p21_offsite 5'_Reverse | GAGTGGTAGAAATCTGTCATGCTG (SEQ ID NO: 122) | RT-PCT |

TABLE 1-continued

Primer list

| | | | |
|---|---|---|---|
| Human | p21_DNZ1 99_Onsite_Forward | TTGGCTCCCCTGTACCTTTTG (SEQ ID NO: 123) | RT-PCT |
| Human | p21_DNZ1 99_Onsite_Reverse | TGGAGCTGAGAGGGTACTGA (SEQ ID NO: 124) | RT-PCT |

In Vitro Cleavage Assay

RNA substrate was diluted with Molecular Biology Grade Water (Biological Industries) and used in in vitro cleavage assay. A 20 µl reaction system comprising RNA substrate (final concentration 500 nM), 2 µl 10× reaction buffer (50 mM Tris-HCl pH 7.4, 100 mM NaCl, 10 mM MgCl2) and 1 µl DNAzyme (10 µM) (as depicted in Table 2, below) was mixed. Reactions were incubated at 37° C. for 60 min. 2×RNA L.D. (Thermo Fisher) was added to each sample. Samples were heated at 70° C. for 30 sec, centrifuged and loaded onto 1.5% agarose TBE gels. Quantification was performed using Image Lab software (Bio Rad).

Quantitative RT-PCR

Total RNA was extracted from IMR-90 cells using NucleoSpin® RNA (Macherey-Nagel™), according to the manufacturer protocol. Complementary DNA was prepared using the M-MLV Reverse Transcriptase (Promega), according to the manufacturer protocol. Quantitative real-time PCR was performed using the SYBR Green PCR mastermix (Applied Biosystems) on a CFX96 Real-Time PCR System (Bio Rad). See primer sequences in Table 1, above.

Total RNA from lung samples (post-caval lobe) was extracted using RNAiso (Takara Bio. Japan) according to manufacturer protocol. Reverse transcription was performed using MMLV-RT (Invitrogen). Real-time PCR was performed using TB Green™ Premix Ex Taq™ II (Takara Bio). To calculate the relative mRNA expression level, the expression of each gene (Collagen Type 1) were be normalized to that of reference gene 36B4 (gene symbol: Rplp0).

P21 ELISA Kit p21 protein quantification was analyzed using (Human p21 ELISA Kit—ab214658, Abcam), according to the manufacturer's instructions. The cell pellets were incubated with Cell Extraction Buffer PTR on ice for 20 minutes. Following Centrifuge at 18,000×g for 20 minutes, the sample protein concentrations were quantified using a BCA protein assay. The samples and Antibody Cocktail were added to appropriate wells and incubated for one hour at room temperature (RT), followed by three washes with Wash Buffer and incubation with TMB Development Solution for 15 minutes at RT. Then, the Stop Solution was added, the samples were incubated for 1 minute, and the samples were read by absorbance at 450 nm using plate reader.

Immunofluorescence 48 hours following transfection. IMR-90 cells were fixed by PFA 4% following the indicated treatments. Cells were blocked and incubated with antibodies against human p21 (CST) in blocking solution. Cells were then incubated with Dylight-549-conjugated secondary antibody (Jackson ImmunoResearch) and counterstained with DAPI (Sigma). Images were acquired using Nikon Eclipse Ti2 microscope at ×10 magnification.

Alternatively, cells were fixed with 4% Formaldehyde for 15 minutes, permeabilized in 0.2% Triton X-10 for 5 minutes and blocked with 2% bovine serum albumin (BSA) for 30 min in room temperature. Cells were then incubated with a primary or with a conjugated antibody over-night or for 3 hours respectively. For unconjugated antibodies, a corresponding fluorescently-labelled secondary antibody was added for 1 hour, followed by Hoechst counterstaining. Cells were washed with PBS three times following each step. Images were acquired using Nikon Eclipse Ti2 microscope at ×10 magnification.

Antibodies

Antibodies were diluted in blocking solution as indicated below: 53BP1 antibody (Novus biologicals NB100-304, 1:800), Phospho-histone H2AX antibody (Cell signaling #2577, 1:800), p21 Waf1/Cip1 antibody (Cell signaling #8865, 1:500), p16 antibody (Santa Cruz sc-56330, 1:200), Alexa Fluor-488 goat anti mouse (Thermo Fisher A11029, 1:1000).

Apoptosis Assay

Apoptosis was measured by quantification of Cleaved Caspase-3/7 (CC3/7) signal, obtained following incubation of CellEvent™ Caspase-3/7 Green Detection Reagent (Invitrogen) with DNAzyme treated IMR-90 senescent cell. IMR-90 senescent cells were plated in 24 well plate, 100 k cells per well. Growth media containing 2 µl of CellEvent™ Caspase-3/7 Green Detection Reagent and Nucblue™ (Invitrogen) was added to the cells prior to DNAzyme treatment. Cells were scanned with Nikon Eclipse Ti2 microscope (4× magnification) 0, 24, 48, 72, 96 hours following transfection. Images were analyzed using NIS elements software. Caspase 3/7 intensity was measured and normalized to cell number.

Flow Cytometry (FACS) Stained cells were lifted using TrypLE™ (Thermo Fisher scientific), washed and filtered through 100 µm cell strainer. Cells were analyzed using MA900 multi-application cell sorter (Sony), and Kaluza V2.1 (Beckman Coulter).

DNAzyme Stability Analysis

DNAzyme stability was assessed by incubation with PBS, plasma and BALF (Bronchoalveolar Lavage Fluid). A comparison between unmodified and 3'Inverted dT modification was made. Following incubation for the indicated time points, samples were analyzed using gel electrophoresis. Quantification compared to time 0 was performed using Image Lab software (Bio Rad).

Animal Studies

All animal studies were performed under the approval of the council for experiments on animal subjects, Israel. Animals used in the study were housed and cared for in accordance with the international standards and the ILAR guide (the Institute for Laboratory Animal Research, Guide for the Care and Use of Laboratory Animals). Mice were obtained from ENVIGO CRS (ISRAEL) LTD, or from Japan SLC, Inc. (Japan).

In-Vivo Biodistribution and Kinetics of DNAzyme Mice 8 weeks old female C57/BL6 were treated intratracheally with Bleomycin (1.5 mg/kg, Enzo) to induce pulmonary fibrosis or with PBS as control. 7 days following disease induction mice were intratracheally treated with 200 µg of Cy5.5 fluorescently labelled DNAzyme 1670 (Cy5.5-DNAzyme 1670-3InvdT, Syntezza) or PBS as control. Total body imaging was performed in the following time points: 30 min, 1, 2, 4, 8, 24, 48 and 72 hours. Mice were anesthetized using Isoflurane and imaging was performed using Ami HT spectral instrument imaging. Satellite mice were sacrificed at 30 min, 2 and 8 hours, organs were excised and imaged. Quantification was performed using Aura imaging software.

Kinetics of DNAzyme Uptake in Mouse Lungs after Intranasal Administration 8 weeks old female C57/BL6 were treated intratracheally with Bleomycin (1.5 mg/kg, Enzo) to induce pulmonary fibrosis or with PBS as control. 7 days following disease induction mice were intranasally administered with 200 Mg of Rhodamine 6G labelled DNAzyme 1670 (Rho-DNAzyme 1670-3InvdT, Syntezza) or PBS as control. Mice were sacrificed at the following time points: 30 min, 2, 4, 8, 24, and 48 hours. Lungs were inflated and fixed with 4% PFA. 3 mm histological sections were sliced using counter stained with DAPT Samples were analyzed using Nikon Eclipse Ti2 microscope.

In-Vivo Safety of DNAzyme in Mice 8 weeks old male and female C57/BL6 were treated intranasally with DNAzyme 1670 for 14 days. DNAzyme was administered in three concentrations: 40, 200 and 1000 µg. PBS treated mice served as control. Body weight, viability, clinical signs and behavior were monitored daily. On day 14, blood was collected using cardiac puncture and mice were sacrificed thereafter. Blood analyses were performed by AML (Central Lab Services). Hematology was performed using Advia-2120 (Siemens Healthineers). Biochemistry was performed using COBAS® 6000 (Roche Diagnostics).

Idiopathic Pulmonary Fibrosis (IPF) in an Animal Model

C57/B6 mice were induced to develop pulmonary fibrosis by a single intra-tracheal administration of Bleomycin hydrochloride (Nippon Kayaku. Japan) in saline at a dose of 3.0 mg/kg, in a volume of 50 µL per animal using Micros-prayer® (Penn-Century. USA). Mice that served as the Sham control group were intratracheally administered with saline, instead of the Bleomycin. Mice were initially randomized based on body weight before Bleomycin instillation. At second randomization, Bleomycin-induced pulmonary fibrosis model mice were divided based on the body weight changes on the day before the start of treatment at Day 7. DNAzyme treatment was performed intranasally with 200 µg of DNAzyme resuspended in 50 µL PBS per treatment. PBS intra-nasal treatment served as control. Mice were treated daily following Bleomycin instillation with either DNAzyme or control from day 1 to 20 (prophylactic regimen) or from day 7 to 20 (therapeutic regimen). Body weight, viability, clinical signs and behavior were monitored daily. Mice were sacrificed three weeks following Bleomycin instillation.

Unilateral Ureteral Obstruction (UUO) Animal Model

UUO surgery was performed under three types of mixed anesthetic agents (medetomidine, midazolam, butorphanol). After shaving the hair, the abdomen was cut open and the left ureter was exteriorized. The ureter was ligated by 4-0 silk sutures at two points. The peritoneum and the skin were closed with sutures, and the mice were transferred to a clean cage and kept until recovery from anesthesia. Mice were divided into groups of 8 mice based on the body weight on the day before disease induction. P21-targeting DNAzyme (DNZ_p21) was administered intravenously at a dose level of 10 mg/kg in a volume of 5 mL/kg at Days 0, 2, 4, 7, 9 and 11. The animals were sacrificed by exsanguination through direct cardiac puncture under isoflurane anesthesia (Pfizer Inc.) at Day 14. The ligated left kidney and right kidney weights were measured at sacrifice. To visualize collagen deposition, kidney sections were stained using Picro-Sirius red solution (Waldeck, Germany). For quantification of interstitial fibrosis area, bright field images in the corticomedullary region were captured using a digital camera (DFC295) at 200-fold magnification, and the positive areas in 5 fields/section were measured using ImageJ software (National Institute of Health, USA).

Histological Analysis

Right lung tissues prefixed in 10% neutral buffered formalin were embedded in paraffin and sectioned at 4 µm.

For immunohistochemistry (IHC) staining, sections were subjected to heat induced epitope retrieval (HIER) Following HIER, the sections were incubated rabbit monoclonal anti-p21 antibody [EPR18021] (Abcam) 1:2000 or rabbit monoclonal anti-α-SMA antibody [EPR5368] (Abcam) 1:2000. Section bound primary antibody was detected employing horseradish peroxidase labeled anti-rabbit IgG polymeric reagent.

For Masson's Trichrome staining, the sections were deparaffinized and rehydrated, followed by re-fixation with Bouin's solution for 15 minutes. The sections were stained in Weigert's iron Hematoxylin working solution (Sigma-Aldrich), Biebrich scarlet-Acid fuchsin solution (Sigma-Aldrich), Phosphotungstic/phosphomolybdic Acid solution, Aniline blue solution and 1% Acetic Acid solution (Sigma-Aldrich). For quantitative analysis of lung fibrosis area, bright field images of Masson's Trichrome-stained sections were randomly captured using a digital camera (DFC295; Leica, Germany) at 100-fold magnification, and the subpleural regions in 20 fields/mouse were evaluated according to the criteria for grading lung fibrosis [Ashcroft. T. et al., Simple method of estimating severity of pulmonary fibrosis on a numerical scale. *J Clin. Pathol.* (1988) 41: 467-470]. All sections were blindly analyzed by an experimenter.

Image Analysis

Digital images were analyzed by a custom MATLAB algorithm, using Image Processing Toolbox. First, a binary image was calculated, in order to distinguish background pixels from the lobe pixels. Next, a morphological close operation on the image was preformed, fill of the holes, and extraction of the largest connected component, in order to detect all lobe area, including alveoli. The density of the lobe was defined by the ratio between the stained pixels to the total pixels in the lobe area. For Masson's Trichrome staining, blue pixels were detected and separated from purple staining by specifying RGB (red, green, and blue) constraints. The Collagen percentage in each image was defined by the ratio between the blue pixels to the total pixels in the lobe area.

For p21 staining, an image segmentation algorithm was performed to identify all nuclei in image. Next, cells positive to p21 were detected by RGB and size constraints.

Hydroxyproline Analysis

To quantify lung hydroxyproline content, frozen left lung samples were processed by an acid hydrolysis method as follows. Lung samples were acid-hydrolyzed with 300 µL of 6N HCl at 121° C. for 20 minutes, and neutralized with 300 µL of 4N NaOH containing 10 mg/mL activated carbon. AC buffer (2.2 M acetic acid/0.48 M citric acid, 300 µL) was added to the samples, followed by centrifugation to collect the supernatant. A standard curve of hydroxyproline was constructed with 16, 8, 4, 2, 1 and 0.5 µg/mL of trans-4- hydroxy-L-proline (Sigma-Aldrich Co. LLC., USA). The prepared samples and standards (each 400 μL) were mixed with 400 μL chloramine T solution (NACALAI TESQUE, INC., Japan) and incubated for 25 minutes at room temperature. The samples were then mixed with Ehrlich's solution (400 μL) and heated at 65° C. for 20 minutes to develop the color. After samples were cooled on ice and centrifuged to remove precipitates, the optical density of each supernatant was measured at 560 nm. The concentrations of hydroxyproline were calculated from the hydroxyproline standard curve. Lung hydroxyproline levels were expressed as μg per left lung.

Statistical Analysis

Data are presented as means±s.d. unless otherwise noted. Comparisons between two groups were performed by an unpaired two-tailed Student's t-test, and analysis of variance (ANOVA) with Dunnett's or Tukey's multiple comparisons post hoc test or a Fisher's LSD test. For consistency in comparisons, significance in all figures is denoted as follows: *P<0.05, P<0.01. *P<0.001, ****p<0.0001.

Example 1

Specific Human p21 mRNA Targeting DNAzymes

Various DNAzymes were defined that target human p21 mRNA (as set forth in SEQ ID NO: 1, and presented in FIG. 3). The DNAzyme sequences and the location of the cleavage sites in p21 mRNA are presented in Table 2, below (the DNAzyme names relate to their cleavage site position on the p21 mRNA). The DNAzymes were shown to be effective in mediating in vitro cleavage of p21 mRNA (FIGS. 4A-B). This effect was time and concentration dependent as shown, for example, for DNAzyme 1670 (FIGS. 4C-D). Results from examination of DNAzymes in vitro cleavage of p21 mRNA are depicted in Table 2, below.

TABLE 2

| DNAzyme Name (Dz) | DNAzyme sequence | SEQ ID NO: | Validated cleavage | Validated cytotoxicity |
|---|---|---|---|---|
| 16 | CCTCTTCTAggctagctacaacgaGCCAGAGCT | 6 | – | + |
| 75 | CTCCTACCAggctagctacaacgaCCCCTTCCT | 7 | NT | + |
| 78 | TGTCTCCTAggctagctacaacgaCATCCCCTT | 8 | NT | + |
| 100 | TCTGGGGTtccgagccggacgaTTAGAGGTC | 9 | NT | + |
| 111 | CATCCTTTAggctagctacaacgaTTCTGGGGT | 10 | NT | + |
| 174 | GCAAAGAAAggctagctacaacgaGACTATAGT | 11 | NT | + |
| 185 | CAGATCATGggctagctacaacgaAGCAAAGAA | 12 | NT | + |
| 224 | TGGGGAAAtccgagccggacgaGGGGCTCAG | 13 | NT | + |
| 225 | CTGGGGAAAggctagctacaacgaTGGGGCTCA | 14 | NT | + |
| 236 | CGTATACAtccgagccggacgaGCTGGGGAA | 15 | NT | + |
| 237 | CCGTATACAggctagctacaacgaTGCTGGGGA | 16 | NT | + |
| 252 | TACTCCCCAggctagctacaacgaATAGCCCGT | 17 | NT | + |
| 266 | GTCTGTCTtccgagccggacgaTGAATACTC | 18 | NT | + |
| 290 | AGGGGAGGAggctagctacaacgaTTGACGAGT | 19 | NT | + |
| 304 | TTTGTTGGtccgagccggacgaAGGAAGGGG | 20 | NT | + |
| 317 | TGGTTGCAGggctagctacaacgaAGCTTTGTT | 21 | NT | + |
| 352 | GTTCTGACAggctagctacaacgaGGCGCCTGA | 22 | – | + |
| 354 | CGGTTCTGAggctagctacaacgaATGGCGCCT | 23 | + | + |
| 364 | TGACGGACAggctagctacaacgaCCCCAGCCG | 24 | – | + |
| 377 | GGGTTCTGAggctagctacaacgaGGACATCCC | 25 | – | + |
| 387 | GCTGCCGCAggctagctacaacgaGGGTTCTGA | 26 | – | + |
| 394 | AGGCctTGtccgagccggacgaGCCGCATGG | 27 | – | + |
| 442 | AGTCGCGGtccgagccggacgaCAGCTGCTC | 28 | – | + |
| 495 | GAAGTTCCAggctagctacaacgaCGCTCACGG | 29 | + | + |
| 541 | GCUCCCAGGggctagctacaacgaGAAGUCACC | 30 | + | – |
| 603 | ATCCCGGCtccgagccggacgaCGCCGGGGC | 31 | – | + |

TABLE 2-continued

DNAzymes targeting human p21 mRNA

| DNAzyme Name (Dz) | DNAzyme sequence | SEQ ID NO: | Validated cleavage | Validated cytotoxicity |
|---|---|---|---|---|
| 835 | AGGGCTTCtccgagccggacgaCTTGGAGAA | 32 | − | + |
| 846 | GTGGGCGGAggctagctacaacgaTAGGGCTTC | 33 | + | + |
| 857 | GCAGGCTTtccgagccggacgaTGTGGGCGG | 34 | + | + |
| 974 | GGGTATGTAggctagctacaacgaATGAGGAGG | 35 | + | + |
| 985 | GGGGGCGGtccgagccggacgaAGGGTATGT | 36 | + | + |
| 1003 | GCCAGAGGtccgagccggacgaGGGGGGCAG | 37 | + | + |
| 1013 | TAATTCTAAggctagctacaacgaGCCAGAGGC | 38 | + | + |
| 1089 | TAAATAGTAggctagctacaacgaTTCATAAAA | 39 | − | + |
| 1114 | AGGAGAACAggctagctacaacgaGGGAUGAGG | 40 | + | + |
| 1116 | AAAGGAGAAggctagctacaacgaACGGGAUGA | 41 | + | − |
| 1252 | GGGGGTGAAggctagctacaacgaTTCATAACC | 42 | + | + |
| 1417 | GCTCAGCCtccgagccggacgaAGGCTGTGC | 43 | − | + |
| 1418 | AGCTCAGCtccgagccggacgaTAGGCTGTG | 44 | − | + |
| 1455 | AGGGGGGTAggctagctacaacgaCAAGAGCCA | 45 | + | + |
| 1467 | TTCACAAGAggctagctacaacgaAGAGGGGGG | 46 | + | + |
| 1504 | GGGGTGGTtccgagccggacgaGCTCCAGGA | 47 | + | + |
| 1524 | GAGGGGCCAggctagctacaacgaGAGGGCAGG | 48 | + | + |
| 1582 | CAGGGGAGtccgagccggacgaAAAGAGGGA | 49 | − | + |
| 1591 | CAAAAGGTAggctagctacaacgaAGGGGAGCC | 50 | − | + |
| 1602 | CTGGGGCTtccgagccggacgaTCAAAAGGT | 51 | − | + |
| 1610 | AAGGGTAGtccgagccggacgaGGGGCTCCT | 52 | − | + |
| 1641 | AGAGGGGAAggctagctacaacgaTGCAGAGCC | 53 | + | + |
| 1670 | GGGAAAGGAggctagctacaacgaAAGGGGGAG | 54 | + | + |
| 1683 | AGAGGGTAtccgagccggacgaGAAGGGAAA | 55 | + | + |
| 1684 | GAGAGGGTAggctagctacaacgaTGAAGGGAA | 56 | + | + |
| 1719 | GGGGTGGGAggctagctacaacgaAGGCACCTC | 57 | + | + |
| 1736 | CCATTGAGtccgagccggacgaGGGGGTGGG | 58 | + | + |
| 1742 | TCCAGTCCAggctagctacaacgaTGAGCTGGG | 59 | + | + |
| 1786 | GAGGTAGAAggctagctacaacgaTAGGGTGCC | 60 | + | + |
| 1791 | UGCCUGAGGggctagctacaacgaAGAACUAGG | 61 | − | + |
| 1800 | UGCUUGAGtccgagccggacgaGCCUGAGGU | 62 | − | + |
| 1838 | GGACCCTCAggctagctacaacgaCCCCACAGC | 63 | + | + |
| 1851 | GTGCCACCAggctagctacaacgaATGGGACCC | 64 | + | + |
| 1854 | CCTGTGCCAggctagctacaacgaCACATGGGA | 65 | + | + |
| 1872 | TAACCCCAtccgagccggacgaCAAGGGGGC | 66 | − | + |
| 1873 | ATAACCCCAggctagctacaacgaTCAAGGGGG | 67 | − | + |
| 1938 | TTTGAGGGGggctagctacaacgaCAGTGTCTC | 68 | − | + |

TABLE 2-continued

DNAzymes targeting human p21 mRNA

| DNAzyme Name (Dz) | DNAzyme sequence | SEQ ID NO: | Validated cleavage | Validated cytotoxicity |
|---|---|---|---|---|
| 1947 | GCTGGACGAggctagctacaacgaTTGAGGGGC | 69 | + | + |
| 1967 | TGGGGTGGAggctagctacaacgaGAGGAAGGT | 70 | + | + |
| 1976 | GGGGAGGGAggctagctacaacgaGGGGTGGAT | 71 | + | + |
| 1986 | GCAATGAAtccgagccggacgaGGGGAGGGA | 72 | + | + |
| 1987 | TGCAATGAAggctagctacaacgaTGGGGAGGG | 73 | + | + |
| 1991 | AAAGTGCAAggctagctacaacgaGAACTGGGG | 74 | + | + |
| 2200 | AGGCCAGTAggctagctacaacgaGTTACAGGA | 75 | − | + |
| 2215 | GAGAGAAAAggctagctacaacgaAGTCCAGGC | 76 | − | + |
| 2235 | ACCAGGACAggctagctacaacgaATGGGGAGC | 77 | − | + |
| 2266 | AGAGGTTTAggctagctacaacgaAGTCTAGGT | 78 | + | + |

Of note:
high case letters pertain to the two recognition arms of DNAzyme that bind the mRNA sequence and the low case letters pertain to the catalytic core which cleaves the target mRNA. DNAzyme names relate to their cleavage site position on the p21 mRNA (as set forth in SEQ ID NO: 1)

Both fluorescent microscopy and flow-cytometry were next utilized to trace the action of p21-targeting DNAzymes (e.g. DNAzyme 1114, DNAzyme 1670 and DNAzyme 985) from cellular uptake, through p21 mRNA and protein down-regulation, and up to induction of senescent cell death (FIGS. 5A-J and 11A-C). Specifically, p21 mRNA levels were significantly reduced over time following treatment with DNAzymes, reaching a knockdown of 57% and 73% for DNAzyme 1670 and DNAzyme 985, respectively (FIG. 5D). Following 48 hour treatment, p21 protein levels were significantly reduced following treatment with DNAzyme 1670 as compared to control scramble (FIG. 5G).

It has been shown that upon p21 knockdown, senescent cells acquired multiple DNA lesions that activated ataxia telangiectasia mutated (ATM) and nuclear factor (NF)-κB kinase, leading to decreased cell survival. Wherein NF-κB activation induces TNF-α secretion and JNK activation to mediate death of senescent cells in a caspase- and JNK-dependent manner [Yosef, R. et al. EMBO J. (2017) 36: 2280-2295]. As expected, following p21-targeting DNAzyme treatment, the senescent cells acquired DNA damage foci as can be seen by significantly elevated levels of γH2AX and p53BP1 staining (FIGS. 11A-C). Accumulation of DNA damage forced the cells into death by apoptosis involving significant activation of cleaved caspase-3 (CC3, FIG. 5J).

These results validated that senescent cells could be eliminated by targeting p21 mRNA using the specific DNAzymes. Of the 72 DNAzymes tested, 34 were found to target p21 mRNA for cleavage in vitro and showed senolytic activity (see Table 2, above).

Namely, DNAzyme 354 (SEQ ID NO: 23), DNAzyme 495 (SEQ ID NO: 29), DNAzyme 541 (SEQ ID NO: 30), DNAzyme 846 (SEQ ID NO: 33), DNAzyme 857 (SEQ ID NO: 34), DNAzyme 974 (SEQ ID NO: 35), DNAzyme 985 (SEQ ID NO: 36), DNAzyme 1003 (SEQ ID NO: 37), DNAzyme 1013 (SEQ ID NO: 38), DNAzyme 1114 (SEQ ID NO: 40), DNAzyme 1116 (SEQ ID NO: 41), DNAzyme 1252 (SEQ ID NO: 42), DNAzyme 1455 (SEQ ID NO: 45), DNAzyme 1467 (SEQ ID NO: 46), DNAzyme 1504 (SEQ ID NO: 47), DNAzyme 1524 (SEQ ID NO: 48), DNAzyme 1641 (SEQ ID NO: 53), DNAzyme 1670 (SEQ ID NO: 54), DNAzyme 1683 (SEQ ID NO: 55), DNAzyme 1684 (SEQ ID NO: 56), DNAzyme 1719 (SEQ ID NO: 57), DNAzyme 1736 (SEQ ID NO: 58), DNAzyme 1742 (SEQ ID NO: 59), DNAzyme 1786 (SEQ ID NO: 60), DNAzyme 1838 (SEQ ID NO: 63), DNAzyme 1851 (SEQ ID NO: 64), DNAzyme 1854 (SEQ ID NO: 65), DNAzyme 1947 (SEQ ID NO: 69), DNAzyme 1967 (SEQ ID NO: 70), DNAzyme 1976 (SEQ ID NO: 71), DNAzyme 1986 (SEQ ID NO: 72), DNAzyme 1987 (SEQ ID NO: 73), DNAzyme 1991 (SEQ ID NO: 74), and DNAzyme 2266 (SEQ ID NO: 78), were validated for mediating cleavage of p21 mRNA.

Of these 34 DNAzymes, 32 also showed senolytic activity (as illustrated by cytotoxicity). Specifically, DNAzymes 541 and 1116 did not show senolytic activity. Moreover, DNAzymes 1114, 1670, 985 and 1987 showed exceptional capabilities in both mediating cleavage of p21 mRNA and in senolytic activity.

Example 2

Efficacy and Selectivity of p21-Targeting DNAzymes

Figure 6B:
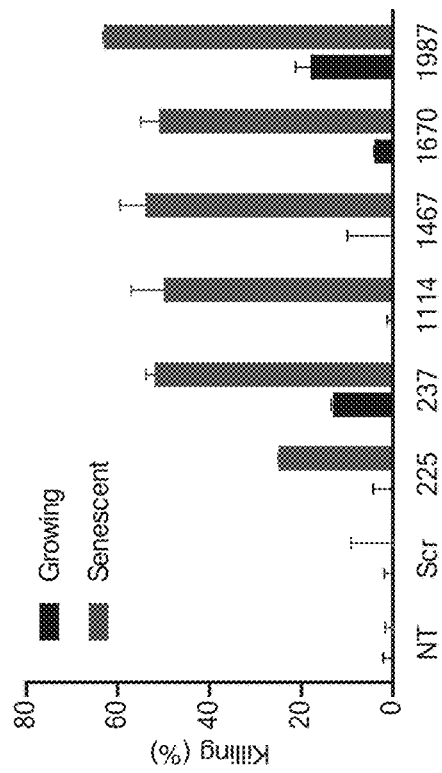
FIGS. 6A-D illustrate that p21 mRNA-targeting DNAzymes show specific and efficient killing of senescent cells.
Figure 6D:
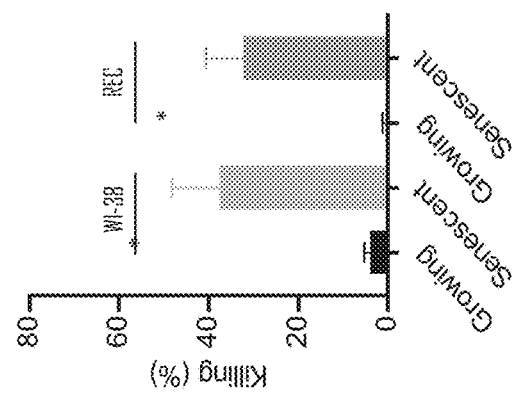
Figure 6A:
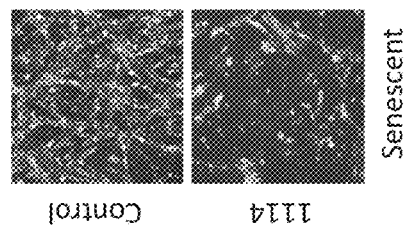
Figure 6C:
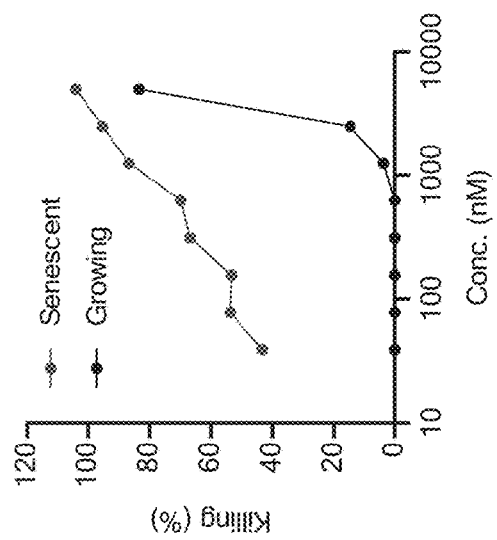

To demonstrate that induction of cell death by p21-targeting DNAzymes is indeed selective to senescent cells, DNAzymes were incubated with Human IMR-90 fibroblast cells and showed that these were effectively killed only when induced to senesce (FIGS. 6A-C). Furthermore, time course killing analysis validated this effect as selective for senescent cells (FIG. 12A). Off target nonspecific effects or other causes of toxicity are often dose related. To assess the optimal dosing window, killing assays were performed with increasing concentrations of the DNAzyme 1670 and DNAzyme 985. After five days in culture, both DNAzymes demonstrated a wide range of selective doses which could be utilized for safe and effective killing of senescent cells (FIGS. 12B-C).

Cellular senescence has been implicated in a variety of age-related diseases and therefore cell types from different organs are relevant for therapeutic applications. In addition to IMR-90 lung fibroblasts, p21-targeting DNAzymes showed a cell type independent senolytic activity as their action on senescent lung fibroblasts (WI-38) (FIG. 6D), on senescent BJ foreskin fibroblasts (FIG. 12D), and on senescent epithelial kidney cells (REC) (FIG. 6D) was both effective and selective.

In addition, cellular senescence can be induced by various stress mechanisms such as DNA damage, replicative exhaustion, oncogene activation, and more. Using these different stimuli and conditions the significant relevance of the p21-targeting DNAzymes was demonstrated in both replicative induced senescence (RIS) and oncogene induced senescence (OIS) (FIG. 12E). To explore the applicability of p21-targeting DNAzymes in therapy induced senescence (TIS), the combination treatment of sub-clinical chemotherapy dose with DNAzyme 1670 on several cancer cell lines was evaluated (FIG. 12F). The efficacy of sub-clinical Etoposide in combination with DNAzyme 1670 was comparable to that of clinical Etoposide dose enabling chemotherapy to be equally effective in-vitro at $\frac{1}{10}^{th}$ to $\frac{1}{100}^{th}$ of its nominal effective original dose (FIG. 12F). Combination treatment of Etoposide and DNAzyme 1670 yielded good synergistic results in the liver cancer cell line HepG2 (FIG. 12F). Next, sub-clinical doses of various chemotherapies in combination with DNAzyme 1670 were tested (FIG. 12G) and illustrated synergistic activity in HepG2 cells. Taken together, p21-targeting DNAzymes showed broad spectrum senolytics which display multipotency in various cell contexts.

Figure 15C:
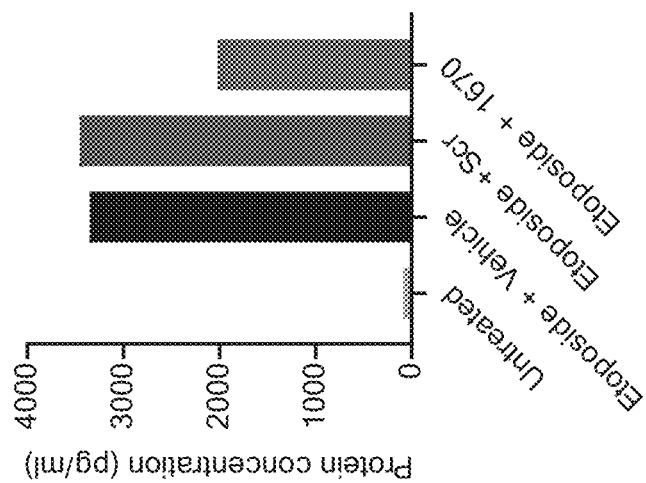
FIGS. 15A-C illustrate that p21 upregulation in chemotherapy induced senescence (CIS) is blocked by p21-targeting DNAzyme.
Figure 15B:
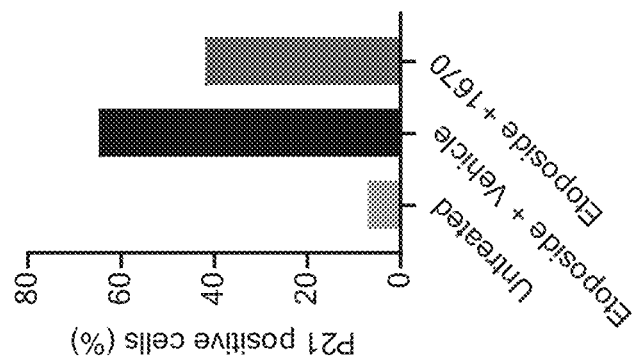
Figure 15A:
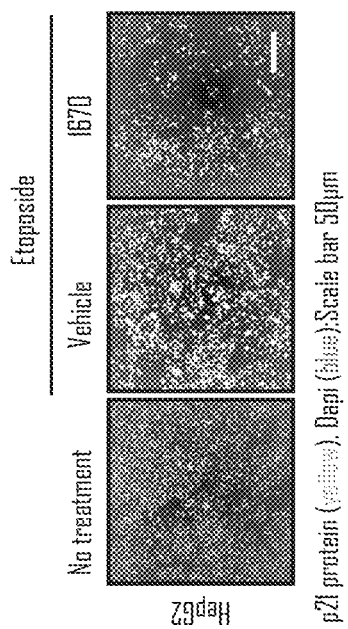
Figure 16B:
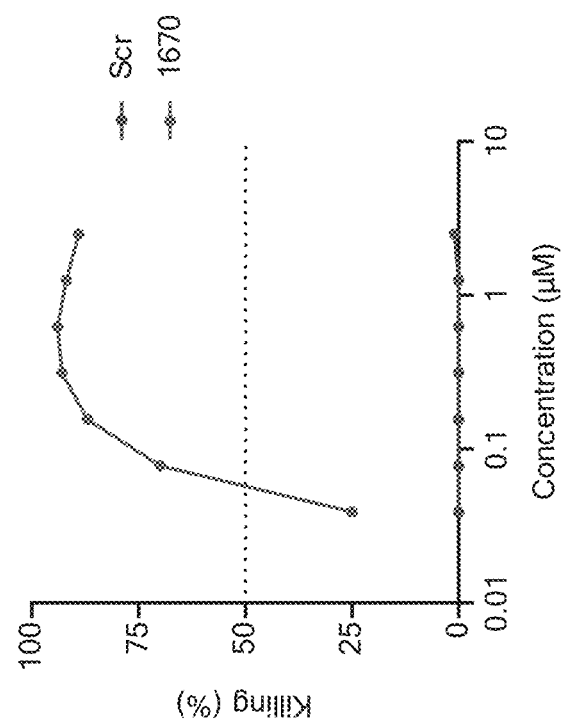
FIGS. 16A-B illustrate killing of HepG2 cells by p21-targeting DNAzymes.
Figure 16A:
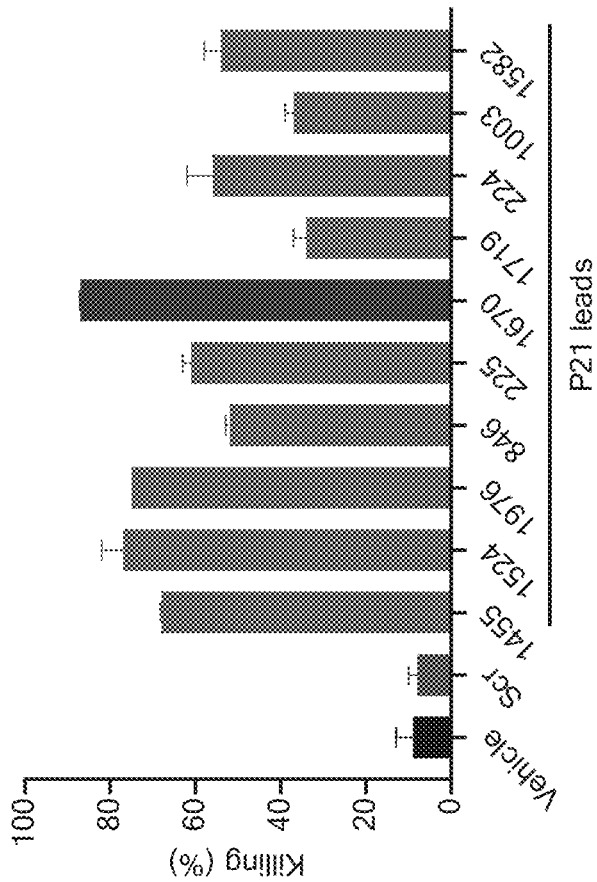

To validate that the senolytic efficacy was exerted by downregulation in p21 levels, HepG2 cells were stained immuno-fluorescently for p21 protein. As evident in FIGS. 15A-B, there was a significant decrease in staining in HepG2 cells treated with DNAzyme 1670. These results were further validated in a more quantitative analysis using p21 ELISA (FIG. 15C). In addition, other DNAzymes were demonstrated to have a strong senolytic effect in HepG2 cells induced to senescence by chemotherapy induced senescence (CIS) (FIG. 16A). Furthermore, one of the tested DNAzymes, i.e. DNAzyme 1670, exerted senolytic effect in a wide range of doses while control scramble did not (FIG. 16B).

Example 3

Stability and Biodistribution of p21-Targeting DNAzymes

Oligonucleotide therapy is notoriously prone to circulating exonuclease-mediated degradation. Therefore, protecting DNAzyme, such as in the serum and in lung compartments, would have a major pharmacological relevance for clinical applications. Unmodified DNAzyme 1670 was degraded over time in serum and Bronchoalveolar lavage fluid (BALF, FIG. 13A). Whereas in BALF, a reduction in the size of the DNAzyme was observed (below full length starting 24 hours from the start of incubation), in serum, the DNAzyme was completely degraded 48 hours from the start of incubation (FIG. 13A). One solution to increase the in vivo stability of DNAzymes is to add a 3' protective modification.

Figure 7A:
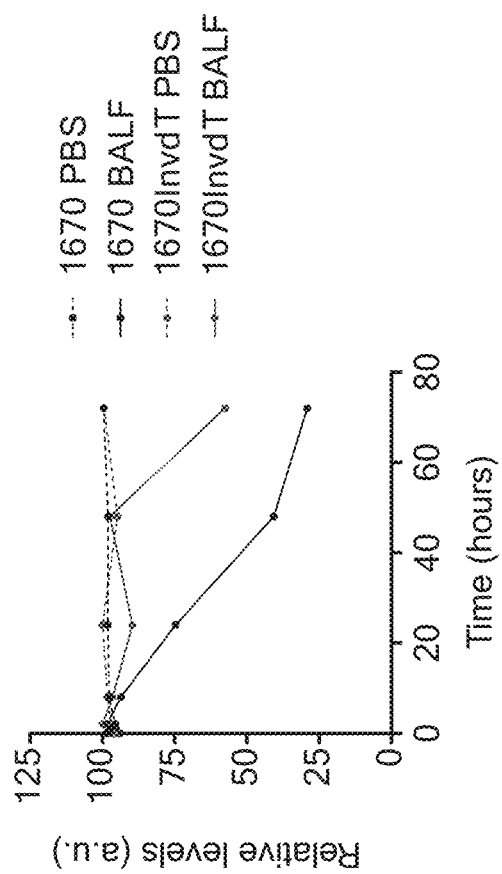
FIGS. 7A-B illustrate DNAzyme improvements.
Figure 7B:
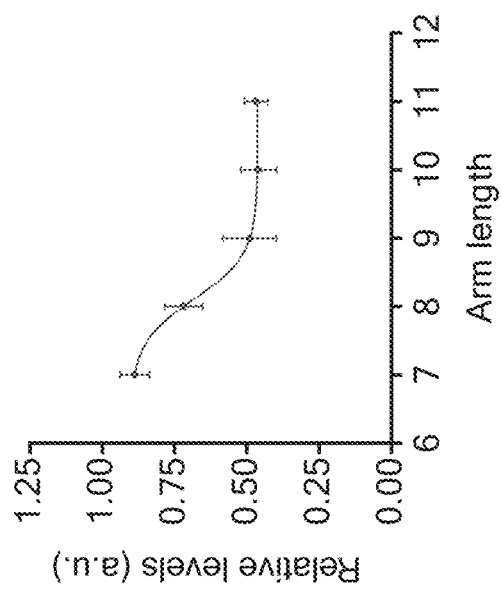

To improve the stability and efficacy of the specific DNAzymes, the effect of an increase in the length of the DNA recognition arms was tested. Indeed, elongation by 1-2 nucleotides showed a concomitant increase in cleavage in vitro of the p21 mRNA (FIG. 7A). Stability in bronchalveolar lavage fluid (BALF) was also increased by the addition of a 3-3' inverted dT modification which protects the DNAzyme from the 3' exonuclease activity of serum-borne exonucleases (FIG. 7B). Kinetics in stability assays showed that the incorporation of a 3' inverted dT modification significantly increased the time to degradation of DNAzyme 1670 in both serum and BALF (FIGS. 13B-C, respectively). The stability of DNAzyme 1670 in BALF from diseased bleomycin induced mice, an accepted pre-clinical efficacy mouse model for idiopathic pulmonary fibrosis (IPF), was also tested. As expected, stability in BALF of diseased mice was lower compared to naive BALF (FIG. 13C).

Figure 13D:
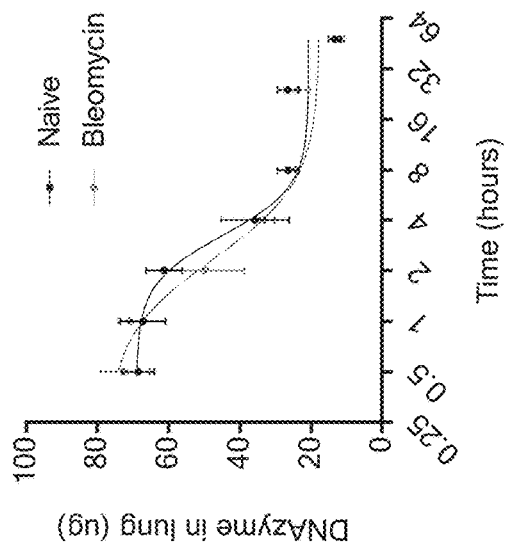
FIG. 13D: Long term kinetics of DNAzyme 1670 biodistribution in the lung over time. Quantification of signal in the lung of 5' Cy5.5-labeled and 3' inverted dT modified-DNAzyme 1670 after intratracheal administration in naïve and bleomycin-treated (at day 7 post treatment) mice—using image analysis software. Error bars are SEM.

A key aspect of the applicability of any drug is its capacity to reach the target organ with minimal off-target distribution, and its mode of clearance from the body. Mice were treated with Cy5.5-labeled DNAzyme 1670 comprising a 3'Inverted dT (200 µg) via the intratracheal route and Cy5.5-labeling was monitored in the mice lungs. Image intensity in the lung overtime showed an essentially identical profile for both naive and bleomycin-treated mice (FIG. 13D).

Example 4

Safety of p21-Targeting DNAzymes

Figure 13E:
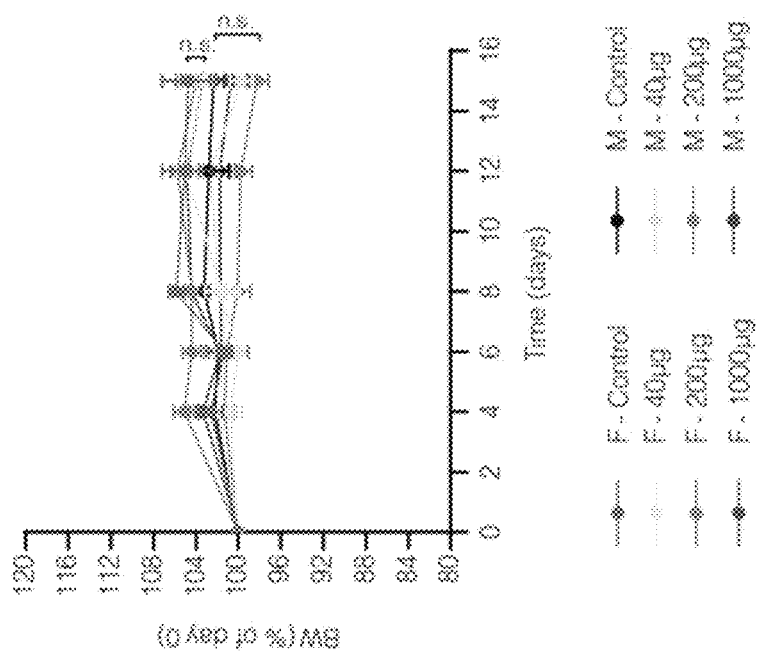
FIG. 13E: Experimental paradigm of an in-vivo safety study of DNAzyme 1670 using healthy C57/B6 mice of both sexes.
Figure 13F:
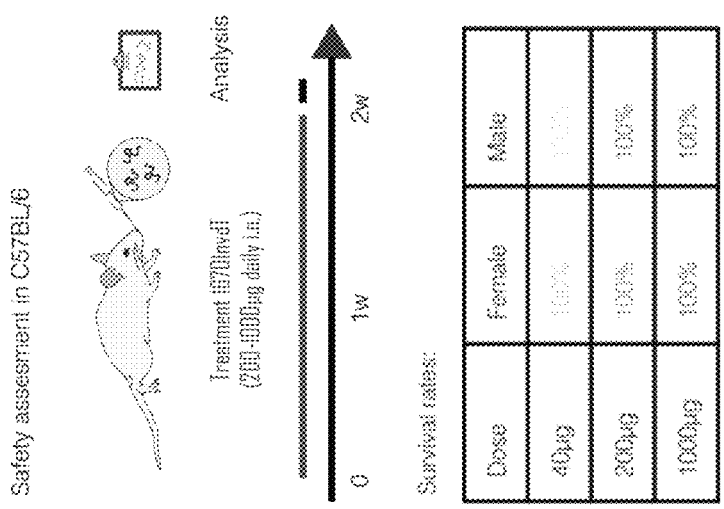
FIG. 13F: Body weight index (percent of day 0) during the safety experiment. Error bars are SEM.

A preclinical safety experiment was performed with DNAzyme 1670. In this experiment, healthy mice of both sexes (female n=3, male n=3) were intranasally treated with 40, 200, and 1000 micrograms of DNAzyme 1670 comprising a 3'Inverted dT daily for a time period of 2 weeks (FIG. 13E). There were no significant differences in body weight between groups (FIG. 13F) and no obvious signs of pain or distress. Blood tests were performed at the 2 week endpoint and these demonstrated a safe profile associated with the administration of the DNAzyme in both complete blood count (CBC, FIGS. 13G-O) and biochemistry parameters (data not shown).

Example 5

Specific Mouse p21 mRNA Targeting DNAzymes and their Effectivity In Vivo

DNAzymes hold a great promise for therapeutic applications due to their excellent programmability, stability, and activity. For evaluation of the therapeutic potential of p21 mRNA-targeting senolytic DNAzymes in vivo, specific DNAzymes were designed that efficiently cleave the mouse p21 mRNA sequence (as set forth in SEQ ID NO: 3, and presented in FIG. 8). The DNAzyme sequences and the location of the cleavage sites in mouse p21 mRNA are presented in Table 3, below.

Figure 9A:
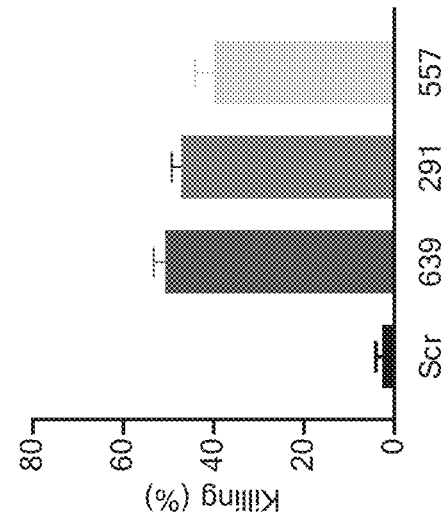
FIGS. 9A-B illustrate the establishment of mouse p21-targeting DNAzymes for in vivo studies.
Figure 9B:
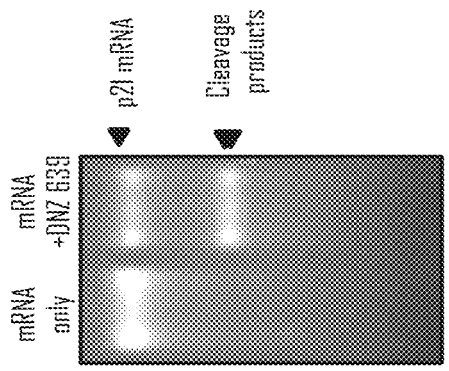

The mouse p21 specific DNAzymes were shown to be effective in in vitro cleaving of p21 mRNA, as show for example for Dz_639 (FIG. 9A). Moreover, three of the mouse p21 specific DNAzymes, namely Dz_639, Dz 291, and Dz_557 illustrated effective killing of mouse senescent cells (FIG. 9B).

TABLE 3

DNAzymes targeting mouse p21

| DNAzyme name (Dz) | DNAzyme sequence | SEQ ID NO: | Validated cleavage | Validated cytotoxicity |
|---|---|---|---|---|
| 557 | GAAGACCAAggctagctacaacgaCTGCGCTTG | 83 | + | + |
| 291 | GCTCCCAGAggctagctacaacgaGAAGTTGCC | 84 | + | + |
| 639 | GGCCGAAGAggctagctacaacgaGGGGAAGAG | 85 | + | + |

Of note:
high case letters pertain to the two recognition arms of DNAzyme that bind the mRNA sequence and the low case letters pertain to the catalytic core which cleaves the target mRNA. DNAzyme names relate to their cleavage site position on the p21 mRNA (as set forth in SEQ ID NO: 3)

Example 6

In Vivo Treatment of Idiopathic Pulmonary Fibrosis (IPF) in a Mouse Model Using p21-Targeting DNAzymes Senescent cells are implicated in various pathological processes, one of the most researched being tissue fibrosis. Idiopathic pulmonary fibrosis (IPF) is a fatal disease characterized by interstitial remodeling, leading to compromised lung function. For evaluation of the therapeutic potential of p21-targeting senolytic DNAzymes in-vivo, a commonly used and accepted mouse model of IPF was utilized wherein intratracheal injection of bleomycin induces lung fibrosis in mice. The mice were treated with either PBS (Sham. i.e. healthy mice), bleomycin alone (Vehicle), or bleomycin followed by intranasal treatment with Dz_639 in both therapeutic and prophylactic regimens (FIG. 10A). Two different treatment regimens were applied approximating prevention and therapeutic modalities. The difference being that the preventative regimen was initiated one day following bleomycin administration whereas the therapeutic regimen was initiated at day 7 following bleomycin administration, at a point when the fibrotic phase of the model has already initiated (FIG. 10A).

Figure 14A:
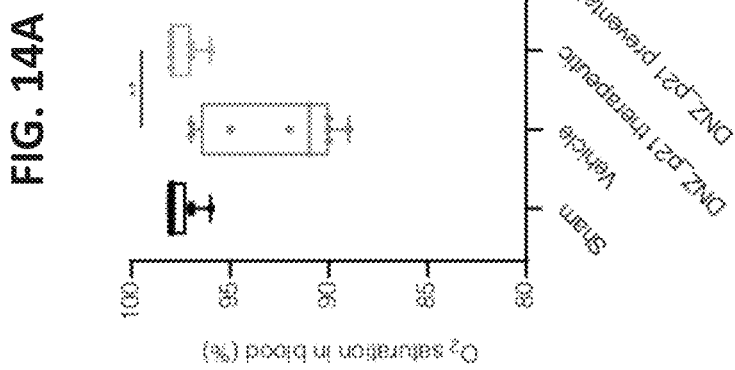
FIGS. 14A-F illustrate that p21-targeting DNAzyme ameliorates idiopathic pulmonary fibrosis (IPF) in a mouse disease model (following the schematic illustration of FIG. 10A).

As illustrated in FIG. 10C, the damage created in the lungs upon bleomycin insult was accompanied by a reduction in body weight. p21-targeting DNAzyme treatments (also referred to as Dnz_p21 or Dz_p21) were able to rescue the reduction in body weight following bleomycin administration, and the difference in body weights between the prophylactic group and the vehicle group was statistically significant at 21 days post-induction (p=0.0159). At 21 days, the mice were sacrificed and histological analysis (Aschcroft scoring of fibrosis) was performed on lung sections. The p21 mRNA-targeting DNAzyme treated mice displayed lower Aschroft fibrosis scores (p=0.0206) compared to the bleomycin treated group (FIG. 10B). Further analysis illustrated that oxygen saturation in the blood was significantly elevated following treatment with p21-targeting DNAzyme (FIG. 14A). Furthermore, treatment with p21-targeting DNAzyme significantly protected the mice from death as survival rates were increased from 75% in the vehicle group to 100% over 21 days both in the therapeutic and preventative regimens (FIG. 10D).

Figure 14C:
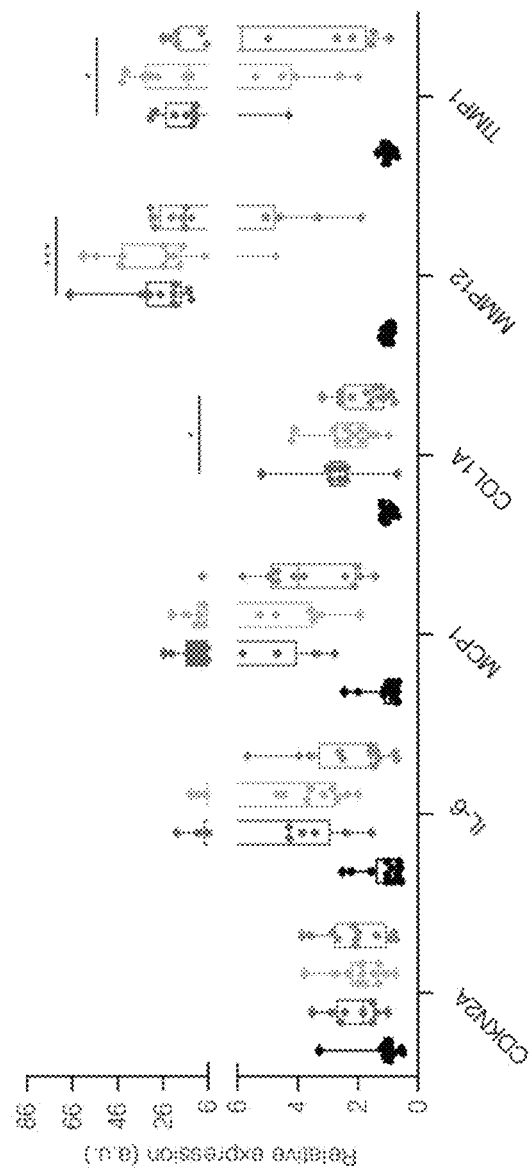
Figure 14B:
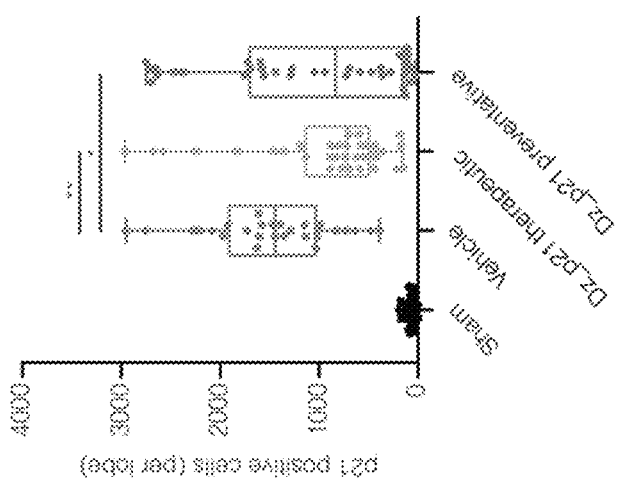

Treatment with p21-targeting DNAzyme showed a reduction in the number of p21 expressing cells in the lung tissue, in both treatment regimens as evident by expression analysis and IHC analysis of lung slices (FIG. 14B). Moreover, expression levels of senescence related genes and SASP factors were significantly reduced (FIG. 14C).

Accumulation of extracellular matrix components, such as collagen produced by fibroblasts, leads to the formation of a permanent fibrotic scar in IPF patients. Collagens play central roles in maintaining the organization and structural integrity of the lungs. Perturbation of collagen homeostasis is a major contributor to IPF development and maintenance. Evaluation of the levels of collagen and fibrosis were performed using several methods.

Figure 14F:
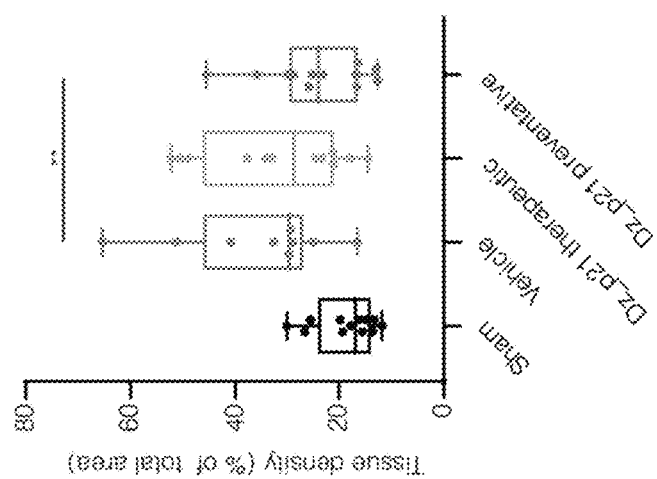
Figure 14E:
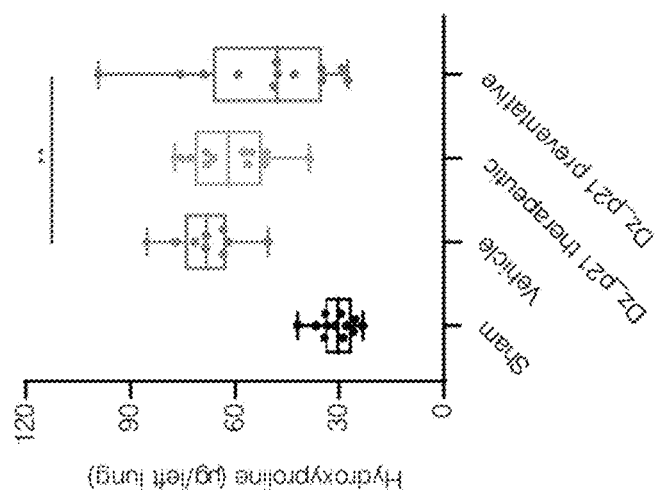
Figure 14D:
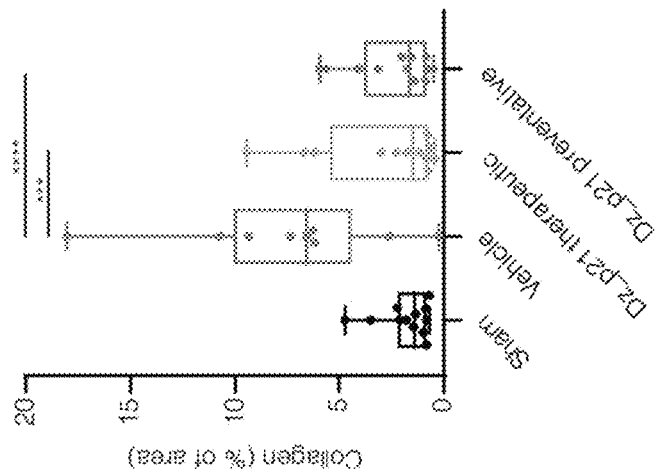

Evaluation of collagen levels was carried out using Masson's Trichrome staining of lung slices. As expected, bleomycin treated vehicle mice showed a significant increase in collagen levels, these levels were significantly reduced by both therapeutic and preventive regimens of p21-targeting DNAzyme treatments (FIG. 14D). Additionally, the levels of Hydroxyproline, a major component of fibrillar collagen of all types, were analyzed. Hydroxyproline levels were significantly increased as expected in bleomycin treated mice. Both therapeutic and preventative p21-targeting DNAzyme treatments reduced Hydroxyproline levels (FIG. 14E).

The accumulation of fibrotic content in the lungs can also be demonstrated by a tissue density which can lead to devastating consequences on lung function. Treatment with therapeutic and preventative p21-targeting DNAzyme reduced the tissue density (FIG. 14F) in both therapeutic and preventive treatment groups. Taken together these data demonstrate that a p21-targeting DNAzyme can ameliorate IPF in a mouse disease model.

Example 7

In Vivo Treatment of Unilateral Ureteral Obstruction (UUO) in a Mouse Model Using p21-Targeting DNAzymes Chronic kidney disease (CKD) is a common fibrotic age-related disease which creates increasing health burden. The accumulation of senescent cells has been implicated in the establishment of kidney fibrosis by inhibiting regeneration, activating fibroblasts and promoting inflammation. Clearance of senescent cells results in improved kidney function in aged animals, highlighting senolytic as a promising approach for CKD treatment.

The Unilateral Ureteral Obstruction (UUO) model is utilized to cause renal fibrosis, activated by obstructed urine flow and tubular injury. Experimental UUO in rodents is believed to mimic human chronic obstructive nephropathy in an accelerated manner. Utilizing this model it was shown that p21-targeting DNAzymes (DNZ_p21) not only significantly reduced the weight of the obstructed kidney (FIG. 17A) but also reduced the fibrotic extent in the kidney (FIG.

17B). This data further illustrated the therapeutic benefit that can be achieved by p21-targeting DNAzymes as senolytics.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A DNAzyme molecule comprising the nucleic acid sequence as set forth in SEQ ID NO: 54.

2. The DNAzyme of claim 1, wherein said nucleic acid sequence further comprises a modification that increases the stability or prevents degradation of the DNAzyme molecule.

3. The DNAzyme of claim 2, wherein said modification comprises an edge-blocker oligonucleotide.

4. The DNAzyme of claim 2, wherein said modification comprises an inverted deoxythymidine (dT) positioned at the 3' end of the DNAzyme molecule.

5. The DNAzyme of claim 1, wherein said DNAzyme molecule is attached to a heterologous moiety.

6. The DNAzyme of claim 5, wherein the heterologous moiety comprises a cell-targeting moiety or a cell-penetrating moiety.

7. The DNAzyme of claim 6, wherein the cell-targeting moiety is an affinity moiety.

8. The DNAzyme of claim 6, wherein the cell-targeting moiety binds to a senescent cell specific cell surface polypeptide.

9. The DNAzyme of claim 6, wherein the cell-targeting moiety binds to a cancer cell specific cell surface polypeptide.

10. A pharmaceutical composition comprising the DNAzyme of claim 1 and a pharmaceutically acceptable carrier.

11. A method of treating a disease in a subject in need thereof, said disease selected from a senescence-associated disease or disorder, a cancer, or a fibrotic disease or disorder, the method comprising administering to the subject a therapeutically effective amount of a DNAzyme molecule, said DNAzyme molecule comprising a nucleic acid sequence as set forth in SEQ ID NO: 54, wherein said administration treats said disease.

12. The method of claim 11, wherein when said disease is a senescence-associated disease or disorder, or a cancer, said method eradicates senescent cells or cancer cells, respectively.

13. The method of claim 11, wherein said senescence-associated disease or disorder is selected from the group consisting of an age-related disease or disorder, a neurological disease or disorder, a neurodegenerative disease or disorder, a cardiovascular disease or disorder, a pulmonary disease or disorder, an inflammatory disease or disorder, an autoimmune disease or disorder, a metabolic disease or disorder, a hepatic disease or disorder, a dermatological disease or disorder, an eye disease or disorder, a fibrotic disease or disorder, a cardiac disease or disorder, a vascular disease or disorder, a renal disease or disorder, and a cancer.

14. The method of claim 13, wherein said cancer is a therapy-resistant cancer.

15. The method of claim 11, wherein said fibrotic disease or disorder is selected from the group consisting of a pulmonary fibrosis, a liver fibrosis, a kidney fibrosis, a pancreatic fibrosis, a cardiac fibrosis, a scleroderma or systemic sclerosis, an oral submucosa fibrosis, an intestinal fibrosis, an eosinophilic esophagitis, hypereosinophilic syndromes (HES), and Loeffler's endomyocarditis or skin fibrosis.

16. The method of claim 11, wherein said administration comprises systemic, intranasal, inhalation, intracerebroventricular, intrathecal, oral, local injection, intratumoral, or intravenous administration.

17. The method of claim 11, wherein said subject is a human subject.

18. The method of claim 11, wherein said nucleic acid sequence further comprises a modification that increases the stability or prevents degradation of the DNAzyme molecule.

19. The method of claim 18, wherein said modification comprises an edge-blocker oligonucleotide or an inverted deoxythymidine (dT) positioned at the 3' end of the DNAzyme molecule.

20. The method of claim 11, wherein said DNAzyme molecule is attached to a heterologous moiety.

21. The method of claim 20, wherein the heterologous moiety comprises a cell-targeting moiety or a cell-penetrating moiety.

22. The method of claim 21, wherein the cell-targeting moiety is an affinity moiety, optionally binding to a senescent cell specific cell surface polypeptide or cancer cell specific cell surface polypeptide.

23. The method of claim 15, wherein when said fibrotic disease or disorder is said pulmonary fibrosis, said disease or disorder is idiopathic pulmonary fibrosis (IPF).

24. The method of claim 15, wherein when said fibrotic disease or disorder is said liver fibrosis, said disease or disorder is non-alcoholic steatohepatitis (NASH).

* * * * *

SEQUENCE LISTING

```
Sequence total quantity: 125
SEQ ID NO: 1            moltype = DNA  length = 2378
FEATURE                 Location/Qualifiers
source                  1..2378
                        mol_type = other DNA
                        organism = Homo sapiens
SEQUENCE: 1
atgttgagct ctggcataga agaggctggt ggctattttg tccttgggct gcctgttttc   60
aggtgaggaa ggggatggta ggagacagga gacctctaaa gaccccagaa ataaaggatg  120
acaagcagag agccccgggc aggaggcaaa agtcctgtgt tccaactata gtcatttctt  180
tgctgcatga tctgagttag gtcaccagac ttctctgagc cccagtttcc ccagcagtgt  240
atacgggcta tgtggggagt attcaggaga cagacaactc actcgtcaaa tcctcccctt  300
cctgccaac  aaagctgctg caaccacagg gatttcttct gttcaggcgc catgtcagaa  360
ccggctgggg atgtccgtca gaacccatgc ggcagcaagg cctgccgccg cctcttcggc  420
ccagtggaca gcgagcagct gagccgcgac tgtgatgcgc taatggcggg ctgcatccag  480
gaggcccgtg agcgatggaa cttcgacttt gtcaccgaga caccactgga gggtgacttc  540
gcctgggagc gtgtgcgggg ccttggcctg cccaagctct accttccac ggggcccgg   600
cgaggccggg atgagttggg aggaggcagg cggcctggca cctcacctgc tctgctgcag  660
gggacagcag aggaagacca tgtggacctg tcactgtctt gtaccccttgt gcctcgctca  720
ggggagcagg ctgaagggtc cccaggtgga cctggagact ctcagggtcg aaaacggcgg  780
cagaccagca tgacagattt ctaccactcc aaacgccggc tgatcttctc caagaggaag  840
ccctaatccg cccacaggaa gcctgcagtc ctggaagcgc gagggcctca aagcccgct   900
ctacatcttc tgccttagtc tcagtttgtg tgtcttaatt attatttgtg ttttaattta  960
aacacctcct catgtacata ccctggccgc ccctgcccc  ccagcctctg gcattagaat 1020
tatttaaaca aaaactaggc ggttgaatga gaggttccta agagtgctgg gcatttttat 1080
tttatgaaat actatttaaa gcctcctcat cccgtgttct ccttttcctc tctccggag  1140
gttgggtggg ccggcttcat gccagctact tcctcctccc cacttgtccg ctgggtggta 1200
ccctctggag gggtgtggct ccttcccatc gctgtcacag gcggttatga aattcaccc  1260
cttttcctgga cactcagacc tgaattcttt ttcatttgag aagtaaacag atggcacttt 1320
gaaggggcct caccgagtgg gggcatcatc aaaaactttg gagtccctc  acctcctcta 1380
aggttgggca gggtgaccct gaagtgagca cagcctaggg ctgagctggg gacctggtac 1440
cctcctggct cttgatacc cctctgtct tgtgaagtga gggggaaggt gggggtcctg 1500
agcagaccac cccgcctgcc ctcatggccc ctctgacctg cactggggag cccgtctcag 1560
tgttgagcct tttcctctt tggctcccct gtaccttttg aggagcccca gctaccttt  1620
ttctccagct gggctctgca attcccctct gctgctgtcc ctcccccttg tcctttcct  1680
tcagtaccct ctcagctcca ggtggctctg aggtgcctgt cccaccccca ccccccagctc 1740
aatggactgg aaggggaagg gacacacaag aagaagggca ccctagttct acctcaggca 1800
gctcaagcag cgaccgcccc ctcctctagc tgtgggggtg agggtcccat gtggtggcac 1860
aggcccccctt gagtgggggtt atctctgtgt taggggtata tgatggggga gtagatcttt 1920
ctaggaggga gacactggcc cctcaaatcg tccagcgacc ttcctcatcc accccatccc 1980
tccccagttc attgcactttt gattagcagc ggaacaagga gtcagacatt ttaagatggt 2040
ggcagtagag gctatggaca gggcatgcca cgtgggctca tatggggctg ggagtagttg 2100
tctttcctgg cactaacgtt gagccccctgg aggcactgaa gtgcttagtg tacttggagt 2160
attggggtct gaccccaaac accttccagc tcctgtaaca tactggcctg gactgttttc 2220
tctcggctcc ccatgtgtcc tggttccccgt ttctccacct agactgtaaa cctctcgagg 2280
gcagggacca caccctgtac tgttctgtgt ctttcacagc tcctcccaca atgctgaata 2340
tacagcaggt gctcaataaa tgattcttag tgacttta                          2378

SEQ ID NO: 2            moltype = AA  length = 198
FEATURE                 Location/Qualifiers
source                  1..198
                        mol_type = protein
                        organism = Homo sapiens
SEQUENCE: 2
MWGVFRRQTT HSSNPPLPGQ QSCCNHRDFF CSGAMSEPAG DVRQNPCGSK ACRRLFGPVD   60
SEQLSRDCDA LMAGCIQEAR ERWNFDFVTE TPLEGDFAWE RVRGLGLPKL YLPTGPRRGR  120
DELGGGRRPG TSPALLQGTA EEDHVDLSLS CTLVPRSGEQ AEGSPGGPGD SQGRKRRQTS  180
MTDFYHSKRR LIFSKRKP                                                198

SEQ ID NO: 3            moltype = DNA  length = 1913
FEATURE                 Location/Qualifiers
source                  1..1913
                        mol_type = other DNA
```

```
                        organism = Mus musculus
SEQUENCE: 3
tgcagcagcc gagaggtgtg agccgccgcg gtgtcagagt ctaggggaat tggagtcagg    60
cgcagatcca cagcgatatc cagacattca gagccacagg caccatgtcc aatcctggtg   120
atgtccgacc tgttccgcac aggagcaaag tgtgccgttg tctcttcggt cccgtggaca   180
gtgagcagtt gcgccgtgat tgcgatgcgc tcatggcggg ctgtctccag gaggcccgag   240
aacggtggaa ctttgacttc gtcacggaga cgccgctgga gggcaacttc gtctgggagc   300
gcgttcggag cctagggctg cccaaggtct acctgagccc tggtcccgc agccgtgacg    360
acctgggagg ggacaagagg cccagtactt cctctgccct gctgcagggg ccagctccgg   420
aggaccacgt ggccttgtcg ctgtcttgca ctctggtgtc tgagcggcct gaagattccc   480
cgggtgggcc cggaacatct cagggccgaa aacgtgaggca gaccagcctg acagatttct   540
atcactccaa gcgcagattg gtcttctgca agagaaaacc ctgaagtgcc cacgggagcc   600
ccgcccctct ctgctgtggg tcaggaggcc tcttccccat cttcggccgctt agccctcact   660
ctgtgtgtct taattattat ttgtgttta atttaaacgt ctcctgtata tacgctgcct    720
gccctctccc agtctccaaa cttaaagtta tttaaaaaaa gaacaaaaca aaacaaaaaa   780
aaccaaaaca aaacaaacct aaattagtag gacggtaggg ccttagtgt ggggggatttc   840
tattatgtag attattatta tttaagcccc tcccaaccca agctctgtgt ttcctatacc   900
ggaggaacag tcctactgat atcaacccat ctgcatccgt ttcacccaac cccctctccc   960
ccattccctg cctggttcct tgccacttct tacctggggg tgatcctcag acctgaatag  1020
cactttggaa aaatgagtag gactttgggg tctccttgtc acctcaagg ccagctagga   1080
tgacagtgaa gcagtcacag cctagaacag ggatggcagt taggactcaa ccgtaatatc  1140
ccgactcttg acattgctca gacctgtgaa gacaggaatg gtccccactc tggatcccct  1200
ttgccactcc tggggagccc acctctcctg tgggtctctg ccagctgccc ctctatttt   1260
gagggttaat ctggtgatct gctgctcttt tcccccaccc catacttccc cttctgcagg  1320
tcggcaggag gcatatctag gcacttgccc cacagctcag tggactggaa gggaatgtat  1380
atgcagggta cactaagtgg gattccctgg tcttaccttaa ggcagctcag gtggcaaccc  1440
cctgcattgt gggtctaggg tgggtccttg gtggtgagac aggcctccca gagcattcta  1500
tggtgtgtgg tggtggggt gggcttatct gggatgggga ccccagttgg ggttctcagt  1560
gacttctccc atttcttagt agcagttgta caaggagcca ggccaagatg gtgtcttggg  1620
ggctaaggga gctcacagga cactgagcaa tggctgatcc tttctcagtg ttgaataccg  1680
tgggtgtcaa agcacttagt gggtctgact ccagcccaa acatcccgt ttctgtaaca   1740
tcctggtctg gactgtctac ccttagcccg caccccaaga acatgtattg tggctccctc  1800
cctgtctcca ctcagattgt aagcgtctca cgagaaggga cagcaccctg cattgtcccg  1860
agtcctcaca cccgacccca aagctggtgc tcaataaata cttctcgatg att          1913

SEQ ID NO: 4           moltype = AA  length = 159
FEATURE                Location/Qualifiers
source                 1..159
                        mol_type = protein
                        organism = Mus musculus
SEQUENCE: 4
MSNPGDVRPV PHRSKVCRCL FGPVDSEQLR RDCDALMAGC LQEARERWNF DFVTETPLEG    60
NFVWERVRSL GLPKVYLSPG SRSRDDLGGD KRPSTSSALL QGPAPEDHVA LSLSCTLVSE   120
RPEDSPGGPG TSQGRKRRQT SLTDFYHSKR RLVFCKRKP                          159

SEQ ID NO: 5           moltype = DNA  length = 33
FEATURE                Location/Qualifiers
misc_feature           1..33
                        note = control DNZ_Scramble Arm
source                 1..33
                        mol_type = other DNA
                        organism = synthetic construct
SEQUENCE: 5
atcttccttg gctagctaca acgacgcctc tcc                                 33

SEQ ID NO: 6           moltype = DNA  length = 33
FEATURE                Location/Qualifiers
misc_feature           1..33
                        note = DNAzymes targeting human p21 mRNA
source                 1..33
                        mol_type = other DNA
                        organism = synthetic construct
SEQUENCE: 6
cctcttctag gctagctaca acgagccaga gct                                 33

SEQ ID NO: 7           moltype = DNA  length = 33
FEATURE                Location/Qualifiers
misc_feature           1..33
                        note = DNAzymes targeting human p21 mRNA
source                 1..33
                        mol_type = other DNA
                        organism = synthetic construct
SEQUENCE: 7
ctcctaccag gctagctaca acgaccccctt cct                                33

SEQ ID NO: 8           moltype = DNA  length = 33
FEATURE                Location/Qualifiers
misc_feature           1..33
                        note = DNAzymes targeting human p21 mRNA
```

```
source                      1..33
                            mol_type = other DNA
                            organism = synthetic construct
SEQUENCE: 8
tgtctcctag gctagctaca acgacatccc ctt                                 33

SEQ ID NO: 9                moltype = DNA   length = 31
FEATURE                     Location/Qualifiers
misc_feature                1..31
                            note = DNAzymes targeting human p21 mRNA
source                      1..31
                            mol_type = other DNA
                            organism = synthetic construct
SEQUENCE: 9
tctggggttc cgagccggac gattagaggt c                                   31

SEQ ID NO: 10               moltype = DNA   length = 33
FEATURE                     Location/Qualifiers
misc_feature                1..33
                            note = DNAzymes targeting human p21 mRNA
source                      1..33
                            mol_type = other DNA
                            organism = synthetic construct
SEQUENCE: 10
catcctttag gctagctaca acgattctgg ggt                                 33

SEQ ID NO: 11               moltype = DNA   length = 33
FEATURE                     Location/Qualifiers
misc_feature                1..33
                            note = DNAzymes targeting human p21 mRNA
source                      1..33
                            mol_type = other DNA
                            organism = synthetic construct
SEQUENCE: 11
gcaaagaaag gctagctaca acgagactat agt                                 33

SEQ ID NO: 12               moltype = DNA   length = 33
FEATURE                     Location/Qualifiers
misc_feature                1..33
                            note = DNAzymes targeting human p21 mRNA
source                      1..33
                            mol_type = other DNA
                            organism = synthetic construct
SEQUENCE: 12
cagatcatgg gctagctaca acgaagcaaa gaa                                 33

SEQ ID NO: 13               moltype = DNA   length = 31
FEATURE                     Location/Qualifiers
misc_feature                1..31
                            note = DNAzymes targeting human p21 mRNA
source                      1..31
                            mol_type = other DNA
                            organism = synthetic construct
SEQUENCE: 13
tggggaaatc cgagccggac gaggggctca g                                   31

SEQ ID NO: 14               moltype = DNA   length = 33
FEATURE                     Location/Qualifiers
misc_feature                1..33
                            note = DNAzymes targeting human p21 mRNA
source                      1..33
                            mol_type = other DNA
                            organism = synthetic construct
SEQUENCE: 14
ctggggaaag gctagctaca acgatggggc tca                                 33

SEQ ID NO: 15               moltype = DNA   length = 31
FEATURE                     Location/Qualifiers
misc_feature                1..31
                            note = DNAzymes targeting human p21 mRNA
source                      1..31
                            mol_type = other DNA
                            organism = synthetic construct
SEQUENCE: 15
cgtatacatc cgagccggac gagctgggga a                                   31

SEQ ID NO: 16               moltype = DNA   length = 33
FEATURE                     Location/Qualifiers
misc_feature                1..33
```

```
                        note = DNAzymes targeting human p21 mRNA
source                  1..33
                        mol_type = other DNA
                        organism = synthetic construct
SEQUENCE: 16
ccgtatacag gctagctaca acgatgctgg gga                                    33

SEQ ID NO: 17           moltype = DNA  length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 17
tactccccag gctagctaca acgaatagcc cgt                                    33

SEQ ID NO: 18           moltype = DNA  length = 31
FEATURE                 Location/Qualifiers
misc_feature            1..31
                        note = DNAzymes targeting human p21 mRNA
source                  1..31
                        mol_type = other DNA
                        organism = synthetic construct
SEQUENCE: 18
gtctgtcttc cgagccggac gatgaatact c                                      31

SEQ ID NO: 19           moltype = DNA  length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 19
aggggaggag gctagctaca acgattgacg agt                                    33

SEQ ID NO: 20           moltype = DNA  length = 31
FEATURE                 Location/Qualifiers
misc_feature            1..31
                        note = DNAzymes targeting human p21 mRNA
source                  1..31
                        mol_type = other DNA
                        organism = synthetic construct
SEQUENCE: 20
tttgttggtc cgagccggac gaaggaaggg g                                      31

SEQ ID NO: 21           moltype = DNA  length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 21
tggttgcagg gctagctaca acgaagcttt gtt                                    33

SEQ ID NO: 22           moltype = DNA  length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 22
gttctgacag gctagctaca acgaggcgcc tga                                    33

SEQ ID NO: 23           moltype = DNA  length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 23
cggttctgag gctagctaca acgaatggcg cct                                    33

SEQ ID NO: 24           moltype = DNA  length = 33
FEATURE                 Location/Qualifiers
```

```
misc_feature             1..33
                         note = DNAzymes targeting human p21 mRNA
source                   1..33
                         mol_type = other DNA
                         organism = synthetic construct
SEQUENCE: 24
tgacggacag gctagctaca acgaccccag ccg                                      33

SEQ ID NO: 25            moltype = DNA  length = 33
FEATURE                  Location/Qualifiers
misc_feature             1..33
                         note = DNAzymes targeting human p21 mRNA
source                   1..33
                         mol_type = other DNA
                         organism = synthetic construct
SEQUENCE: 25
gggttctgag gctagctaca acgaggacat ccc                                      33

SEQ ID NO: 26            moltype = DNA  length = 33
FEATURE                  Location/Qualifiers
misc_feature             1..33
                         note = DNAzymes targeting human p21 mRNA
source                   1..33
                         mol_type = other DNA
                         organism = synthetic construct
SEQUENCE: 26
gctgccgcag gctagctaca acgagggttc tga                                      33

SEQ ID NO: 27            moltype = DNA  length = 31
FEATURE                  Location/Qualifiers
misc_feature             1..31
                         note = DNAzymes targeting human p21 mRNA
source                   1..31
                         mol_type = other DNA
                         organism = synthetic construct
SEQUENCE: 27
aggccttgtc cgagccggac gagccgcatg g                                        31

SEQ ID NO: 28            moltype = DNA  length = 31
FEATURE                  Location/Qualifiers
misc_feature             1..31
                         note = DNAzymes targeting human p21 mRNA
source                   1..31
                         mol_type = other DNA
                         organism = synthetic construct
SEQUENCE: 28
agtcgcggtc cgagccggac gacagctgct c                                        31

SEQ ID NO: 29            moltype = DNA  length = 33
FEATURE                  Location/Qualifiers
misc_feature             1..33
                         note = DNAzymes targeting human p21 mRNA
source                   1..33
                         mol_type = other DNA
                         organism = synthetic construct
SEQUENCE: 29
gaagttccag gctagctaca acgacgctca cgg                                      33

SEQ ID NO: 30            moltype = DNA  length = 33
FEATURE                  Location/Qualifiers
misc_feature             1..33
                         note = DNAzymes targeting human p21 mRNA
source                   1..33
                         mol_type = other DNA
                         organism = synthetic construct
SEQUENCE: 30
gctcccaggg gctagctaca acgagaagtc acc                                      33

SEQ ID NO: 31            moltype = DNA  length = 31
FEATURE                  Location/Qualifiers
misc_feature             1..31
                         note = DNAzymes targeting human p21 mRNA
source                   1..31
                         mol_type = other DNA
                         organism = synthetic construct
SEQUENCE: 31
atcccggctc cgagccggac gacgccgggg c                                        31

SEQ ID NO: 32            moltype = DNA  length = 31
```

```
FEATURE                 Location/Qualifiers
misc_feature            1..31
                        note = DNAzymes targeting human p21 mRNA
source                  1..31
                        mol_type = other DNA
                        organism = synthetic construct
SEQUENCE: 32
agggcttctc cgagccggac gacttggaga a                                    31

SEQ ID NO: 33           moltype = DNA  length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 33
gtgggcggag gctagctaca acgatagggc ttc                                  33

SEQ ID NO: 34           moltype = DNA  length = 31
FEATURE                 Location/Qualifiers
misc_feature            1..31
                        note = DNAzymes targeting human p21 mRNA
source                  1..31
                        mol_type = other DNA
                        organism = synthetic construct
SEQUENCE: 34
gcaggctttc cgagccggac gatgtgggcg g                                    31

SEQ ID NO: 35           moltype = DNA  length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 35
gggtatgtag gctagctaca acgaatgagg agg                                  33

SEQ ID NO: 36           moltype = DNA  length = 31
FEATURE                 Location/Qualifiers
misc_feature            1..31
                        note = DNAzymes targeting human p21 mRNA
source                  1..31
                        mol_type = other DNA
                        organism = synthetic construct
SEQUENCE: 36
ggggcggtc cgagccggac gaagggtatg t                                     31

SEQ ID NO: 37           moltype = DNA  length = 31
FEATURE                 Location/Qualifiers
misc_feature            1..31
                        note = DNAzymes targeting human p21 mRNA
source                  1..31
                        mol_type = other DNA
                        organism = synthetic construct
SEQUENCE: 37
gccagaggtc cgagccggac gaggggggca g                                    31

SEQ ID NO: 38           moltype = DNA  length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 38
taattctaag gctagctaca acgagccaga ggc                                  33

SEQ ID NO: 39           moltype = DNA  length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 39
taaatagtag gctagctaca acgattcata aaa                                  33
```

```
SEQ ID NO: 40              moltype = DNA  length = 33
FEATURE                    Location/Qualifiers
misc_feature               1..33
                           note = DNAzymes targeting human p21 mRNA
source                     1..33
                           mol_type = other DNA
                           organism = synthetic construct
SEQUENCE: 40
aggagaacag gctagctaca acgagggatg agg                                    33

SEQ ID NO: 41              moltype = DNA  length = 33
FEATURE                    Location/Qualifiers
misc_feature               1..33
                           note = DNAzymes targeting human p21 mRNA
source                     1..33
                           mol_type = other DNA
                           organism = synthetic construct
SEQUENCE: 41
aaaggagaag gctagctaca acgaacggga tga                                    33

SEQ ID NO: 42              moltype = DNA  length = 33
FEATURE                    Location/Qualifiers
misc_feature               1..33
                           note = DNAzymes targeting human p21 mRNA
source                     1..33
                           mol_type = other DNA
                           organism = synthetic construct
SEQUENCE: 42
gggggtgaag gctagctaca acgattcata acc                                    33

SEQ ID NO: 43              moltype = DNA  length = 31
FEATURE                    Location/Qualifiers
misc_feature               1..31
                           note = DNAzymes targeting human p21 mRNA
source                     1..31
                           mol_type = other DNA
                           organism = synthetic construct
SEQUENCE: 43
gctcagcctc cgagccggac gaaggctgtg c                                      31

SEQ ID NO: 44              moltype = DNA  length = 31
FEATURE                    Location/Qualifiers
misc_feature               1..31
                           note = DNAzymes targeting human p21 mRNA
source                     1..31
                           mol_type = other DNA
                           organism = synthetic construct
SEQUENCE: 44
agctcagctc cgagccggac gataggctgt g                                      31

SEQ ID NO: 45              moltype = DNA  length = 33
FEATURE                    Location/Qualifiers
misc_feature               1..33
                           note = DNAzymes targeting human p21 mRNA
source                     1..33
                           mol_type = other DNA
                           organism = synthetic construct
SEQUENCE: 45
agggggggtag gctagctaca acgacaagag cca                                   33

SEQ ID NO: 46              moltype = DNA  length = 33
FEATURE                    Location/Qualifiers
misc_feature               1..33
                           note = DNAzymes targeting human p21 mRNA
source                     1..33
                           mol_type = other DNA
                           organism = synthetic construct
SEQUENCE: 46
ttcacaagag gctagctaca acgaagaggg ggg                                    33

SEQ ID NO: 47              moltype = DNA  length = 31
FEATURE                    Location/Qualifiers
misc_feature               1..31
                           note = DNAzymes targeting human p21 mRNA
source                     1..31
                           mol_type = other DNA
                           organism = synthetic construct
SEQUENCE: 47
ggggtggttc cgagccggac gagctccagg a                                      31
```

-continued

```
SEQ ID NO: 48           moltype = DNA   length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 48
gaggggccag gctagctaca acgagagggc agg                                33

SEQ ID NO: 49           moltype = DNA   length = 31
FEATURE                 Location/Qualifiers
misc_feature            1..31
                        note = DNAzymes targeting human p21 mRNA
source                  1..31
                        mol_type = other DNA
                        organism = synthetic construct
SEQUENCE: 49
caggggagtc cgagccggac gaaaagaggg a                                  31

SEQ ID NO: 50           moltype = DNA   length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 50
caaaaggtag gctagctaca acgaaggga gcc                                 33

SEQ ID NO: 51           moltype = DNA   length = 31
FEATURE                 Location/Qualifiers
misc_feature            1..31
                        note = DNAzymes targeting human p21 mRNA
source                  1..31
                        mol_type = other DNA
                        organism = synthetic construct
SEQUENCE: 51
ctggggcttc cgagccggac gatcaaaagg t                                  31

SEQ ID NO: 52           moltype = DNA   length = 31
FEATURE                 Location/Qualifiers
misc_feature            1..31
                        note = DNAzymes targeting human p21 mRNA
source                  1..31
                        mol_type = other DNA
                        organism = synthetic construct
SEQUENCE: 52
aagggtagtc cgagccggac gaggggctcc t                                  31

SEQ ID NO: 53           moltype = DNA   length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 53
agaggggaag gctagctaca acgatgcaga gcc                                33

SEQ ID NO: 54           moltype = DNA   length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 54
gggaaaggag gctagctaca acgaaagggg gag                                33

SEQ ID NO: 55           moltype = DNA   length = 31
FEATURE                 Location/Qualifiers
misc_feature            1..31
                        note = DNAzymes targeting human p21 mRNA
source                  1..31
                        mol_type = other DNA
                        organism = synthetic construct
SEQUENCE: 55
```

```
agagggtatc cgagccggac gagaagggaa a                                    31

SEQ ID NO: 56           moltype = DNA   length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 56
gagagggtag gctagctaca acgatgaagg gaa                                  33

SEQ ID NO: 57           moltype = DNA   length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 57
ggggtgggag gctagctaca acgaaggcac ctc                                  33

SEQ ID NO: 58           moltype = DNA   length = 31
FEATURE                 Location/Qualifiers
misc_feature            1..31
                        note = DNAzymes targeting human p21 mRNA
source                  1..31
                        mol_type = other DNA
                        organism = synthetic construct
SEQUENCE: 58
ccattgagtc cgagccggac gaggggtgg g                                     31

SEQ ID NO: 59           moltype = DNA   length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 59
tccagtccag gctagctaca acgatgagct ggg                                  33

SEQ ID NO: 60           moltype = DNA   length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 60
gaggtagaag gctagctaca acgatagggt gcc                                  33

SEQ ID NO: 61           moltype = DNA   length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 61
tgcctgaggg gctagctaca acgaagaact agg                                  33

SEQ ID NO: 62           moltype = DNA   length = 31
FEATURE                 Location/Qualifiers
misc_feature            1..31
                        note = DNAzymes targeting human p21 mRNA
source                  1..31
                        mol_type = other DNA
                        organism = synthetic construct
SEQUENCE: 62
tgcttgagtc cgagccggac gagcctgagg t                                    31

SEQ ID NO: 63           moltype = DNA   length = 33
FEATURE                 Location/Qualifiers
misc_feature            1..33
                        note = DNAzymes targeting human p21 mRNA
source                  1..33
                        mol_type = other DNA
                        organism = synthetic construct
```

```
SEQUENCE: 63
ggaccctcag gctagctaca acgaccccac agc                                        33

SEQ ID NO: 64           moltype = DNA   length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 64
gtgccaccag gctagctaca acgaatggga ccc                                        33

SEQ ID NO: 65           moltype = DNA   length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 65
cctgtgccag gctagctaca acgacacatg gga                                        33

SEQ ID NO: 66           moltype = DNA   length = 31
FEATURE                 Location/Qualifiers
misc_feature            1..31
                        note = DNAzymes targeting human p21 mRNA
source                  1..31
                        mol_type = other DNA
                        organism = synthetic construct
SEQUENCE: 66
taacccatc cgagccggac gacaaggggg c                                           31

SEQ ID NO: 67           moltype = DNA   length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 67
ataaccccag gctagctaca acgatcaagg ggg                                        33

SEQ ID NO: 68           moltype = DNA   length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 68
tttgagggggg gctagctaca acgacagtgt ctc                                       33

SEQ ID NO: 69           moltype = DNA   length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 69
gctggacgag gctagctaca acgattgagg ggc                                        33

SEQ ID NO: 70           moltype = DNA   length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 70
tggggtggag gctagctaca acgagaggaa ggt                                        33

SEQ ID NO: 71           moltype = DNA   length = 33
FEATURE                 Location/Qualifiers
misc_feature            1..33
                        note = DNAzymes targeting human p21 mRNA
source                  1..33
                        mol_type = other DNA
```

```
                    organism = synthetic construct
SEQUENCE: 71
ggggagggag gctagctaca acgagggtg gat                                        33

SEQ ID NO: 72           moltype = DNA   length = 31
FEATURE                 Location/Qualifiers
misc_feature            1..31
                        note = DNAzymes targeting human p21 mRNA
source                  1..31
                        mol_type = other DNA
                        organism = synthetic construct
SEQUENCE: 72
gcaatgaatc cgagccggac gaggggaggg a                                         31

SEQ ID NO: 73           moltype = DNA   length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 73
tgcaatgaag gctagctaca acgatgggga ggg                                       33

SEQ ID NO: 74           moltype = DNA   length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 74
aaagtgcaag gctagctaca acgagaactg ggg                                       33

SEQ ID NO: 75           moltype = DNA   length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 75
aggccagtag gctagctaca acgagttaca gga                                       33

SEQ ID NO: 76           moltype = DNA   length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 76
gagagaaaag gctagctaca acgaagtcca ggc                                       33

SEQ ID NO: 77           moltype = DNA   length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 77
accaggacag gctagctaca acgaatgggg agc                                       33

SEQ ID NO: 78           moltype = DNA   length = 33
FEATURE                 Location/Qualifiers
misc_feature            1..33
                        note = DNAzymes targeting human p21 mRNA
source                  1..33
                        mol_type = other DNA
                        organism = synthetic construct
SEQUENCE: 78
agaggtttag gctagctaca acgaagtcta ggt                                       33

SEQ ID NO: 79           moltype = DNA   length = 80
FEATURE                 Location/Qualifiers
misc_feature            1..80
                        note = human T7 CDKN1A FORWARD primer
source                  1..80
```

```
                            mol_type = other DNA
                            organism = synthetic construct
SEQUENCE: 79
taatacgact cactatagat gttgagctct ggcatagaag aggctggtgg ctattttgtc     60
cttgggctgc ctgttttcag                                                 80

SEQ ID NO: 80               moltype = DNA   length = 80
FEATURE                     Location/Qualifiers
misc_feature                1..80
                            note = human T7 CDKN1A reverse primer
source                      1..80
                            mol_type = other DNA
                            organism = synthetic construct
SEQUENCE: 80
taaagtcact aagaatcatt tattgagcac ctgctgtata ttcagcattg tgggaggagc     60
tgtgaaagac acagaacagt                                                 80

SEQ ID NO: 81               moltype = DNA   length = 67
FEATURE                     Location/Qualifiers
misc_feature                1..67
                            note = Mouse cdkn1a_REVERSE primer
source                      1..67
                            mol_type = other DNA
                            organism = synthetic construct
SEQUENCE: 81
aatcatcgag aagtatttat tgagcaccag ctttggggtc gggtgtgagg actcgggaca     60
atgcagg                                                               67

SEQ ID NO: 82               moltype = DNA   length = 45
FEATURE                     Location/Qualifiers
misc_feature                1..45
                            note = Mouse cdkn1a_FORWARD primer
source                      1..45
                            mol_type = other DNA
                            organism = synthetic construct
SEQUENCE: 82
taatacgact cactatagtg cagcagccga gaggtgtgag ccgcc                     45

SEQ ID NO: 83               moltype = DNA   length = 33
FEATURE                     Location/Qualifiers
misc_feature                1..33
                            note = mouse DNAzyme 557
source                      1..33
                            mol_type = other DNA
                            organism = synthetic construct
SEQUENCE: 83
gaagaccaag gctagctaca acgactgcgc ttg                                  33

SEQ ID NO: 84               moltype = DNA   length = 33
FEATURE                     Location/Qualifiers
misc_feature                1..33
                            note = mouse DNAzyme 291
source                      1..33
                            mol_type = other DNA
                            organism = synthetic construct
SEQUENCE: 84
gctcccagag gctagctaca acgagaagtt gcc                                  33

SEQ ID NO: 85               moltype = DNA   length = 33
FEATURE                     Location/Qualifiers
misc_feature                1..33
                            note = mouse DNAzyme 639
source                      1..33
                            mol_type = other DNA
                            organism = synthetic construct
SEQUENCE: 85
ggccgaagag gctagctaca acgaggggaa gag                                  33

SEQ ID NO: 86               moltype = DNA   length = 33
FEATURE                     Location/Qualifiers
misc_feature                1..33
                            note = control DNZ_Scramble
source                      1..33
                            mol_type = other DNA
                            organism = synthetic construct
SEQUENCE: 86
aggagaacaa cagtaactgg cgacgggatg agg                                  33

SEQ ID NO: 87               moltype = DNA   length = 33
```

| | |
|---|---|
| FEATURE | Location/Qualifiers |
| misc_feature | 1..33 |
| | note = control DNZ_Scramble for mouse |
| source | 1..33 |
| | mol_type = other DNA |
| | organism = synthetic construct |

SEQUENCE: 87
gaagaggagg gctagctaca acgacgacgg agg                          33

| | |
|---|---|
| SEQ ID NO: 88 | moltype = DNA  length = 15 |
| FEATURE | Location/Qualifiers |
| misc_feature | 1..15 |
| | note = catalytic domain of 10-23 DNAzymes |
| source | 1..15 |
| | mol_type = other DNA |
| | organism = synthetic construct |

SEQUENCE: 88
ggctagctac aacga                                              15

| | |
|---|---|
| SEQ ID NO: 89 | moltype = DNA  length = 14 |
| FEATURE | Location/Qualifiers |
| misc_feature | 1..14 |
| | note = catalytic domain of 8-17 DNAzymes |
| source | 1..14 |
| | mol_type = other DNA |
| | organism = synthetic construct |

SEQUENCE: 89
tccgagccgg acga                                               14

| | |
|---|---|
| SEQ ID NO: 90 | moltype = DNA  length = 11 |
| FEATURE | Location/Qualifiers |
| misc_feature | 1..11 |
| | note = 16.2-11 catalytic core |
| source | 1..11 |
| | mol_type = other DNA |
| | organism = synthetic construct |

SEQUENCE: 90
gtgacccctt g                                                  11

| | |
|---|---|
| SEQ ID NO: 91 | moltype = DNA  length = 19 |
| FEATURE | Location/Qualifiers |
| misc_feature | 1..19 |
| | note = 9-86 catalytic core |
| source | 1..19 |
| | mol_type = other DNA |
| | organism = synthetic construct |

SEQUENCE: 91
tcatgcagcg cgtagtgtc                                          19

| | |
|---|---|
| SEQ ID NO: 92 | moltype = DNA  length = 18 |
| FEATURE | Location/Qualifiers |
| misc_feature | 1..18 |
| | note = 12-91 catalytic core |
| source | 1..18 |
| | mol_type = other DNA |
| | organism = synthetic construct |

SEQUENCE: 92
tgatgcagcg catgtgtc                                           18

| | |
|---|---|
| SEQ ID NO: 93 | moltype = DNA  length = 13 |
| FEATURE | Location/Qualifiers |
| misc_feature | 1..13 |
| | note = 12-91 catalytic core |
| source | 1..13 |
| | mol_type = other DNA |
| | organism = synthetic construct |

SEQUENCE: 93
aagcagttaa gac                                                13

| | |
|---|---|
| SEQ ID NO: 94 | moltype = DNA  length = 22 |
| FEATURE | Location/Qualifiers |
| misc_feature | 1..22 |
| | note = Bipartite I or Bipartite II catalytic core |
| source | 1..22 |
| | mol_type = other DNA |
| | organism = synthetic construct |

SEQUENCE: 94
aaggaggtag gggttccgct cc                                      22

-continued

```
SEQ ID NO: 95              moltype = DNA  length = 20
FEATURE                    Location/Qualifiers
misc_feature               1..20
                           note = Single strand DNA oligonucleotide
source                     1..20
                           mol_type = other DNA
                           organism = synthetic construct
SEQUENCE: 95
tggtatcgtg gaaggactca                                                   20

SEQ ID NO: 96              moltype = DNA  length = 20
FEATURE                    Location/Qualifiers
misc_feature               1..20
                           note = Single strand DNA oligonucleotide
source                     1..20
                           mol_type = other DNA
                           organism = synthetic construct
SEQUENCE: 96
ccagtagagg cagggatgat                                                   20

SEQ ID NO: 97              moltype = DNA  length = 20
FEATURE                    Location/Qualifiers
misc_feature               1..20
                           note = Single strand DNA oligonucleotide
source                     1..20
                           mol_type = other DNA
                           organism = synthetic construct
SEQUENCE: 97
tcaaaggccc gctctacatc                                                   20

SEQ ID NO: 98              moltype = DNA  length = 20
FEATURE                    Location/Qualifiers
misc_feature               1..20
                           note = Single strand DNA oligonucleotide
source                     1..20
                           mol_type = other DNA
                           organism = synthetic construct
SEQUENCE: 98
tgcccagcac tcttaggaac                                                   20

SEQ ID NO: 99              moltype = DNA  length = 24
FEATURE                    Location/Qualifiers
misc_feature               1..24
                           note = Single strand DNA oligonucleotide
source                     1..24
                           mol_type = other DNA
                           organism = synthetic construct
SEQUENCE: 99
tcaagctcat ttcctggtat gaca                                              24

SEQ ID NO: 100             moltype = DNA  length = 20
FEATURE                    Location/Qualifiers
misc_feature               1..20
                           note = Single strand DNA oligonucleotide
source                     1..20
                           mol_type = other DNA
                           organism = synthetic construct
SEQUENCE: 100
tagggcctct cttgctcagt                                                   20

SEQ ID NO: 101             moltype = DNA  length = 20
FEATURE                    Location/Qualifiers
misc_feature               1..20
                           note = Single strand DNA oligonucleotide
source                     1..20
                           mol_type = other DNA
                           organism = synthetic construct
SEQUENCE: 101
gtgtgccgtt gtctcttcgg                                                   20

SEQ ID NO: 102             moltype = DNA  length = 20
FEATURE                    Location/Qualifiers
misc_feature               1..20
                           note = Single strand DNA oligonucleotide
source                     1..20
                           mol_type = other DNA
                           organism = synthetic construct
SEQUENCE: 102
ctcaggtaga ccttgggcag                                                   20
```

```
SEQ ID NO: 103           moltype = DNA  length = 21
FEATURE                  Location/Qualifiers
misc_feature             1..21
                         note = Single strand DNA oligonucleotide
source                   1..21
                         mol_type = other DNA
                         organism = synthetic construct
SEQUENCE: 103
catctggagc agcatggagt c                                              21

SEQ ID NO: 104           moltype = DNA  length = 24
FEATURE                  Location/Qualifiers
misc_feature             1..24
                         note = Single strand DNA oligonucleotide
source                   1..24
                         mol_type = other DNA
                         organism = synthetic construct
SEQUENCE: 104
gttgcccatc atcatcacct gaat                                           24

SEQ ID NO: 105           moltype = DNA  length = 20
FEATURE                  Location/Qualifiers
misc_feature             1..20
                         note = Single strand DNA oligonucleotide
source                   1..20
                         mol_type = other DNA
                         organism = synthetic construct
SEQUENCE: 105
tccttagcca ctccttctgt                                                20

SEQ ID NO: 106           moltype = DNA  length = 19
FEATURE                  Location/Qualifiers
misc_feature             1..19
                         note = Single strand DNA oligonucleotide
source                   1..19
                         mol_type = other DNA
                         organism = synthetic construct
SEQUENCE: 106
agccagagtc cttcagaga                                                 19

SEQ ID NO: 107           moltype = DNA  length = 25
FEATURE                  Location/Qualifiers
misc_feature             1..25
                         note = Single strand DNA oligonucleotide
source                   1..25
                         mol_type = other DNA
                         organism = synthetic construct
SEQUENCE: 107
tcccaaagaa gctgtagttt ttgtc                                          25

SEQ ID NO: 108           moltype = DNA  length = 20
FEATURE                  Location/Qualifiers
misc_feature             1..20
                         note = Single strand DNA oligonucleotide
source                   1..20
                         mol_type = other DNA
                         organism = synthetic construct
SEQUENCE: 108
cccattcctt cttggggtca                                                20

SEQ ID NO: 109           moltype = DNA  length = 24
FEATURE                  Location/Qualifiers
misc_feature             1..24
                         note = Single strand DNA oligonucleotide
source                   1..24
                         mol_type = other DNA
                         organism = synthetic construct
SEQUENCE: 109
ccaacaagca tgtctggtta ggag                                           24

SEQ ID NO: 110           moltype = DNA  length = 23
FEATURE                  Location/Qualifiers
misc_feature             1..23
                         note = Single strand DNA oligonucleotide
source                   1..23
                         mol_type = other DNA
                         organism = synthetic construct
SEQUENCE: 110
```

```
gcaatgctgt tcttgcagtg gta                                            23

SEQ ID NO: 111           moltype = DNA  length = 19
FEATURE                  Location/Qualifiers
misc_feature             1..19
                         note = Single strand DNA oligonucleotide
source                   1..19
                         mol_type = other DNA
                         organism = synthetic construct
SEQUENCE: 111
agcaggtcag caaagaact                                                 19

SEQ ID NO: 112           moltype = DNA  length = 22
FEATURE                  Location/Qualifiers
misc_feature             1..22
                         note = Single strand DNA oligonucleotide
source                   1..22
                         mol_type = other DNA
                         organism = synthetic construct
SEQUENCE: 112
cctcatggac tgattatgga ca                                             22

SEQ ID NO: 113           moltype = DNA  length = 19
FEATURE                  Location/Qualifiers
misc_feature             1..19
                         note = Single strand DNA oligonucleotide
source                   1..19
                         mol_type = other DNA
                         organism = synthetic construct
SEQUENCE: 113
ttccaggctt tgggcatca                                                 19

SEQ ID NO: 114           moltype = DNA  length = 24
FEATURE                  Location/Qualifiers
misc_feature             1..24
                         note = Single strand DNA oligonucleotide
source                   1..24
                         mol_type = other DNA
                         organism = synthetic construct
SEQUENCE: 114
atgttcagca tgttcagcag tgtg                                           24

SEQ ID NO: 115           moltype = DNA  length = 20
FEATURE                  Location/Qualifiers
misc_feature             1..20
                         note = Single strand DNA oligonucleotide
source                   1..20
                         mol_type = other DNA
                         organism = synthetic construct
SEQUENCE: 115
gctcctgcct cacatcatac                                                20

SEQ ID NO: 116           moltype = DNA  length = 20
FEATURE                  Location/Qualifiers
misc_feature             1..20
                         note = Single strand DNA oligonucleotide
source                   1..20
                         mol_type = other DNA
                         organism = synthetic construct
SEQUENCE: 116
ggcttctctg catctgtgaa                                                20

SEQ ID NO: 117           moltype = DNA  length = 22
FEATURE                  Location/Qualifiers
misc_feature             1..22
                         note = Single strand DNA oligonucleotide
source                   1..22
                         mol_type = other DNA
                         organism = synthetic construct
SEQUENCE: 117
gagacacacc agagcagata cc                                             22

SEQ ID NO: 118           moltype = DNA  length = 21
FEATURE                  Location/Qualifiers
misc_feature             1..21
                         note = Single strand DNA oligonucleotide
source                   1..21
                         mol_type = other DNA
                         organism = synthetic construct
```

-continued

```
SEQUENCE: 118
ggggaaccca tgaatttagc c                                              21

SEQ ID NO: 119          moltype = DNA   length = 21
FEATURE                 Location/Qualifiers
misc_feature            1..21
                        note = Single strand DNA oligonucleotide
source                  1..21
                        mol_type = other DNA
                        organism = synthetic construct
SEQUENCE: 119
tatggggctg ggagtagttg t                                              21

SEQ ID NO: 120          moltype = DNA   length = 21
FEATURE                 Location/Qualifiers
misc_feature            1..21
                        note = Single strand DNA oligonucleotide
source                  1..21
                        mol_type = other DNA
                        organism = synthetic construct
SEQUENCE: 120
gggagccgag agaaaacagt c                                              21

SEQ ID NO: 121          moltype = DNA   length = 25
FEATURE                 Location/Qualifiers
misc_feature            1..25
                        note = Single strand DNA oligonucleotide
source                  1..25
                        mol_type = other DNA
                        organism = synthetic construct
SEQUENCE: 121
gacagcagag gaagaccatg tggac                                          25

SEQ ID NO: 122          moltype = DNA   length = 24
FEATURE                 Location/Qualifiers
misc_feature            1..24
                        note = Single strand DNA oligonucleotide
source                  1..24
                        mol_type = other DNA
                        organism = synthetic construct
SEQUENCE: 122
gagtggtaga aatctgtcat gctg                                           24

SEQ ID NO: 123          moltype = DNA   length = 21
FEATURE                 Location/Qualifiers
misc_feature            1..21
                        note = Single strand DNA oligonucleotide
source                  1..21
                        mol_type = other DNA
                        organism = synthetic construct
SEQUENCE: 123
ttggctcccc tgtacctttt g                                              21

SEQ ID NO: 124          moltype = DNA   length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 124
tggagctgag agggtactga                                                20

SEQ ID NO: 125          moltype = DNA   length = 31
FEATURE                 Location/Qualifiers
misc_feature            1..31
                        note = control DNZ_Scramble
source                  1..31
                        mol_type = other DNA
                        organism = synthetic construct
SEQUENCE: 125
gtgtggcgcc cgagccggac gagagtggag g                                   31
```